US011697804B2

(12) United States Patent
Green et al.

(10) Patent No.: US 11,697,804 B2
(45) Date of Patent: Jul. 11, 2023

(54) TRANSCRIPTIONALLY TARGETED AND CPG-FREE PLASMID FOR THERANOSTIC GENE THERAPY

(71) Applicant: The Johns Hopkins University, Baltimore, MD (US)

(72) Inventors: Jordan J. Green, Nottingham, MD (US); Martin G. Pomper, Baltimore, MD (US); Camila Gadens Zamboni, Curitiba (BR); Hannah Vaughan, Baltimore, MD (US); Il Minn, Elliott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 689 days.

(21) Appl. No.: 16/589,647

(22) Filed: Oct. 1, 2019

(65) Prior Publication Data

US 2020/0140831 A1     May 7, 2020

Related U.S. Application Data

(60) Provisional application No. 62/739,576, filed on Oct. 1, 2018.

(51) Int. Cl.
| | | |
|---|---|---|
| *C12N 9/12* | (2006.01) | |
| *C12N 15/52* | (2006.01) | |
| *A61K 48/00* | (2006.01) | |
| *C12N 15/85* | (2006.01) | |
| *A61K 35/00* | (2006.01) | |
| *C08G 73/02* | (2006.01) | |
| *A61K 51/04* | (2006.01) | |
| *B82Y 5/00* | (2011.01) | |
| *A61K 45/00* | (2006.01) | |
| *A61K 31/522* | (2006.01) | |

(52) U.S. Cl.
CPC ............ *C12N 9/1211* (2013.01); *A61K 35/00* (2013.01); *A61K 48/0041* (2013.01); *C08G 73/02* (2013.01); *C12N 15/52* (2013.01); *C12N 15/85* (2013.01); *A61K 31/522* (2013.01); *A61K 45/05* (2013.01); *A61K 51/0459* (2013.01); *B82Y 5/00* (2013.01); *C12N 2820/007* (2013.01); *C12N 2830/008* (2013.01); *C12N 2830/15* (2013.01); *C12N 2840/007* (2013.01); *C12N 2840/60* (2013.01); *C12Y 207/01021* (2013.01)

(58) Field of Classification Search
None
See application file for complete search history.

(56) References Cited

U.S. PATENT DOCUMENTS

| | | | |
|---|---|---|---|
| 8,287,849 B2 | 10/2012 | Langer et al. | |
| 8,992,991 B2 | 3/2015 | Green et al. | |
| 9,717,694 B2 | 8/2017 | Green et al. | |
| 9,884,118 B2 | 2/2018 | Green et al. | |
| 2012/0114759 A1 | 5/2012 | Green et al. | |
| 2012/0128782 A1 | 5/2012 | Green et al. | |
| 2015/0250881 A1 | 9/2015 | Green et al. | |
| 2015/0273071 A1 | 10/2015 | Green et al. | |
| 2016/0122390 A1 | 5/2016 | Popel et al. | |
| 2016/0374949 A9 | 12/2016 | Green et al. | |
| 2018/0028455 A1 | 2/2018 | Green et al. | |
| 2018/0112038 A1 | 4/2018 | Green et al. | |
| 2018/0177881 A1 | 6/2018 | Green et al. | |

OTHER PUBLICATIONS

Nakaya, et al. (2003) "In vitro model of suicide gene therapy for alpha-fetoprotein-producing gastric cancer", Anticancer Research, 23(5A): 3795-800 (Abstract Only). (Year: 2003).*
Yaghoubi, et al. (2012) "Positron Emission Tomography Reporter Genes and Reporter Probes: Gene and Cell Therapy Applications", Theranostics, 2(4): 374-91. (Year: 2012).*
Kauffman, et al. (Aug. 1, 1991) "Mutations in the thymidine kinase gene that allow expression of the enzyme in quiescent (G0) cells", Oncogene, 6(8): 1427-35. (Year: 1991).*
Pantuck, et al. (2001) "CL1-SR39: Anon-invasive molecular imaging model of prostate cancer suicide gene therapy using positron emission tomography", Journal of Urology, 168(3): 1193-98 (Abstract Only). (Year: 2001).*
Kim, et al. (2002) "The human elongation factor 1 alpha (EF-1α) first intron highly enhances expression of foreign genes from the murine cytomegalovirus promoter", Journal of Biotechnology, 93: 183-87. (Year: 2002).*
Vaughan, et al. (2022) "Polymeric nanoparticles for dual-targeted theranostic gene delivery to hepatocellular carcinoma", Science Advances, 8: article eabo6046, 12 pages long. (Year: 2022).*
Anderson et al., Structure/property studies of polymeric gene delivery using a library of poly(beta-amino esters) Mol Ther. Mar. 2005;11(3):426-34.
Arzumanyan et al., Pathogenic mechanism in HBV- and HCV-associated hepatocellular carcinoma. Nat Rev Cancer. Feb. 2013;13(2):123-35.
Barton et al., Feasibility of adenovirus-mediated hNIS gene transfer and 131I radioiodine therapy as a definitive treatment for localized prostate cancer. Mol Ther. Jul. 2011;19(7):1353-9.
Black et al., Herpes simplex virus-1 thymidin kinase mutants created by semi-random sequence mutagenesis improve prodrug-mediated tumor cell killing. Cancer Res. Apr. 1, 2001;61(7):3022-6.
Castanares et al., Evaluation of prostate-specific membrane antigen as an imaging reporter. J Nucl Med. May 2014;55(5):805-11.

(Continued)

*Primary Examiner* — Robert M Kelly
(74) *Attorney, Agent, or Firm* — Casimir Jones, S.C.; Jeffrey W. Childers

(57) ABSTRACT

A DNA plasmid useful for diagnostic and therapeutic gene therapy is disclosed. Improvements to gene therapy methods known in the art are provided to ensure cancer-targeting, high efficacy, and long durability of expression. The DNA plasmid is combined with compositions of polymeric nanoparticles for non-viral gene therapy to treat cancer, including hepatocellular carcinoma and prostate cancer.

35 Claims, 40 Drawing Sheets
(25 of 40 Drawing Sheet(s) Filed in Color)
Specification includes a Sequence Listing.

(56) References Cited

OTHER PUBLICATIONS

Check. A tragic setback. Nature. Nov. 14, 2002;420(6912):116-8.
Dey et al., Suicide gene therapy by herpes simplex virus-1 thymidine kinase (HSV-TK), in Targets in Gene Therapy. InTech. 2011. 65-76.
El-Serag et al., Hepatocellular carcinoma: epidemiology and molecular carcinogenesis. Gastroenterology. Jun. 2007;132(7):2557-76.
Farré et al., Identification of patterns in biological sequences at the ALGGEN server: PROMO and MALGEN. Nucleic Acids Res. Jul. 1, 2003;31(13):3651-3.
Hyde et al., CpG-free plasmids confer reduced inflammation and sustained pulmonary gene expression. Nat Biotechnol. May 2008;26(5):549-51.
Ido et al., Gene therapy for hepatoma cells using a retrovirus vector carrying herpes simplex virus thymidine kinase gene under the control of human alpha-fetoprotein gene promoter. Cancer Res. Jul. 15, 1995;55(14):3105-9.
Iyer et al., Exploiting the enhanced permeability and retention effect for tumor targeting. Drug Discov Today. Sep. 2006;11(17-18):812-8.
Karlsson et al., Biodegradable Polymeric Nanoparticles for Therapeutic Cancer Treatments. Annu Rev Chem Biomol Eng. Jun. 7, 2018;9:105-127.
Kim et al., Antitumoral effects of recombinant adenovirus YKL-1001, conditionally replicating in alpha-fetoprotein-producing human liver cancer cells. Cancer Lett. Jun. 6, 2002;180(1):23-32.
Kim et al., Differential polymer structure tunes mechanism of cellular uptake and transfection routes of poly(β-amino ester) polyplexes in human breast cancer cells. Bioconjug Chem. Jan. 15, 2014;25(1):43-51.
Kull et al., Mixturs of quaternary ammonium compounds and long-chain fatty acids as antifungal agents. Appl Microbiol. Nov. 1961;9(6):538-41.
Lan et al., In vivo selective gene expression and therapy mediated by adenoviral vectors for human carcinoembryonic antigen-producing gastric carcinoma. Cancer Res. Oct. 1, 1997;57(19):4279-84.
Marshall. Gene therapy death prompts review of adenovirus vector. Science. Dec. 17, 1999;286(5448):2244-5.
Messeguer et al., PROMO: detection of known transcription regulatory elements using species-tailored searches. Bioinformatics. Feb. 2002;18(2):333-4.
Nathwani et al., Adenovirus-associated virus vector-mediated gene transfer in hemophilia B. N Engl J Med. Dec. 22, 2011;365(25):2357-65.
Ponde et al., Rapid and reproducible radiosynthesis of [18F] FHBG. Nuclear Medicine and Biology, 2004. 31(1): p. 133-138.
Riley et al., Recent Advances in Nanomaterials for Gene Delivery—A Review. Nanomaterials (Basel). Apr. 28, 2017;7(5):94. 19 pages.
Sunshine et al., Effects of base polymer hydrophobicity and end-group modification on polymeric gene delivery. Biomacromolecules. Oct. 10, 2011;12(10):3592-600.
Tanaka et al., Molecular tracing of the global hepatitis C virus epidemic predicts regional patterns of hepatocellular carcinoma mortality. Gastroenterology. Mar. 2006;130(3):703-14.
Tzeng et al., Biomaterial-mediated cancer-specific DNA delivery to liver cell cultures using synthetic poly(beta-amino ester)s. J Biomed Mater Res A. Jul. 2013;101(7):1837-45.
Tzeng et al., Non-viral gene delivery nanoparticles based on poly(β-amino esters) for treatment of glioblastoma. Biomaterials. Aug. 2011;32(23):5402-10.
Wang et al., Adeno-associated virus vector carrying human minidystrophin genes effectively ameliorates muscular dystrophy in mdx mouse model. Proc Natl Acad Sci U S A. Dec. 5, 2000;97(25):13714-9.
Wiewrodt et al., Adenovirus-mediated gene transfer of enhanced Herpes simplex virus thymidine kinase mutants improves prodrug-mediated tumor cell killing. Cancer Gene Ther. May 2003;10(5):353-64.
Wuts et al., Greene's Protective Groups in Organic Synthesis, 4th ed. John Wiley & Sons. 2007. TOC only. 6 pages.
Zamboni et al., Polymeric nanoparticles as cancer-specific DNA delivery vectors to human hepatocellular carcinoma. J Control Release. Oct. 10, 2017;263:18-28.
Zhang et al., Complete eradication of hepatomas using an oncolytic adenovirus containing AFP promoter controlling E1A and an E1B deletion to drive IL-24 expression. Cancer Gene Ther. Sep. 2012;19(9):619-29.

* cited by examiner

Fig. 23

| Name | Sequence | SEQ ID NO: |
|---|---|---|
| CpG Free SR39 Amino Acid Sequence | MASYPGHQHASAFDQAARSRGHSNRRTALRPRRQQEATEVRPEQK MPTLLRVYIDGPHGMGKTTTTQLLVALGSRDDIVYVPEPMTYWRVL GASETIANIYTTQHRLDQGEISAGDAAVVMTSAQITMGMPYAVTDA VLAPHIGGEAGSSHAPPPALTIFLDRHPIAFMLCYPAARYLMGSMTP QAVLAFVALIPPTLPGTNIVLGALPEDRHIDRLAKRQRPGERLDLAM LAAIRRVYGLLANTVRYLQGGGSWREDWGQLSGTAVPPQGAEPQS NAGPRPHIGDTLFTLFRAPELLAPNGDLYNVFAWALDVLAKRLRPM HVFILDYDQSPAGCRDALLQLTSGMVQTHVTTPGSIPTICDLARTFAR EMGEAN | 1 |
| CpG Free SR39 Nucleic Acid Sequence | ATGGCTTCCTACCCTGGCCATCAGCATGCCTCTGCCTTTGACCAG GCTGCCAGATCTAGAGGCCATAGCAACAGAAGAACTGCCTTGAG ACCTAGAAGACAGCAAGAAGCCACTGAAGTCAGACCTGAGCAGA AAATGCCCACCCTACTGAGGGTTTATATAGATGGTCCCCATGGGA TGGGGAAAACCACCACCACCCAACTGCTGGTGGCCCTGGGTAGC AGAGATGATATTGTCTATGTACCTGAGCCCATGACTTACTGGAGG GTGCTGGGGGCTTCTGAGACAATTGCCAACATCTACACCACACAA CACAGACTGGACCAGGGTGAGATATCTGCTGGGGATGCTGCTGT GGTAATGACATCTGCCCAGATAACAATGGGCATGCCTTATGCTGT GACAGATGCTGTTCTGGCTCCTCATATTGGGGGGAGGCTGGGAG CTCACATGCCCCTCCCCCTGCCCTCACCATTTTCCTGGACAGACAT CCCATTGCCTTCATGCTGTGCTACCCTGCTGCCAGATACCTTATGG GCAGCATGACCCCCCAGGCTGTGCTGGCCTTTGTGGCCCTCATCC CCCCTACCTTGCCTGGCACAAACATTGTGTTGGGGGCCCTTCCTG AGGACAGACACATTGACAGACTGGCCAAAAGACAGAGACCTGGA GAGAGACTTGACCTGGCTATGCTGGCTGCCATTAGAAGGGTTTAT GGGCTGCTTGCCAATACTGTGAGATATCTGCAGGGAGGAGGGTC CTGGAGAGAGGATTGGGGACAGCTTTCTGGGACTGCTGTGCCTCC CCAGGGTGCTGAGCCCCAGAGCAATGCTGGCCCAAGACCCCATA TTGGGGACACCTTATTTACCCTGTTTAGAGCCCCTGAGTTGCTGG CCCCCAATGGAGACCTGTACAATGTGTTTGCCTGGGCCTTGGATG TCTTGGCCAAAAGACTCAGACCCATGCATGTCTTTATCCTGGATT ATGACCAATCCCCTGCTGGCTGCAGAGATGCCCTGCTGCAACTTA CCTCTGGGATGGTCCAGACCCATGTCACCACCCCTGGCTCCATAC CCACCATCTGTGACCTGGCCAGAACCTTTGCCAGAGAGATGGGG GAGGCTAACTGA | 2 |
| CpG Free AFP Promoter/Enhancer Nucleic Acid Sequence | GCTTAGAAATATGGGGGTAGGGGTGGTGGTGGTAATTCTGTTTTC TCCCCATAGGTGAGATAAGCATTGGGTTAAATGTGCTTTCTCTCT CTCCCTCTCCTTTCTTAAGAATTAAGGGACAGACTATGGGCTGGA GGACTTTGAGGATGTCTGTCTCATAACACTTGGGTTGTATCTGTTC TATGGGGCTTGTTTTAAGCTTGGCAACTTGCAACAGGGTTCACTG ACTTTCTCCCCAGGCCCAAGGTACTGTCCTCTTTTCATATCTGTTT TGGGGCCTCTGGGGCTTGAATATCTGAGAAAATATAAACATTTCA ATAATGTTCTGTGGTGAGATGAGTATGAGAGATGTGTCATTCATT TGTATCAATGAATGAATGAGGACAATTAGTGTATAAATCCTTAGT ACAACAATCTGAGGGTAGGGGTGGTACTATTCAATTTCTATTTAT AAAGATACTTATTTCTATTTATTTATGCTTGTGACAAATGTTTTGT TTGGGACCACAGGAATCACAAAGATGAGTCTTTGAATTTAAGAA GTTAATGGTCCAGGAATAATTACATAGCTTACAAATGACTATGAT ATACCATCAAACAAGAGGTTCCATGAGAAATAATCTGAAAGGT TTAATAAGTTGTCAAAGGTGAGAGGGCTCTTCTCTAGCTAGAGAC TAATCAGAAATACATTCAGGGATAATTATTTGAATAGACCTTAAG GGTTGGGTACATTTTGTTCAAGCATTGATGGAGAAGGAGAGTGA ATATTTGAAAACATTTTCAACTAACCAACCACCCAATCCAACAAA CAAAAAATGAAAAGAATCTCAGAAACAGTGAGATAAGAGAAGG AATTTTCTCACAACCCACATGTATAGCTCAACTGCTCTGAAGAAG TATATATCTAATATTTAACACTAACATCATGCTAATAATGATAAT | 3 |

| Name | Sequence | SEQ ID NO: |
|---|---|---|
| | AATTACTGTCATTTTTTAATGTCTATAAGTACCAGGCATTTAGAA<br>GATATTATTCCATTTATATATCAAAATAAACTTGAGGGGATAGAT<br>CATTTTCATGATATATGAGAAAAATTAAAAATCAGATTGAATTAT<br>TTGCCTGTCATACAGCTAATAATTGACCATAAGACAATTAGATTT<br>AAATTAGTTTTGAATCTTTCTAATACCAAAGTTCAGTTTACTGTTC<br>CATGTTGCTTCTGAGTGGCTTCACAGACTTATGAAAAAGTAAATG<br>GAATCAGAATTACATCAATGCAAAAGCATTGCTGTGAACTCTGTA<br>CTTAGGACTAAACTTTGAGCAATAACACATATAGATTGAGGATTG<br>TTTGCTGTTAGTATACAAACTCTGGTTCAAAGCTCCTCTTTATTGC<br>TTGTCTTGGAAAATTTGCTGTTCTTCATGGTTTCTCTTTTCACTGCT<br>ATCTATTTTCTCAACCACTCACATGGCTACAATAACTGTCTGCAA<br>GCTTATGATTCCCAAATGTCTATCTCTAGCCTCAATCTTGTTCCAG<br>AAGATAAAAGTAGTATTCAAATGCACATCAACATCTCCACTTGG<br>AGGGCTTAAAGATGTTTCAACATACAAACTGGGGAGTTTTGCCTG<br>GAATGTTTCCTAAAATGTGTCCTGTAGCACATAGGGTCCTCTTGTT<br>CCTTAAAATCTAATTACTTTTAGCCCAGTGCTCATCCCACCTATGG<br>GGAGATGAGAGTGAAAAGGGAGCCTGATTAATAATTACACTAAG<br>TCAATAGGCATAGAGCCAGGACTGTTTGGGTAAACTGGTCACTTT<br>ATCTTAAACTAAATATATCCAAAACTGAACATGTACTTAGTTACT<br>AAGTCTTTGACTTTATCTCATTCATACCACTCAGCTTTATCCAGGC<br>CACTAGAGTTTGAGGAGAATATTTGTTATATTTGCAAAATAAAAT<br>AAGTTTGCAAGTTTTTTTTTTCTGCCCCAAAGAGCTCTGTGTCCTT<br>GAACATAAAATACAAATAACTGCTATGCTGTTAATTATTGACAAA<br>TGTCCCATTTTCAACCTAAGGAAATACCATAAAGTAACAGATATA<br>CCAACAAAGGTTACTAGTTAACAGGCATTGCCTGAAAAGAGTA<br>TAAAAGAATTTCAGCATGATTTTCCATATTGTGCTTCCACCACTGC<br>CAATAACAAAATAACTAGCAAC | |
| pCpGfree-vitro Neomycin backbone (Invivogen) | TTAATTAAAATTATCTCTAAGGCATGTGAACTGGCTGTCTTGGTTT<br>TCATCTGTACTTCATCTGCTACCTCTGTGACCTGAAACATATTTAT<br>AATTCCATTAAGCTGTGCATATGATAGATTTATCATATGTATTTC<br>CTTAAAGGATTTTTGTAAGAACTAATTGAATTGATACCTGTAAAG<br>TCTTTATCACACTACCCAATAAATAATAAATCTCTTTGTTCAGCTC<br>TCTGTTTCTATAAATATGTACCAGTTTTATTGTTTTTAGTGGTAGT<br>GATTTTATTCTCTTTCTATATATATACACACATGTGTGCATTCA<br>TAAATATATACAATTTTTATGAATAAAAAATTATTAGCAATCAAT<br>ATTGAAAACCACTGATTTTTGTTTATGTGAGCAAACAGCAGATTA<br>AAAGGAATTTCAATTGCCTGCAGGAGTCAATGGGAAAAACCCAT<br>TGGAGCCAAGTACACTGACTCAATAGGGACTTTCCATTGGGTTTT<br>GCCCAGTACATAAGGTCAATAGGGGGTGAGTCAACAGGAAAGTC<br>CCATTGGAGCCAAGTACATTGAGTCAATAGGGACTTTCCAATGGG<br>TTTTGCCCAGTACATAAGGTCAATGGGAGGTAAGCCAATGGGTTT<br>TTCCCATTACTGACATGTATACTGAGTCATTAGGGACTTTCCAAT<br>GGGTTTTGCCCAGTACATAAGGTCAATAGGGGTGAATCAACAGG<br>AAAGTCCCATTGGAGCCAAGTACACTGACTCAATAGGGACTTTCC<br>ATTGGGTTTTGCCCAGTACAAAAGGTCAATAGGGGTGAGTCAAT<br>GGGTTTTTCCCATTATTGGCACATACATAAGGTCAATAGGGGTGA<br>CTAGTGGAGAAGAGCATGCTTGAGGGCTGAGTGCCCCTCAGTGG<br>GCAGAGAGCACATGGCCCACAGTCCCTGAGAAGTTGGGGGGAGG<br>GGTGGGCAATTGAACTGGTGCCTAGAGAAGGTGGGGCTTGGGTA<br>AACTGGGAAAGTGATGTGGTGTACTGGCTCCACCTTTTTCCCCAG<br>GGTGGGGGAGAACCATATATAAGTGCAGTAGTCTCTGTGAACATT<br>CAAGCTTCTGCCTTCTCCCTCCTGTGAGTTTGGTAAGTCACTGACT<br>GTCTATGCCTGGGAAAGGGTGGGCAGGAGATGGGGCAGTGCAGG<br>AAAAGTGGCACTATGAACCCTGCAGCCCTAGACAATTGTACTAAC<br>CTTCTTCTCTTTCCTCTCCTGACAGGTTGGTGTACAGTAGCTTCCA<br>AGTACTAAGATCTAGTGCACAGGGCCCACCATGGAGCTAGCTGG<br>CCAGACATGATAAGATACATTGATGAGTTTGGACAAACCACAAC<br>TAGAATGCAGTGAAAAAATGCTTTATTTGTGAAATTTGTGATGC<br>TATTGCTTTATTTGTAACCATTATAAGCTGCAATAAACAAGTTAA<br>CAACAACAATTGCATTCATTTTATGTTTCAGGTTCAGGGGGAGGT | 4 |

*Fig. 23 (cont.)*

| Name | Sequence | SEQ ID NO: |
|---|---|---|
| | GTGGGAGGTTTTTTAAAGCAAGTAAAACCTCTACAAATGTGGTAT GGAATTGGAGCCCCACTGTGTTCATCTTACAGATGGAAATACTGA CATTCAGAGGAGTTAGTTAACTTGCCTAGGTGATTCAGCTAATAA GTGCAAGAAAGATTTCAATCCAAGGTGATTTGATTCTGAAGCCTG TGCTAATCACATTACACCAAGCTACAACTTCATTTATAAATAATA AGTCAGCTTTCAAGGGCCTTTCAGGTGTCCTGCACTTCTACAAGC TGTGCCATTTAGTGAACACAAAATGAGCCTTCTGATGAAGTAGTC TTTTCATTATTTCAGATATTAGAACACTAAAATTCTTAGCTGCCAG CTGATTGAAGGCTGGGACAAAATTCAAACATGCATCTACAACAA TATATATCTCAATGTTAGTCTCCAAATTCTATTGACTTCAACTCAA GAGAATATAAAGAGCTAGTCTTTATACACTCTTTAAGGTATGATA TCATCTGGAAAGTAACAAAATTGATGCAAATTTGAATGAACTTTA TCATGGTGTATTTACACAATGTGTTTCTTCTCCCTGCAATGTATTT CTTTCTCTAATTCCTTCCATTTGATCTTTCATACACAATCTGGTTCT GATGTATGTTTTTTGGATGCACTTTTCAACTCCAAAAGACAGAGC TAGTTACTTTCTTCCTGGTGCTCCAAGCACTGTATTTGTATCTGTA TTCAAGCCCTTTGCAATATTGTACTGGATCATTATTTCACCTCTAG GATGGCTTCCCCAGGCAACTTGTGTTCACCCAGAGACTACATTTT GTATCTTGTTGACCTTTGAACTTCCACCAGTGTCTAAAAATAATAT GTATGCAAAATTACTTGCTATGAGAATGTATAATTAAACAATATA AAAAGGAGAAGCAAGGAGAGAAACACAGGTGTGTATTTGTGTTT GTGTGCTTAAAAGGCAGTGTGGAAAAGGAAGAAATGCCATTTAT AGTGAGGAGACAAAGTTATATTACCTCTTATCTGGCTTTTAAGGA GATTTGCTGAGCTAAAAATCCTATATTCATAGAAAAGCCTTACC TGAGTTGCCAATACCTCAATTCTAAAATACAGCATAGCAAAACTT TAACCTCCAAATCAAGCCTCTACTTGAATCCTTTTCTGAGGGATG AATAAGGCATAGGCATCAGGGGCTGTTGCCAATGTGCATTAGCTG TTTGCAGCCTCACCTTCTTTCATGGAGTTTAAGATATAGTGTATTT TCCCAAGGTTTGAACTAGCTCTTCATTTCTTTATGTTTTAAATGCA CTGACCTCCCACATTCCCTTTTTAGTAAAATATTCAGAAATAATTT AAATACATCATTGCAATGAAAATAAATGTTTTTTATTAGGCAGAA TCCAGATGCTCAAGGCCCTTCATAATATCCCCCAGTTTAGTAGTT GGACTTAGGGAACAAAGGAACCTTTAATAGAAATTGGACAGCAA GAAAGCTCTAGCTTTAGAAGAACTCATCAAGAAGTCTGTAGAAG GCAATTCTCTGGGAGTCAGGGGCTGCAATGCCATAGAGCACTAG GAACCTGTCTGCCCACTCTCCCCCTAGCTCTTCTGCTATGTCCCTG GTTGCTAGGGCAATGTCCTGGTACCTGTCAGCCACTCCCAGCCTG CCACAGTCTATGAAGCCAGAGAACCTTCCATTTTCAACCATGATG TTGGGAAGGCAGGCATCCCCATGAGTCACCACTAGGTCCTCACCA TCTGGCATGGATGCCTTGAGCCTGGCAAATAGTTCAGCAGGGGCC AGGCCCTGGTGTTCTTCATCCAAGTCATCTTGGTCCACCAGGCCA GCCTCCATCCTGGTTCTGGCCCTCTCTATCCTGTGCTTGGCCTGGT GGTCAAAGGGGCAGGTGGCTGGGTCAAGGGTGTGGAGTCTTCTC ATGGCATCAGCCATGATTGACACTTTCTCAGCTGGAGCTAGGTGA GAGGAAAGGAGGTCCTGCCCAGGCACCTCACCTAGTAGGAGCCA GTCCCTTCCAGCTTCTGTGACCACATCAAGGACAGCTGCACAGGG GACCCCAGTTGTTGCCAACCAGGAGAGTCTGGCAGCCTCATCCTG GAGCTCATTGAGAGCCCCACTGAGGTCTGTCTTTACAAAAAGGAC TGGCCTGCCTTGGGCTGAAAGTCTGAAAACTGCTGCATCAGAGCA ACCAATGGTCTGCTGTGCCCAGTCATAGCCAAACAGTCTCTCAAC CCAGGCAGCTGGAGAACCTGCATGTAGGCCATCTTGTTCAATCAT GATGGCTCCTCCTGTCAGGAGAGGAAAGAGAAGAAGGTTAGTAC AATTGCTATAGTGAGTTGTATTATACTATGCTTATGATTAATTGTC AAACTAGGGCTGCAGGGTTCATAGTGCCACTTTTCCTGCACTGCC CCATCTCCTGCCCACCCTTTCCCAGGCATAGACAGTCAGTGACTT ACCAAACTCACAGGAGGGAGAAGGCAGAAGCTTTTGCAAAAGC CTAGGCCTCCAAAAAAGCCTCCTCACTACTTCTGGAATAGCTCAG AGGCCCAGGGGGCCTGGGCCTCTGCATAAATAAAAAAATTAGT CAGCCTGGGGCTGGGGTGGGGCAGGGGTGGGGGGCCAACTGGG CAGGGGTGGGGGGCCACTAGTGGGACTATGGTTGCTGACTAATT | |

*Fig. 23 (cont.)*

| Name | Sequence | SEQ ID NO: |
|---|---|---|
| | GAGATGCATGCTTTGCATACTTCTGCCTGCTGGGGAGCCTGGGGA<br>CTTTCCACACCTGGTTGCTGACTAATTGAGATGCATGCTTTGCATA<br>CTTCTGCCTGCTGGGGAGCCTGGGGACTTTCCACACCCTAACTGA<br>CACACATTCCACAGCTGGTTCTTTCAGCCTCAGAAGGTACCTAAC<br>CAAGTTCCTCTTTCAGAGGTTATTTCAGGCCCTGCAGGAATTCAG<br>TCAATATGTTCACCCCAAAAAAGCTGTTTGTTAACTTGTCAACCT<br>CATTCTAAAATGTATATAGAAGCCCAAAAGACAATAACAAAAAT<br>ATTCTTGTAGAACAAAATGGGAAAGAATGTTCCACTAAATATCAA<br>GATTTAGAGCAAAGCATGAGATGTGTGGGGATAGACAGTGAGGC<br>TGATAAAATAGAGTAGAGCTCAGAAACAGACCCATTGATATATG<br>TAAGTGACCTATGAAAAAATATGGCATTTTACAATGGGAAAAT<br>GATGGTCTTTTTCTTTTTTAGAAAAACAGGGAAATATATTTATATG<br>TAAAAAATAAAAGGGAACCCATATGTCATACCATACACACAAAA<br>AAATTCCAGTGAATTATAAGTCTAAATGGAGAAGGCAAAACTTT<br>AAATCTTTTAGAAAATAATATAGAAGCATGCCATCAAGACTTCAG<br>TGTAGAGAAAAATTTCTTATGACTCAAAGTCCTAACCACAAAGAA<br>AAGATTGTTAATTAGATTGCATGAATATTAAGACTTATTTTTAAA<br>ATTAAAAACCATTAAGAAAAGTCAGGCCATAGAATGACAGAAA<br>ATATTTGCAACACCCCAGTAAAGAGAATTGTAATATGCAGATTAT<br>AAAAAGAAGTCTTACAAATCAGTAAAAATAAAACTAGACAAAA<br>ATTTGAACAGATGAAAGAGAAACTCTAAATAATCATTACACATG<br>AGAAACTCAATCTCAGAAATCAGAGAACTATCATTGCATATACAC<br>TAAATTAGAGAAATATTAAAAGGCTAAGTAACATCTGTGGCTTAA<br>TTAAGTTATCCTAGGAAACCTTAAAACCTTTAAAAGCCTTATATA<br>TTCTTTTTTTTCTTATAAAACTTAAAACCTTAGAGGCTATTTAAGT<br>TGCTGATTTATATTAATTTTATTGTTCAAACATGAGAGCTTAGTAC<br>ATGAAACATGAGAGCTTAGTACATTAGCCATGAGAGCTTAGTAC<br>ATTAGCCATGAGGGTTTAGTTCATTAAACATGAGAGCTTAGTACA<br>TTAAACATGAGAGCTTAGTACATACTATCAACAGGTTGAACTGCT<br>GATT | |
| Complete CMV-SR39 plasmid: pCpGfree-vitroNmcs-CpGfreeCMV-EF1-CpGfreeSR39 nucleic acid sequence | TTAATTAAAATTATCTCTAAGGCATGTGAACTGGCTGTCTTGGTTT<br>TCATCTGTACTTCATCTGCTACCTCTGTGACCTGAAACATATTTAT<br>AATTCCATTAAGCTGTGCATATGATAGATTTATCATATGTATTTC<br>CTTAAAGGATTTTTGTAAGAACTAATTGAATTGATACCTGTAAAG<br>TCTTTATCACACTACCCAATAAATAATAAATCTCTTTGTTCAGCTC<br>TCTGTTTCTATAAATATGTACCAGTTTTATTGTTTTTAGTGGTAGT<br>GATTTTATTCTCTTTCTATATATATACACACATGTGTGCATTCA<br>TAAATATATACAATTTTTATGAATAAAAAATTATTAGCAATCAAT<br>ATTGAAAACCACTGATTTTTGTTTATGTGAGCAAACAGCAGATTA<br>AAAGGAATTTCAATTGCCTGCAGGAGTCAATGGGAAAAACCCAT<br>TGGAGCCAAGTACACTGACTCAATAGGGACTTTCCATTGGGTTTT<br>GCCCAGTACATAAGGTCAATAGGGGGTGAGTCAACAGGAAAGTC<br>CCATTGGAGCCAAGTACATTGAGTCAATAGGGACTTTCCAATGGG<br>TTTTGCCCAGTACATAAGGTCAATGGGAGGTAAGCCAATGGGTTT<br>TTCCCATTACTGACATGTATACTGAGTCATTAGGGACTTTCCAAT<br>GGGTTTTGCCCAGTACATAAGGTCAATAGGGGTGAATCAACAGG<br>AAAGTCCCATTGGAGCCAAGTACACTGACTCAGTCAATGGGACTTTCC<br>ATTGGGTTTTGCCCAGTACAAAAGGTCAATAGGGGGTGAGTCAAT<br>GGGTTTTTCCCATTATTGGCACATACATAAGGTCAATAGGGGTGA<br>CTAGTGGAGAAGAGCATGCTTGAGGGCTGAGTGCCCCTCAGTGG<br>GCAGAGAGCACATGGCCCACAGTCCCTGAGAAGTTGGGGGGAGG<br>GGTGGGCAATTGAACTGGTGCCTAGAGAAGGTGGGGCTTGGGTA<br>AACTGGGAAAGTGATGTGGTGTACTGGCTCCACCTTTTTCCCCAG<br>GGTGGGGGAGAACCATATATAAGTGCAGTAGTCTCTGTGAACATT<br>CAAGCTTCTGCCTTCTCCCTCCTGTGAGTTTGGTAAGTCACTGACT<br>GTCTATGCCTGGGAAAGGGTGGGCAGGAGATGGGGCAGTGCAGG<br>AAAAGTGGCACTATGAACCCTGCAGCCCTAGACAATTGTACTAAC<br>CTTCTTCTCTTTCCTCTCCTGACAGGTTGGTGTACAGTAGCTTCCA<br>AGTACTAAGATCTAGTGCACAGCTTAGACCAGTACTATGGCTTCC<br>TACCCTGGCCATCAGCATGCCTCTGCCTTTGACCAGGCTGCCAGA | 5 |

*Fig. 23 (cont.)*

| Name | Sequence | SEQ ID NO: |
|---|---|---|
| | TCTAGAGGCCATAGCAACAGAAGAACTGCCTTGAGACCTAGAAG<br>ACAGCAAGAAGCCACTGAAGTCAGACCTGAGCAGAAAATGCCCA<br>CCCTACTGAGGGTTTATATAGATGGTCCCCATGGGATGGGGAAAA<br>CCACCACCACCCAACTGCTGGTGGCCCTGGGTAGCAGAGATGAT<br>ATTGTCTATGTACCTGAGCCCATGACTTACTGGAGGGTGCTGGGG<br>GCTTCTGAGACAATTGCCAACATCTACACCACACAACACAGACTG<br>GACCAGGGTGAGATATCTGCTGGGGATGCTGCTGTGGTAATGAC<br>ATCTGCCCAGATAACAATGGGCATGCCTTATGCTGTGACAGATGC<br>TGTTCTGGCTCCTCATATTGGGGGGGAGGCTGGGAGCTCACATGC<br>CCCTCCCCCTGCCCTCACCATTTTCCTGGACAGACATCCCATTGCC<br>TTCATGCTGTGCTACCCTGCTGCCAGATACCTTATGGGCAGCATG<br>ACCCCCCAGGCTGTGCTGGCCTTTGTGGCCCTCATCCCCCCTACCT<br>TGCCTGGCACAAACATTGTGTTGGGGGCCCTTCCTGAGGACAGAC<br>ACATTGACAGACTGGCCAAAAGACAGAGACCTGGAGAGAGACTT<br>GACCTGGCTATGCTGGCTGCCATTAGAAGGGTTTATGGGCTGCTT<br>GCCAATACTGTGAGATATCTGCAGGGAGGAGGGTCCTGGAGAGA<br>GGATTGGGGACAGCTTTCTGGGACTGCTGTGCCTCCCAGGGTGC<br>TGAGCCCCAGAGCAATGCTGGCCCAAGACCCCATATTGGGGACA<br>CCTTATTTACCCTGTTTAGAGCCCCTGAGTTGCTGGCCCCCAATGG<br>AGACCTGTACAATGTGTTTGCCTGGGCCTTGGATGTCTTGGCCAA<br>AAGACTCAGACCCATGCATGTCTTTATCCTGGATTATGACCAATC<br>CCCTGCTGGCTGCAGAGATGCCCTGCTGCAACTTACCTCTGGGAT<br>GGTCCAGACCCATGTCACCACCCCTGGCTCCATACCCACCATCTG<br>TGACCTGGCCAGAACCTTTGCCAGAGAGATGGGGGAGGCTAACT<br>GAGCTAGCTGGCCAGACATGATAAGATACATTGATGAGTTTGGA<br>CAAACCACAACTAGAATGCAGTGAAAAAATGCTTTATTTGTGA<br>AATTTGTGATGCTATTGCTTTATTTGTAACCATTATAAGCTGCAAT<br>AAACAAGTTAACAACAACAATTGCATTCATTTTATGTTTCAGGTT<br>CAGGGGGAGGTGTGGGAGGTTTTTTAAAGCAAGTAAAACCTCTA<br>CAAATGTGGTATGGAATTGGAGCCCCACTGTGTTCATCTTACAGA<br>TGGAAATACTGACATTCAGAGGAGTTAGTTAACTTGCCTAGGTGA<br>TTCAGCTAATAAGTGCAAGAAAGATTTCAATCCAAGGTGATTTGA<br>TTCTGAAGCCTGTGCTAATCACATTACACCAAGCTACAACTTCAT<br>TTATAAATAATAAGTCAGCTTTCAAGGGCCTTTCAGGTGTCCTGC<br>ACTTCTACAAGCTGTGCCATTTAGTGAACACAAAATGAGCCTTCT<br>GATGAAGTAGTCTTTTCATTTATTTCAGATATTAGAACACTAAAAT<br>TCTTAGCTGCCAGCTGATTGAAGGCTGGGACAAAATTCAAACATG<br>CATCTACAACAATATATATCTCAATGTTAGTCTCCAAATTCTATTG<br>ACTTCAACTCAAGAGAATATAAAGAGCTAGTCTTTATACACTCTT<br>TAAGGTATGATATCATCTGGAAAGTAACAAAATTGATGCAAATTT<br>GAATGAACTTTATCATGGTGTATTTACACAATGTGTTTCTTCTCCC<br>TGCAATGTATTTCTTTCTCTAATTCCTTCCATTTGATCTTTCATACA<br>CAATCTGGTTCTGATGTATGTTTTTGGATGCACTTTTCAACTCCA<br>AAAGACAGAGCTAGTTACTTTCTTCCTGGTGCTCCAAGCACTGTA<br>TTTGTATCTGTATTCAAGCCCTTTGCAATATTGTACTGGATCATTA<br>TTTCACCTCTAGGATGGCTTCCCCAGGCAACTTGTGTTCACCCAG<br>AGACTACATTTTGTATCTTGTTGACCTTTGAACTTCCACCAGTGTC<br>TAAAAATAATATGTATGCAAAATTACTTGCTATGAGAATGTATAA<br>TTAAACAATATAAAAGGAGAAGCAAGGAGAGAAACACAGGTG<br>TGTATTTGTGTTTGTGCTTAAAAGGCAGTGTGGAAAAGGAAGA<br>AATGCCATTTATAGTGAGGAGACAAAGTTATATTACCTCTTATCT<br>GGCTTTTAAGGAGATTTGCTGAGCTAAAAATCCTATATTCATAG<br>AAAAGCCTTACCTGAGTTGCCAATACCTCAATTCTAAAATACAGC<br>ATAGCAAAACTTTAACCTCCAAATCAAGCCTCTACTTGAATCCTT<br>TTCTGAGGGATGAATAAGGCATAGGCATCAGGGGCTGTTGCCAA<br>TGTGCATTAGCTGTTTGCAGCCTCACCTTCTTTCATGGAGTTTAAG<br>ATATAGTGTATTTTCCCAAGGTTTGAACTAGCTCTTCATTTCTTTA<br>TGTTTAAATGCACTGACCTCCCACATTCCCTTTTTAGTAAAATAT<br>TCAGAAATAATTTAAATACATCATTGCAATGAAAATAAATGTTTT<br>TTATTAGGCAGAATCCAGATGCTCAAGGCCCTTCATAATATCCCC | |

*Fig. 23 (cont.)*

| Name | Sequence | SEQ ID NO: |
|---|---|---|
| | CAGTTTAGTAGTTGGACTTAGGGAACAAAGGAACCTTTAATAGA AATTGGACAGCAAGAAAGCTCTAGCTTTAGAAGAACTCATCAAG AAGTCTGTAGAAGGCAATTCTCTGGGAGTCAGGGGCTGCAATGC CATAGAGCACTAGGAACCTGTCTGCCCACTCTCCCCCTAGCTCTT CTGCTATGTCCCTGGTTGCTAGGGCAATGTCCTGGTACCTGTCAG CCACTCCCAGCCTGCCACAGTCTATGAAGCCAGAGAACCTTCCAT TTTCAACCATGATGTTGGGAAGGCAGGCATCCCCATGAGTCACCA CTAGGTCCTCACCATCTGGCATGGATGCCTTGAGCCTGGCAAATA GTTCAGCAGGGGCCAGGCCCTGGTGTTCTTCATCCAAGTCATCTT GGTCCACCAGGCCAGCCTCCATCCTGGTTCTGGCCCTCTCTATCCT GTGCTTGGCCTGGTGGTCAAAGGGGCAGGTGGCTGGGTCAAGGG TGTGGAGTCTTCTCATGGCATCAGCCATGATTGACACTTTCTCAG CTGGAGCTAGGTGAGAGGAAAGGAGGTCCTGCCCAGGCACCTCA CCTAGTAGGAGCCAGTCCCTTCCAGCTTCTGTGACCACATCAAGG ACAGCTGCACAGGGGACCCCAGTTGTTGCCAACCAGGAGAGTCT GGCAGCCTCATCCTGGAGCTCATTGAGAGCCCCACTGAGGTCTGT CTTTACAAAAAGGACTGGCCTGCCTTGGGCTGAAAGTCTGAAAAC TGCTGCATCAGAGCAACCAATGGTCTGCTGTGCCCAGTCATAGCC AAACAGTCTCTCAACCCAGGCAGCTGGAGAACCTGCATGTAGGC CATCTTGTTCAATCATGATGGCTCCTCCTGTCAGGAGAGGAAAGA GAAGAAGGTTAGTACAATTGCTATAGTGAGTTGTATTATACTATG CTTATGATTAATTGTCAAACTAGGGCTGCAGGGTTCATAGTGCCA CTTTTCCTGCACTGCCCCATCTCCTGCCCACCCTTTCCCAGGCATA GACAGTCAGTGACTTACCAAACTCACAGGAGGGAGAAGGCAGAA GCTTTTTGCAAAAGCCTAGGCCTCCAAAAAAGCCTCCTCACTACT TCTGGAATAGCTCAGAGGCCCAGGGGGCCTGGGCCTCTGCATAA ATAAAAAAAATTAGTCAGCCTGGGGCTGGGGTGGGGGCAGGGGT GGGGGGCCAACTGGGCAGGGGTGGGGGGCCACTAGTGGGACTAT GGTTGCTGACTAATTGAGATGCATGCTTTGCATACTTCTGCCTGCT GGGGAGCCTGGGGACTTTCCACACCTGGTTGCTGACTAATTGAGA TGCATGCTTTGCATACTTCTGCCTGCTGGGGAGCCTGGGGACTTT CCACACCCTAACTGACACACATTCCACAGCTGGTTCTTTCAGCCT CAGAAGGTACCTAACCAAGTTCCTCTTTCAGAGGTTATTTCAGGC CCTGCAGGAATTCAGTCAATATGTTCACCCCAAAAAAGCTGTTTG TTAACTTGTCAACCTCATTCTAAAATGTATATAGAAGCCCAAAAG ACAATAACAAAAATATTCTTGTAGAACAAAATGGGAAAGAATGT TCCACTAAATATCAAGATTTAGAGCAAAGCATGAGATGTGTGGG GATAGACAGTGAGGCTGATAAAATAGAGTAGAGCTCAGAAACAG ACCCATTGATATATGTAAGTGACCTATGAAAAAAATATGGCATTT TACAATGGGAAAATGATGGTCTTTTTCTTTTTTAGAAAAACAGGG AAATATATTTATATGTAAAAAATAAAAGGGAACCCATATGTCATA CCATACACACAAAAAAATTCCAGTGAATTATAAGTCTAAATGGA GAAGGCAAAACTTTAAATCTTTTAGAAAATAATATAGAAGCATG CCATCAAGACTTCAGTGTAGAGAAAAATTTCTTATGACTCAAAGT CCTAACCACAAAGAAAAGATTGTTAATTAGATTGCATGAATATTA AGACTTATTTTTAAAATTAAAAAACCATTAAGAAAAGTCAGGCCA TAGAATGACAGAAAATATTTGCAACACCCCAGTAAAGAGAATTG TAATATGCAGATTATAAAAAGAAGTCTTACAAATCAGTAAAAAA TAAAACTAGACAAAAATTTGAACAGATGAAAGAGAAACTCTAAA TAATCATTACACATGAGAAACTCAATCTCAGAAATCAGAGAACT ATCATTGCATATACACTAAATTAGAGAAATATTAAAAGGCTAAGT AACATCTGTGGCTTAATTAAGTTATCCTAGGAAACCTTAAAACCT TTAAAAGCCTTATATATTCTTTTTTTTCTTATAAAACTTAAAACCT TAGAGGCTATTTAAGTTGCTGATTTATATTAATTTTATTGTTCAAA CATGAGAGCTTAGTACATGAAACATGAGAGCTTAGTACATTAGCC ATGAGAGCTTAGTACATTAGCCATGAGGGTTTAGTTCATTAAACA TGAGAGCTTAGTACATTAAACATGAGAGCTTAGTACATACTATCA ACAGGTTGAACTGCTGATT | |

*Fig. 23 (cont.)*

| Name | Sequence | SEQ ID NO: |
|---|---|---|
| Complete AFP-SR39 plasmid: pCpGfree-vitroNmcs-CpGfreeAFP-prom/enh-CpGfreeSR39 nucleic acid sequence | AATTCAGTCAATATGTTCACCCCAAAAAAGCTGTTTGTTAACTTG TCAACCTCATTCTAAAATGTATATAGAAGCCCAAAAGACAATAAC AAAAATATTCTTGTAGAACAAAATGGGAAAGAATGTTCCACTAA ATATCAAGATTTAGAGCAAAGCATGAGATGTGTGGGGATAGACA GTGAGGCTGATAAAATAGAGTAGAGCTCAGAAACAGACCCATTG ATATATGTAAGTGACCTATGAAAAAAATATGGCATTTTACAATGG GAAAATGATGGTCTTTTTCTTTTTTAGAAAAACAGGGAAATATAT TTATATGTAAAAAATAAAAGGGAACCCATATGTCATACCATACAC ACAAAAAAATTCCAGTGAATTATAAGTCTAAATGGAGAAGGCAA AACTTTAAATCTTTTAGAAAATAATATAGAAGCATGCCATCAAGA CTTCAGTGTAGAGAAAAATTTCTTATGACTCAAAGTCCTAACCAC AAAGAAAAGATTGTTAATTAGATTGCATGAATATTAAGACTTATT TTTAAAATTAAAAAACCATTAAGAAAAGTCAGGCCATAGAATGA CAGAAAATATTTGCAACACCCCAGTAAAGAGAATTGTAATATGC AGATTATAAAAGAAGTCTTACAAATCAGTAAAAAATAAAACTA GACAAAATTTGAACAGATGAAAGAGAAACTCTAAATAATCATT ACACATGAGAAACTCAATCTCAGAAATCAGAGAACTATCATTGC ATATACACTAAATTAGAGAAATATTAAAAGGCTAAGTAACATCT GTGGCTTAATTAAGTTATCCTAGGAAACCTTAAAACCTTTAAAAG CCTTATATATTCTTTTTTTTCTTATAAAACTTAAAACCTTAGAGGC TATTTAAGTTGCTGATTTATATTAATTTTATTGTTCAAACATGAGA GCTTAGTACATGAAACATGAGAGCTTAGTACATTAGCCATGAGA GCTTAGTACATTAGCCATGAGGGTTTAGTTCATTAAACATGAGAG CTTAGTACATTAAACATGAGAGCTTAGTACATACTATCAACAGGT TGAACTGCTGATTTTAATTAAAATTATCTCTAAGGCATGTGAACT GGCTGTCTTGGTTTTCATCTGTACTTCATCTGCTACCTCTGTGACC TGAAACATATTTATAATTCCATTAAGCTGTGCATATGATAGATTT ATCATATGTATTTTCCTTAAAGGATTTTGTAAGAACTAATTGAAT TGATACCTGTAAAGTCTTTATCACACTACCCAATAAATAATAAAT CTCTTTGTTCAGCTCTCTGTTTCTATAAATATGTACCAGTTTTATT GTTTTTAGTGGTAGTGATTTTATTCTCTTTCTATATATATACACAC ACATGTGTGCATTCATAAATATATACAATTTTTATGAATAAAAAA TTATTAGCAATCAATATTGAAAACCACTGATTTTTGTTTATGTGAG CAAACAGCAGATTAAAAGGAATTTCAATTGCCTGCAGGCTTAGA AATATGGGGGTAGGGGTGGTGGTGGTAATTCTGTTTTCTCCCCAT AGGTGAGATAAGCATTGGGTTAAATGTGCTTTCTCTCTCTCCCTCT CCTTTCTTAAGAATTAAGGGACAGACTATGGGCTGGAGGACTTTG AGGATGTCTGTCTCATAACACTTGGGTTGTATCTGTTCTATGGGG CTTGTTTTAAGCTTGGCAACTTGCAACAGGGTTCACTGACTTTCTC CCCAGGCCCAAGGTACTGTCCTCTTTTCATATCTGTTTGGGGCCT CTGGGGCTTGAATATCTGAGAAAATATAAACATTTCAATAATGTT CTGTGGTGAGATGAGTATGAGAGATGTGTCATTCATTTGTATCAA TGAATGAATGAGGACAATTAGTGTATAAATCCTTAGTACAACAAT CTGAGGGTAGGGGTGGTACTATTCAATTTCTATTTATAAAGATAC TTATTTCTATTTATTTATGCTTGTGACAAATGTTTTGTTTGGGACC ACAGGAATCACAAAGATGAGTCTTTGAATTTAAGAAGTTAATGGT CCAGGAATAATTACATAGCTTACAAATGACTATGATATACCATCA AACAAGAGGTTCCATGAGAAAATAATCTGAAAGGTTTAATAAGT TGTCAAAGGTGAGAGGGCTCTTCTCTAGCTAGAGACTAATCAGAA ATACATTCAGGGATAATTATTTGAATAGACCTTAAGGGTTGGGTA CATTTGTTCAAGCATTGATGGAGAAGGAGAGTGAATATTTGAAA ACATTTTCAACTAACCAACCACCCAATCCAACAAACAAAAAATG AAAAGAATCTCAGAAACAGTGAGATAAGAGAAGGAATTTTCTCA CAACCCACATGTATAGCTCAACTGCTCTGAAGAAGTATATATCTA ATATTTAACACTAACATCATGCTAATAATGATAATAATTACTGTC ATTTTTTAATGTCTATAAGTACCAGGCATTTAGAAGATATTATTCC ATTTATATATCAAAATAAACTTGAGGGGATAGATCATTTTCATGA TATATGAGAAAAATTAAAAATCAGATTGAATTATTTGCCTGTCAT ACAGCTAATAATTGACCATAAGACAATTAGATTTAAATTAGTTTT GAATCTTTCTAATACCAAAGTTCAGTTTACTGTTCCATGTTGCTTC | 6 |

*Fig. 23 (cont.)*

| Name | Sequence | SEQ ID NO: |
|---|---|---|
| | TGAGTGGCTTCACAGACTTATGAAAAAGTAAATGGAATCAGAAT<br>TACATCAATGCAAAAGCATTGCTGTGAACTCTGTACTTAGGACTA<br>AACTTTGAGCAATAACACATATAGATTGAGGATTGTTTGCTGTTA<br>GTATACAAACTCTGGTTCAAAGCTCCTCTTTATTGCTTGTCTTGGA<br>AAATTTGCTGTTCTTCATGGTTTCTCTTTTCACTGCTATCTATTTTT<br>CTCAACCACTCACATGGCTACAATAACTGTCTGCAAGCTTATGAT<br>TCCCAAATGTCTATCTCTAGCCTCAATCTTGTTCCAGAAGATAAA<br>AAGTAGTATTCAAATGCACATCAACATCTCCACTTGGAGGGCTTA<br>AAGATGTTTCAACATACAAACTGGGGAGTTTTGCCTGGAATGTTT<br>CCTAAAATGTGTCCTGTAGCACATAGGGTCCTCTTGTTCCTTAAA<br>ATCTAATTACTTTTAGCCCAGTGCTCATCCCACCTATGGGGAGAT<br>GAGAGTGAAAAGGGAGCCTGATTAATAATTACACTAAGTCAATA<br>GGCATAGAGCCAGGACTGTTTGGGTAAACTGGTCACTTTATCTTA<br>AACTAAATATATCCAAAACTGAACATGTACTTAGTTACTAAGTCT<br>TTGACTTTATCTCATTCATACCACTCAGCTTTATCCAGGCCACTAG<br>AGTTTGAGGAGAATATTTGTTATATTTGCAAAATAAAATAAGTTT<br>GCAAGTTTTTTTTTTCTGCCCCAAAGAGCTCTGTGTCCTTGAACAT<br>AAAATACAAATAACTGCTATGCTGTTAATTATTGACAAATGTCCC<br>ATTTTCAACCTAAGGAAATACCATAAAGTAACAGATATACCAAC<br>AAAAGGTTACTAGTTAACAGGCATTGCCTGAAAAGAGTATAAAA<br>GAATTTCAGCATGATTTTCCATATTGTGCTTCCACCACTGCCAATA<br>ACAAAATAACTAGCAACATGGCTTCCTACCCTGGCCATCAGCATG<br>CCTCTGCCTTTGACCAGGCTGCCAGATCTAGAGGCCATAGCAACA<br>GAAGAACTGCCTTGAGACCTAGAAGACAGCAAGAAGCCACTGAA<br>GTCAGACCTGAGCAGAAAATGCCCACCCTACTGAGGGTTTATATA<br>GATGGTCCCCATGGGATGGGGAAAACCACCACCACCCAACTGCT<br>GGTGGCCCTGGGTAGCAGAGATGATATTGTCTATGTACCTGAGCC<br>CATGACTTACTGGAGGGTGCTGGGGGCTTCTGAGACAATTGCCAA<br>CATCTACACCACACAACACAGACTGGACCAGGGTGAGATATCTG<br>CTGGGGATGCTGCTGTGGTAATGACATCTGCCCAGATAACAATGG<br>GCATGCCTTATGCTGTGACAGATGCTGTTCTGGCTCCTCATATTGG<br>GGGGGAGGCTGGGAGCTCACATGCCCCTCCCCCTGCCCTCACCAT<br>TTTCCTGGACAGACATCCCATTGCCTTCATGCTGTGCTACCCTGCT<br>GCCAGATACCTTATGGGCAGCATGACCCCCCAGGCTGTGCTGGCC<br>TTTGTGGCCCTCATCCCCCCTACCTTGCCTGGCACAAACATTGTGT<br>TGGGGGCCCTTCCTGAGGACAGACACATTGACAGACTGGCCAAA<br>AGACAGAGACCTGGAGAGAGACTTGACCTGGCTATGCTGGCTGC<br>CATTAGAAGGGTTTATGGGCTGCTTGCCAATACTGTGAGATATCT<br>GCAGGGAGGAGGGTCCTGGAGAGAGGATTGGGGACAGCTTTCTG<br>GGACTGCTGTGCCTCCCCAGGGTGCTGAGCCCCAGAGCAATGCTG<br>GCCCAAGACCCCATATTGGGGACACCTTATTTACCCTGTTTAGAG<br>CCCCTGAGTTGCTGGCCCCAATGGAGACCTGTACAATGTGTTTG<br>CCTGGGCCTTGGATGTCTTGGCCAAAAGACTCAGACCCATGCATG<br>TCTTTATCCTGGATTATGACCAATCCCCTGCTGGCTGCAGAGATG<br>CCCTGCTGCAACTTACCTCTGGGATGGTCCAGACCCATGTCACCA<br>CCCCTGGCTCCATACCCACCATCTGTGACCTGGCCAGAACCTTTG<br>CCAGAGAGATGGGGGAGGCTAACTGAGTGCACAGGGCCCACCAT<br>GGAGCTAGCTGGCCAGACATGATAAGATACATTGATGAGTTTGG<br>ACAAACCACAACTAGAATGCAGTGAAAAAATGCTTTATTTGTG<br>AAATTTGTGATGCTATTGCTTTATTTGTAACCATTATAAGCTGCAA<br>TAAACAAGTTAACAACAACAATTGCATTCATTTTATGTTTCAGGT<br>TCAGGGGAGGTGTGGGAGGTTTTTTAAAGCAAGTAAAACCTCT<br>ACAAATGTGGTATGGAATTGGAGCCCCACTGTGTTCATCTTACAG<br>ATGGAAATACTGACATTCAGAGGAGTTAGTTAACTTGCCTAGGTG<br>ATTCAGCTAATAAGTGCAAGAAAGATTTCAATCCAAGGTGATTTG<br>ATTCTGAAGCCTGTGCTAATCACATTACACCAAGCTACAACTTCA<br>TTTATAAATAATAAGTCAGCTTTCAAGGGCCTTTCAGGTGTCCTG<br>CACTTCTACAAGCTGTGCCATTTAGTGAACACAAAATGAGCCTTC<br>TGATGAAGTAGTCTTTTCATTATTTCAGATATTAGAACACTAAA<br>TTCTTAGCTGCCAGCTGATTGAAGGCTGGGACAAAATTCAAACAT | |

*Fig. 23 (cont.)*

| Name | Sequence | SEQ ID NO: |
|---|---|---|
| | GCATCTACAACAATATATATCTCAATGTTAGTCTCCAAATTCTATT GACTTCAACTCAAGAGAATATAAAGAGCTAGTCTTTATACACTCT TTAAGGTATGATATCATCTGGAAAGTAACAAAATTGATGCAAATT TGAATGAACTTTATCATGGTGTATTTACACAATGTGTTTCTTCTCC CTGCAATGTATTTCTTTCTCTAATTCCTTCCATTTGATCTTTCATAC ACAATCTGGTTCTGATGTATGTTTTTTGGATGCACTTTTCAACTCC AAAAGACAGAGCTAGTTACTTTCTTCCTGGTGCTCCAAGCACTGT ATTTGTATCTGTATTCAAGCCCTTTGCAATATTGTACTGGATCATT ATTTCACCTCTAGGATGGCTTCCCCAGGCAACTTGTGTTCACCCA GAGACTACATTTTGTATCTTGTTGACCTTTGAACTTCCACCAGTGT CTAAAAATAATATGTATGCAAAATTACTTGCTATGAGAATGTATA ATTAAACAATATAAAAAGGAGAAGCAAGGAGAGAAACACAGGT GTGTATTTGTGTTTGTGTGCTTAAAAGGCAGTGTGGAAAAGGAAG AAATGCCATTTATAGTGAGGAGACAAAGTTATATTACCTCTTATC TGGCTTTTAAGGAGATTTTGCTGAGCTAAAAATCCTATATTCATA GAAAAGCCTTACCTGAGTTGCCAATACCTCAATTCTAAAATACAG CATAGCAAAACTTTAACCTCCAAATCAAGCCTCTACTTGAATCCT TTTCTGAGGGATGAATAAGGCATAGGCATCAGGGGCTGTTGCCA ATGTGCATTAGCTGTTTGCAGCCTCACCTTCTTTCATGGAGTTTAA GATATAGTGTATTTTCCCAAGGTTTGAACTAGCTCTTCATTTCTTT ATGTTTTAAATGCACTGACCTCCCACATTCCCTTTTTAGTAAAATA TTCAGAAATAATTTAAATACATCATTGCAATGAAAATAAATGTTT TTTATTAGGCAGAATCCAGATGCTCAAGGCCCTTCATAATATCCC CCAGTTTAGTAGTTGGACTTAGGGAACAAAGGAACCTTTAATAGA AATTGGACAGCAAGAAAGCTCTAGCTTTAGAAGAACTCATCAAG AAGTCTGTAGAAGGCAATTCTCTGGGAGTCAGGGGCTGCAATGC CATAGAGCACTAGGAACCTGTCTGCCCACTCTCCCCCTAGCTCTT CTGCTATGTCCTGGTTGCTAGGGCAATGTCCTGGTACCTGTCAG CCACTCCCAGCCTGCCACAGTCTATGAAGCCAGAGAACCTTCCAT TTTCAACCATGATGTTGGGAAGGCAGGCATCCCCATGAGTCACCA CTAGGTCCTCACCATCTGGCATGGATGCCTTGAGCCTGGCAAATA GTTCAGCAGGGGCCAGGCCCTGGTGTTCTTCATCCAAGTCATCTT GGTCCACCAGGCCAGCCTCCATCCTGGTTCTGGCCCTCTCTATCCT GTGCTTGGCCTGGTGGTCAAAGGGGCAGGTGGCTGGGTCAAGGG TGTGGAGTCTTCTCATGGCATCAGCCATGATTGACACTTTCTCAG CTGGAGCTAGGTGAGAGGAAAGGAGGTCCTGCCCAGGCACCTCA CCTAGTAGGAGCCAGTCCCTTCCAGCTTCTGTGACCACATCAAGG ACAGCTGCACAGGGGACCCCAGTTGTTGCCAACCAGGAGAGTCT GGCAGCCTCATCCTGGAGCTCATTGAGAGCCCCACTGAGGTCTGT CTTTACAAAAAGGACTGGCCTGCCTTGGGCTGAAAGTCTGAAAAC TGCTGCATCAGAGCAACCAATGGTCTGCTGTGCCCAGTCATAGCC AAACAGTCTCTCAACCCAGGCAGCTGGAGAACCTGCATGTAGGC CATCTTGTTCAATCATGATGGCTCCTCCTGTCAGGAGAGGAAAGA GAAGAAGGTTAGTACAATTGCTATAGTGAGTTGTATTATACTATG CTTATGATTAATTGTCAAACTAGGGCTGCAGGGTTCATAGTGCCA CTTTTCCTGCACTGCCCCATCTCCTGCCCACCCTTTCCCAGGCATA GACAGTCAGTGACTTACCAAACTCACAGGAGGGAGAAGGCAGAA GCTTTTTGCAAAAGCCTAGGCCTCCAAAAAAGCCTCCTCACTACT TCTGGAATAGCTCAGAGGCCCAGGGGGCCTGGGCCTCTGCATAA ATAAAAAAATTAGTCAGCCTGGGGCTGGGGTGGGGGCAGGGGT GGGGGGCCAACTGGGCAGGGGTGGGGGGCCACTAGTGGGACTAT GGTTGCTGACTAATTGAGATGCATGCTTTGCATACTTCTGCCTGCT GGGGAGCCTGGGGACTTTCCACACCTGGTTGCTGACTAATTGAGA TGCATGCTTTGCATACTTCTGCCTGCTGGGGAGCCTGGGGACTTT CCACACCCTAACTGACACACATTCCACAGCTGGTTCTTTCAGCCT CAGAAGGTACCTAACCAAGTTCCTCTTTCAGAGGTTATTTCAGGC CCTGCAGG | |

*Fig. 23 (cont.)*

TRANSCRIPTIONALLY TARGETED AND CPG-FREE PLASMID FOR THERANOSTIC GENE THERAPY

FEDERALLY SPONSORED RESEARCH OR DEVELOPMENT

This invention was made with government support under R01EB022148 awarded by the National Institutes of Health (NIH). The government has certain rights in the invention.

BACKGROUND

Hepatocellular carcinoma (HCC) develops predominantly in the inflammatory environment of a cirrhotic liver caused by hepatitis infection, toxin exposure, or liver disease. El-Serag, H. B. and Rudolph, K. L., 2007. Therefore, a highly targeted anti-cancer approach is necessary to achieve clinical efficacy without causing toxicity and liver failure. Nucleic acid therapeutics can be designed for selective expression in cancer cells using cancer-specific promoters for transcriptional targeting, but safe and effective nucleic acid delivery remains challenging. Biodegradable poly(beta-amino) ester (PBAE) nanoparticles have been developed for biomaterial-based selective transfection of HCC cells over healthy hepatocytes. Zamboni et al., 2017.

Further, with an estimated incidence of over 1 million cases per year and an estimated mortality of 307,000 men per year, prostate cancer is the most common cancer in men and one of the most prevalent cancers worldwide. In the United States alone, there are well over 200 thousand new cases diagnosed annually. Owing in part to serum diagnostic tests for expression of the prostate-specific antigen (PSA) in developing prostate cancer, with proper diagnosis and treatment, the 5-year survival is nearly 99%. Therapy for locally advanced disease, however, remains contentious and an increasing number of disparate options are available.

SUMMARY

In some aspects, the presently disclosed subject matter provides a nucleic acid molecule comprising a nucleic acid sequence encoding a mutant thymidine kinase (TK) protein operatively linked to an alpha-fetoprotein (AFP) gene promoter. In particular aspects, the nucleic acid sequence encodes a TK mutant protein comprising the amino acid sequence of SEQ ID NO: 1. In certain aspects, the nucleic acid sequence encoding a mutant TK protein lacks CpG dinucleotides. In more certain aspects, the AFP gene promoter lacks CpG dinucleotides. In yet more certain aspects, the AFP gene promoter comprises the nucleic acid sequence of SEQ ID NO: 3.

In other aspects, the presently disclosed subject matter provides a nucleic acid molecule comprising a nucleic acid sequence encoding a mutant thymidine kinase (TK) protein operatively liked to a non-native promoter, wherein the nucleic acid sequence lacks CpG dinucleotides. In particular aspects, the nucleic acid sequence encodes a TK mutant protein comprising the amino acid sequence of SEQ ID NO: 1. In certain aspects, the nucleic acid sequence encoding a mutant TK protein lacks CpG dinucleotides. In more certain embodiments, the non-native promoter comprises a mouse CMV promoter and human EF1 enhancer.

In particular aspects, the nucleic acid molecule is plasmid DNA.

In other aspects, the presently disclosed subject matter provides an isolated nucleic acid sequence comprising an alpha-fetoprotein (AFP) gene promoter which lacks CpG dinucleotides. In particular aspects, the isolated nucleic acid sequence comprises SEQ ID NO: 3.

In some aspects, the presently disclosed subject matter provides a composition comprising the aforementioned nucleic acid molecules and poly(beta-amino) ester (PBAE) nanoparticles for delivering transcriptionally-targeted "theranostic" nucleic acids with a high degree of selectivity toward alpha fetoprotein (AFP)-producing HCC cells or prostate cancer cells.

In particular aspects, the presently disclosed subject matter provides a composition comprising a poly(beta-amino ester) (PBAE) of formula (I):

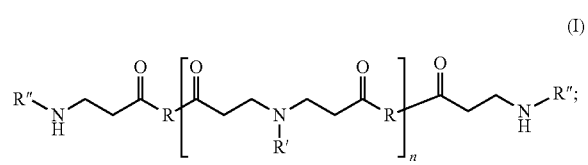

and a DNA plasmid encoding SR39 thymidine kinase; wherein: n is an integer from 1 to 10,000; each R is independently selected from the group consisting of:

(B3)

(B4)

(B5) ; and

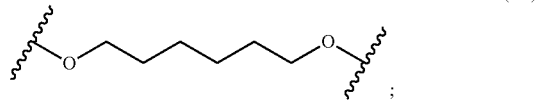
(B6) ;

each R' is independently selected from the group consisting of:

(S3)

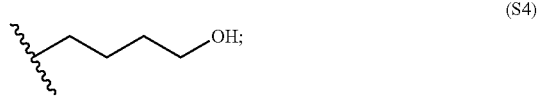
(S4)

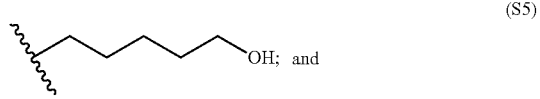
(S5) and

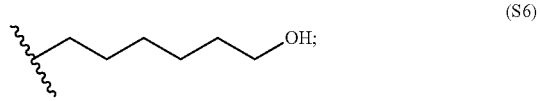
(S6)

and each R" is independently selected from the group consisting of:

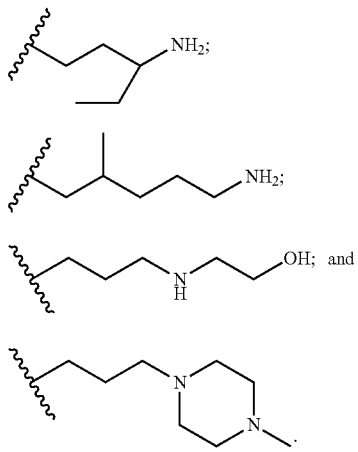

In other aspects, the presently disclosed subject matter provides a pharmaceutical formulation comprising the above-described nucleic acid molecule, a poly(beta-amino ester) (PBAE) of formula (I), and a pharmaceutically acceptable carrier. In certain aspects, the pharmaceutical formulation, further comprises one or more therapeutic agents. In more certain aspects, the one or more therapeutic agents is ganciclovir (GCV) or valganciclovir. In certain aspects, the pharmaceutical formulation further comprises one or more imaging agents. In more certain aspects, the one or more imaging agents is 9-(4-(18)F-fluoro-3-[hydroxymethyl] butyl) guanine ((18)F-FHBG).

In other aspects, the pharmaceutical formulation further comprises a nanoparticle or microparticle of the composition of formula (I).

In yet other aspects, the presently disclosed subject matter provides a method for treating or diagnosing a cancer, the method comprising administering a composition of formula (I) or a formulation thereof to a subject in need of treatment thereof. In particular aspects, the cancer is selected from the group consisting of hepatocellular carcinoma (HCC) and prostate cancer. In certain aspects, the method further comprises administering to the subject one or more therapeutic agents simultaneously or sequentially with the composition of formula (I) or a formulation thereof. In more certain aspects, the one or more therapeutic agents is ganciclovir (GCV) or valganciclovir. In other aspects, the method further comprises administering to the subject one or more imaging agents simultaneously or sequentially with the composition of formula (I) or a formulation thereof. In more certain aspects, the one or more imaging agents is 9-(4-(18) F-fluoro-3-[hydroxymethyl]butyl) guanine ((18)F-FHBG). In certain aspects, the method further comprises taking an image, which in more certain aspects, is a positron emission tomography (PET) image.

In other aspects, the presently disclosed subject matter provides a kit comprising the composition of formula (I). In certain aspects, the kit further comprises one or more therapeutic agents. In more certain aspects, the one or more therapeutic agents is ganciclovir (GCV) or valganciclovir. In certain aspects, the kit further comprises one or more imaging agents. In more certain aspects, the one or more imaging agents is 9-(4-(18)F-fluoro-3-[hydroxymethyl] butyl) guanine ((18)F-FHBG). In yet other aspects, the kit further comprises one of more of multiple dosage units of the composition, a pharmaceutically acceptable carrier, a device for administration of the composition, instructions for use, and combinations thereof.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1:
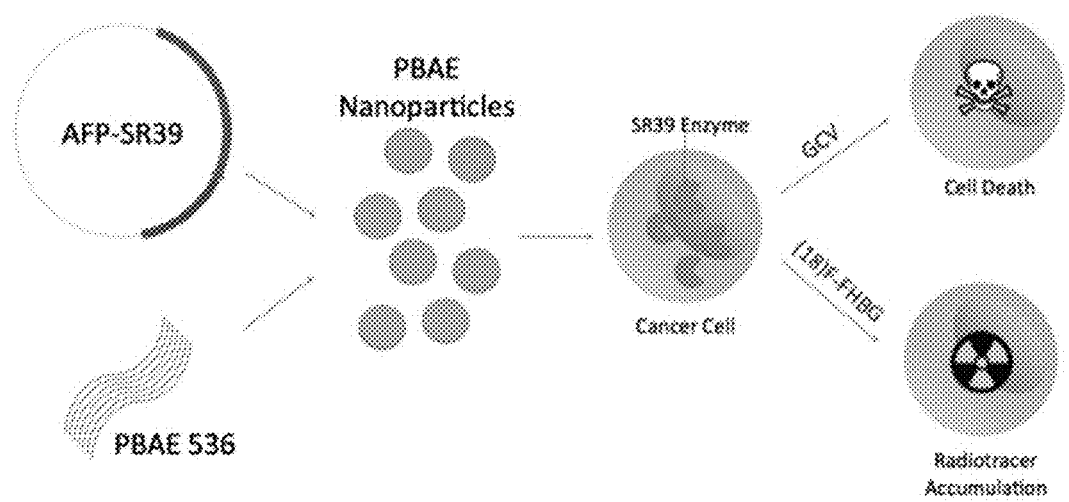
Figure 2A:
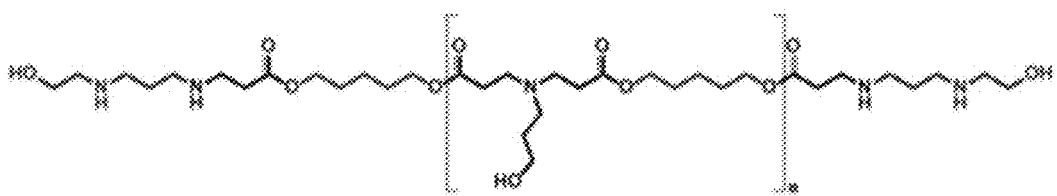
Figure 2B:
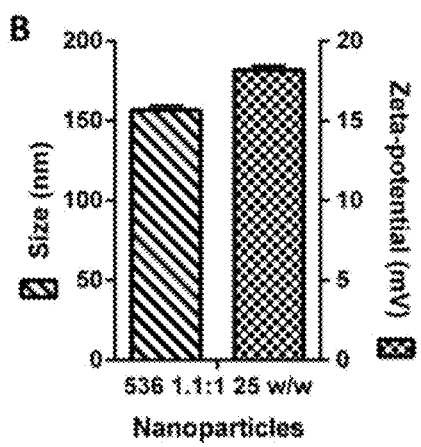
Figure 2C:
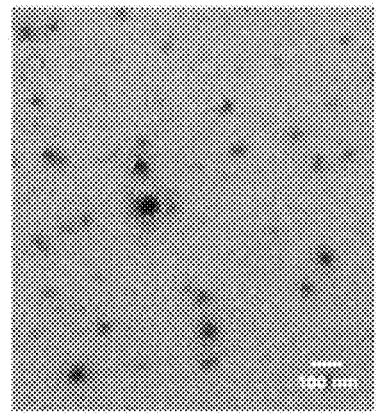
Figure 2D:
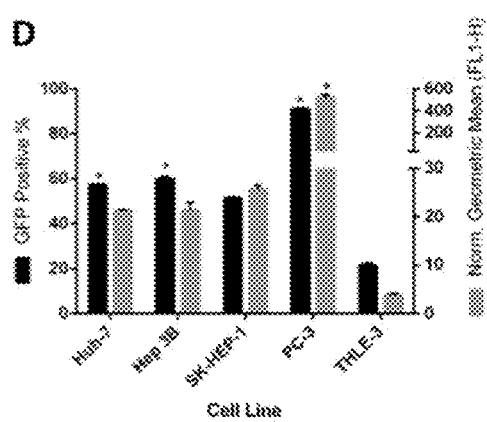
Figure 2E:
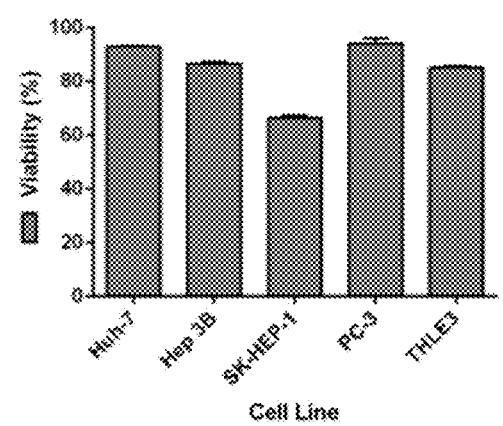
Figure 3A:
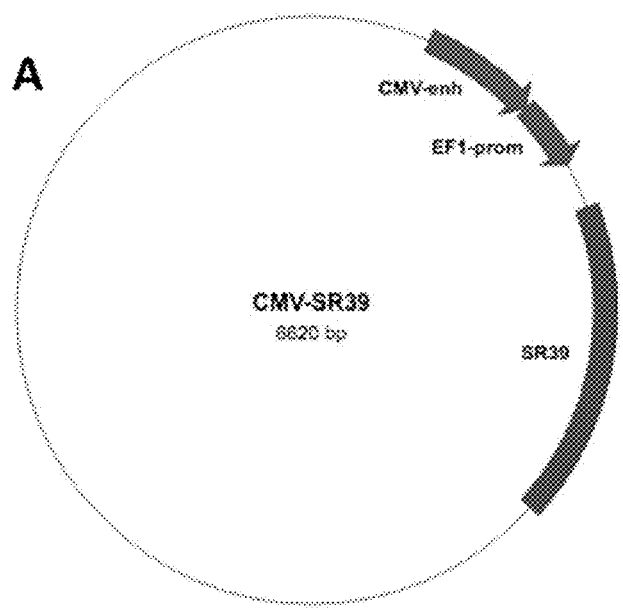
Figure 3B:
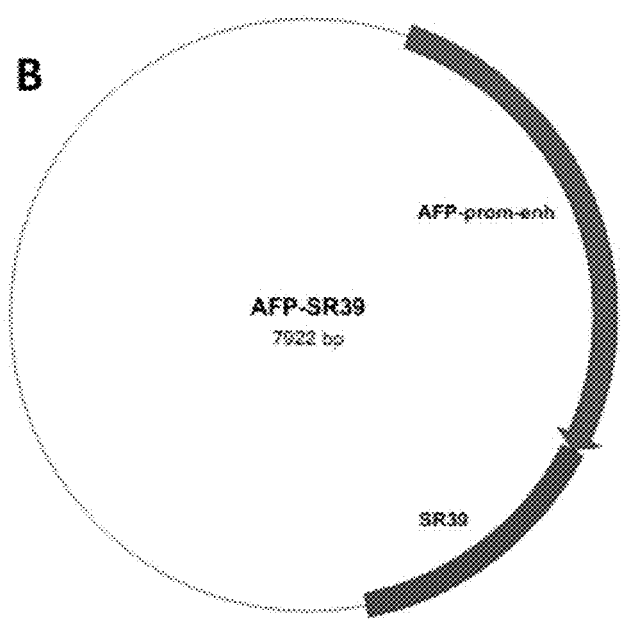
Figure 4A:
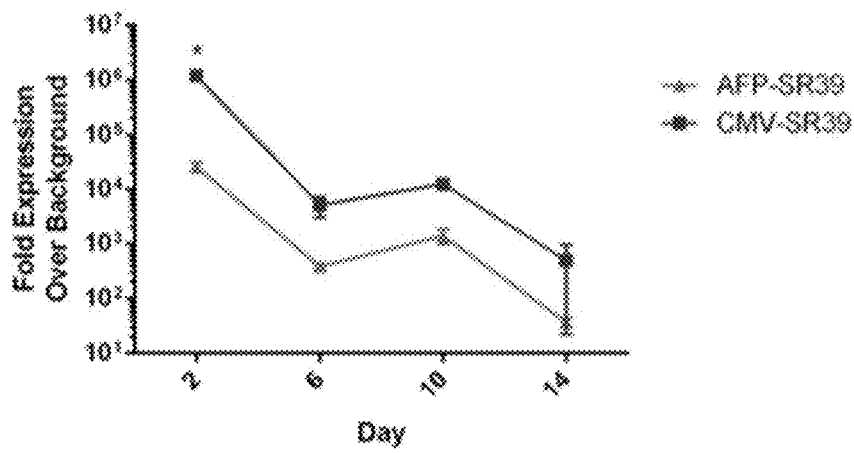
Figure 4B:
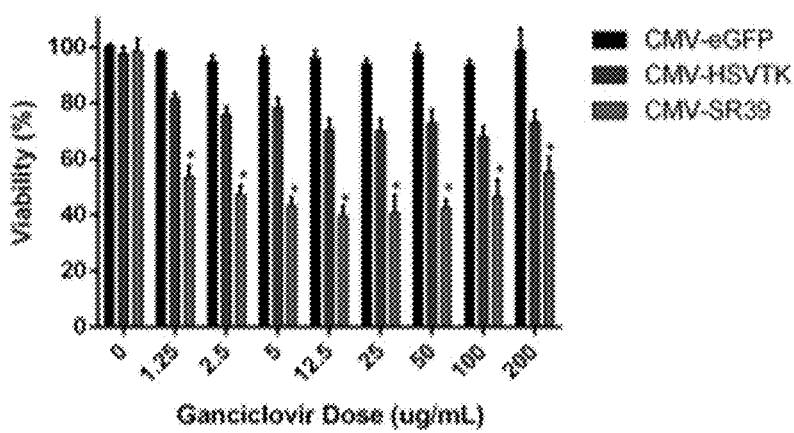
Figure 5:
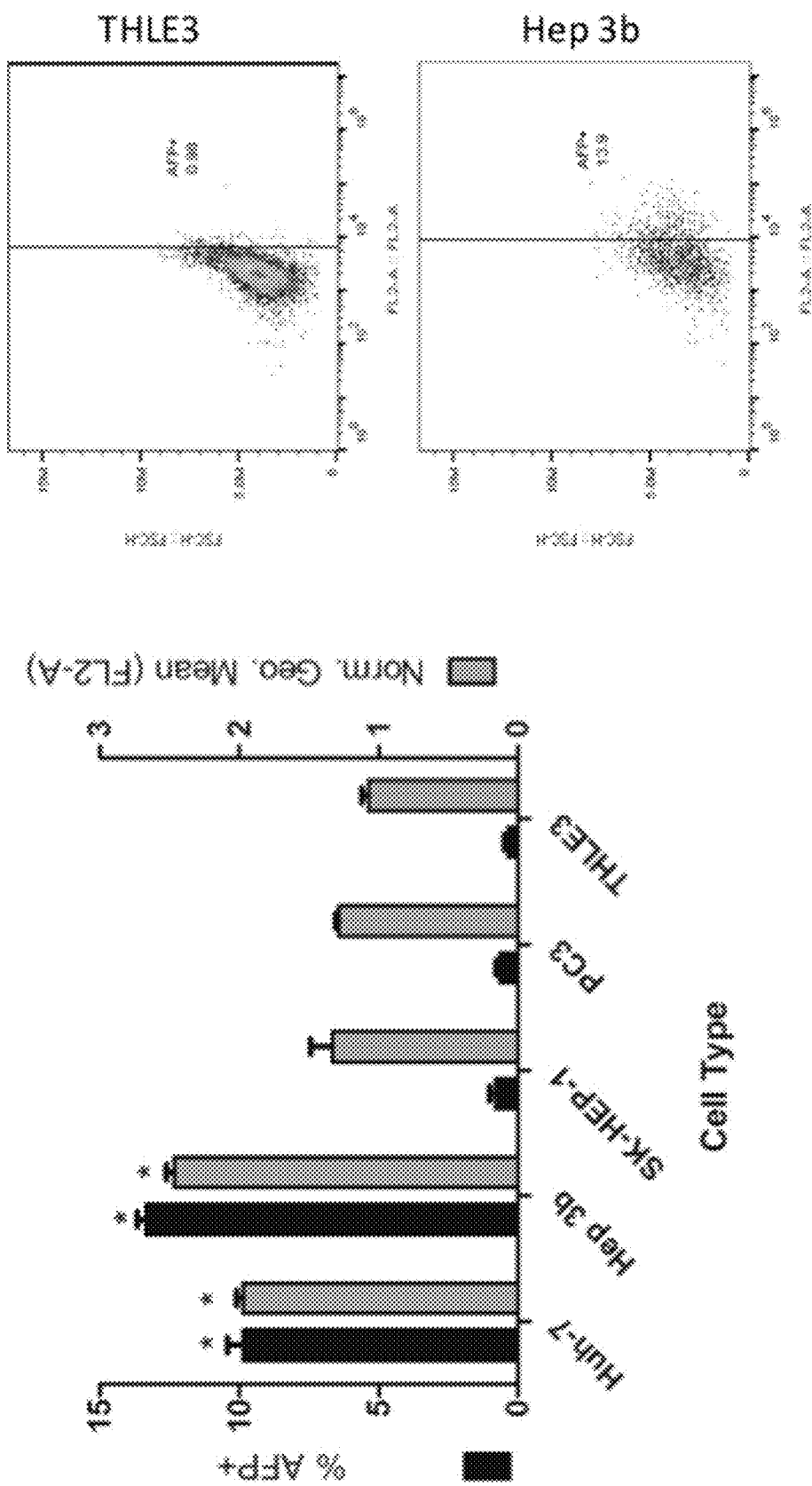
Figure 6A:
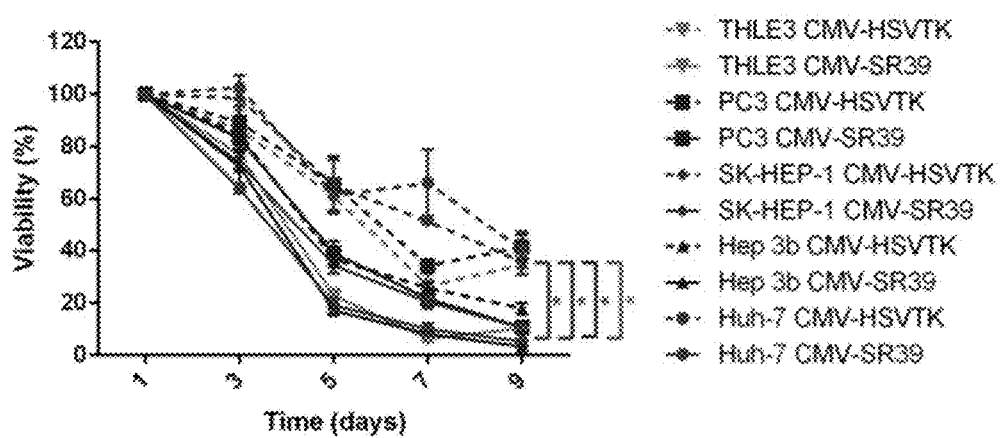
Figure 6B:
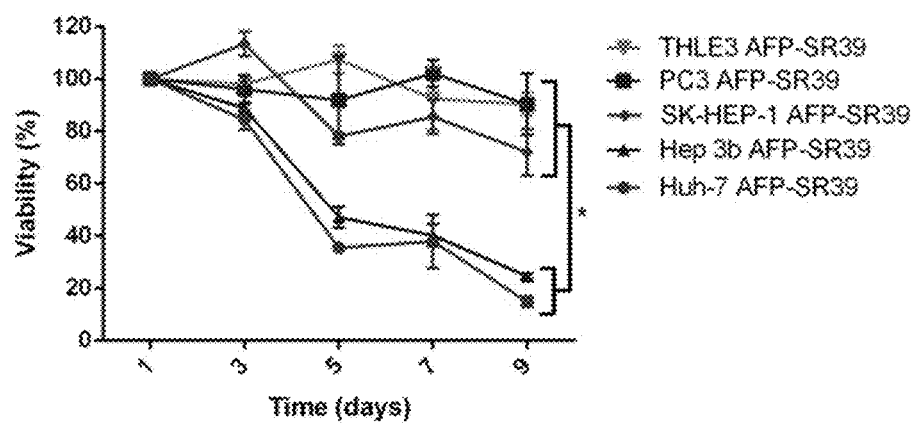
Figure 7A:
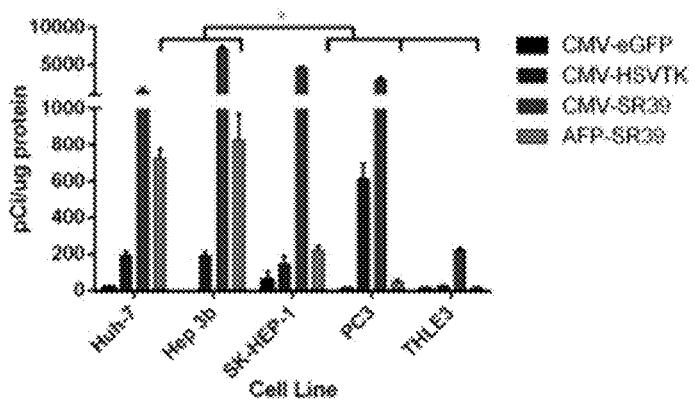
Figure 7B:
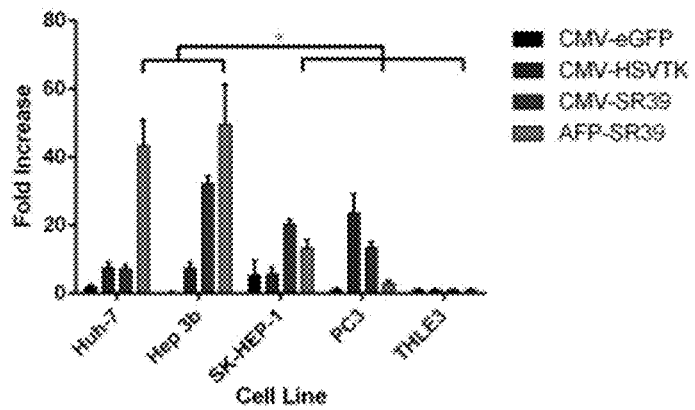
Figure 7C:
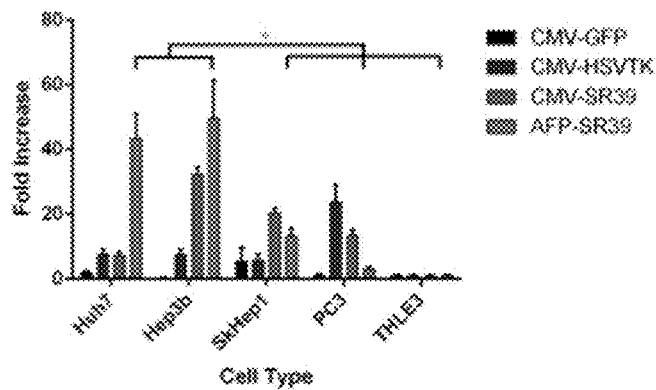
Figure 8:
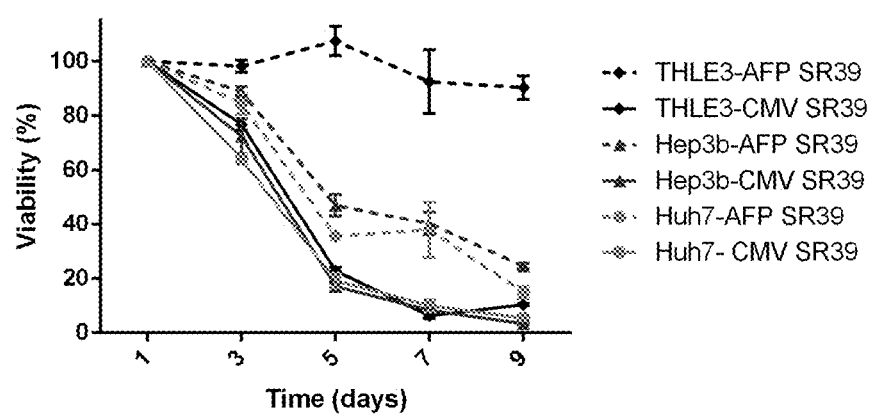
Figure 9:
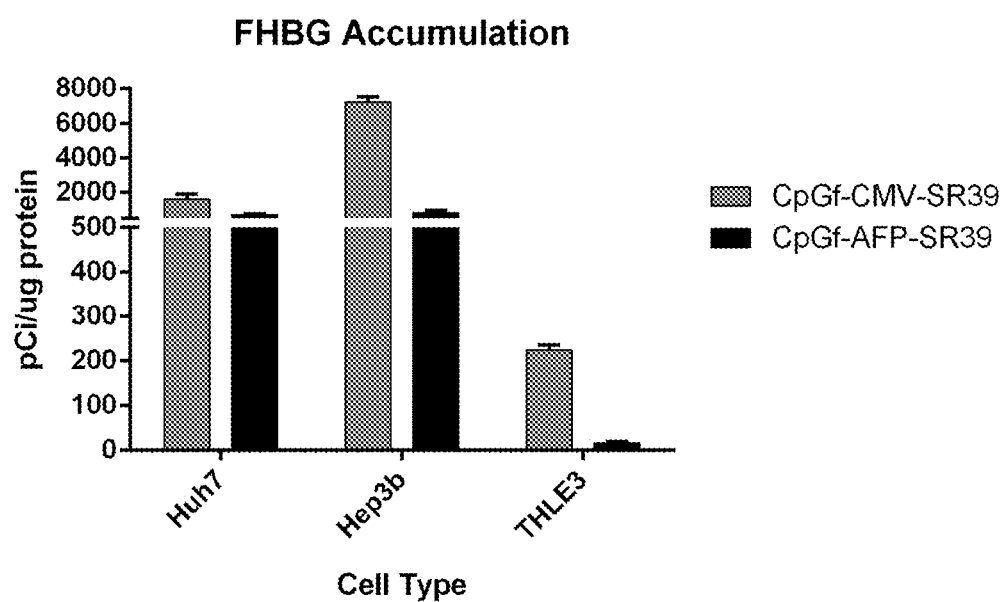
Figure 10:
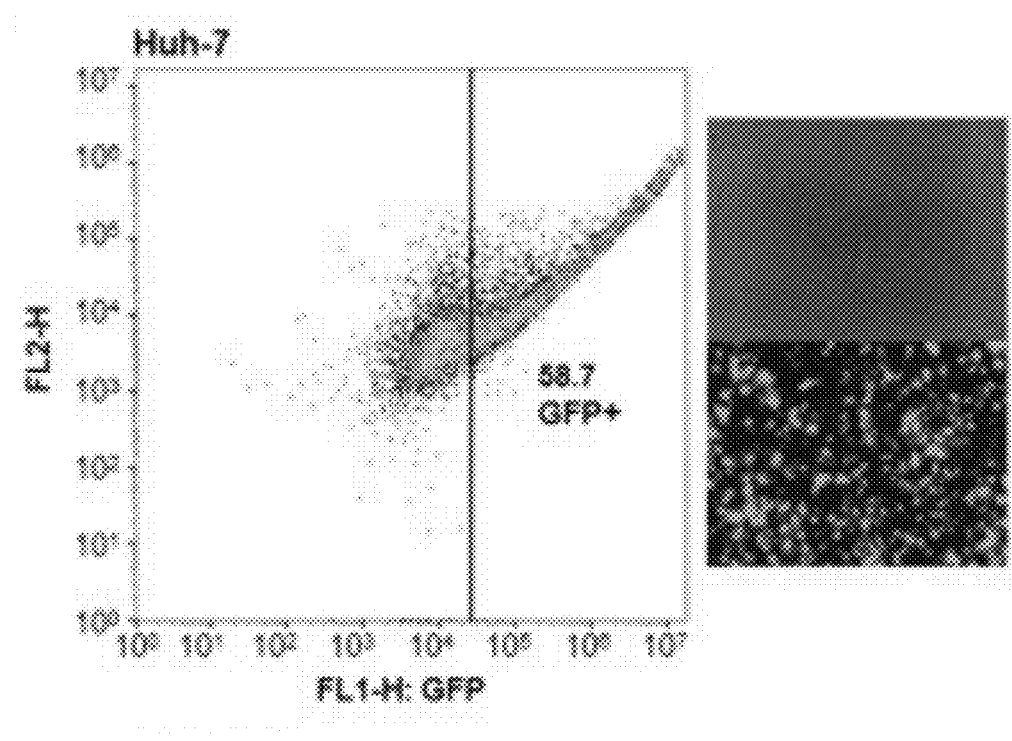
Figure 11:
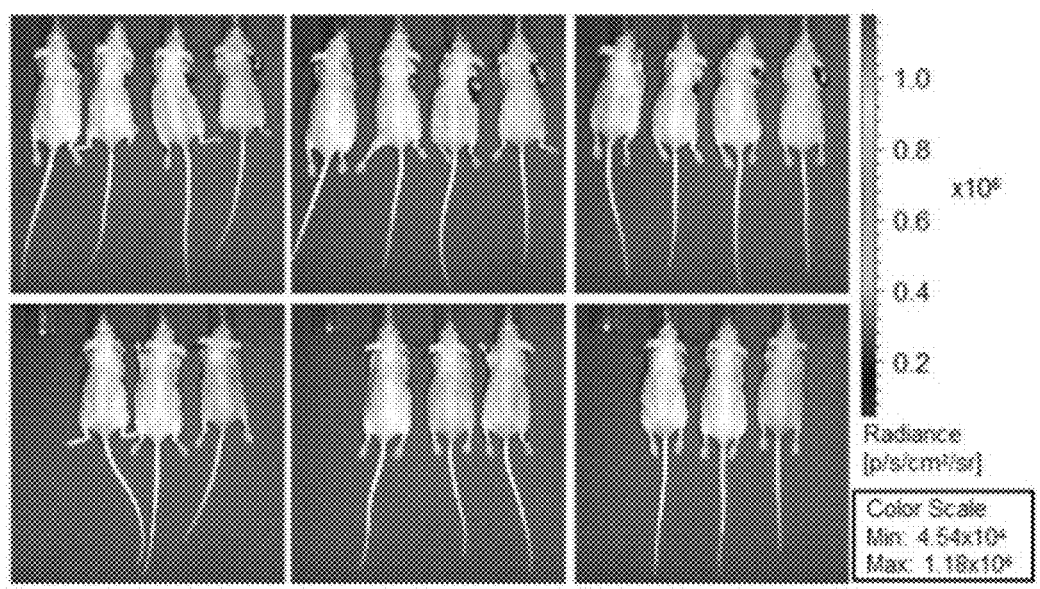
Figure 12:
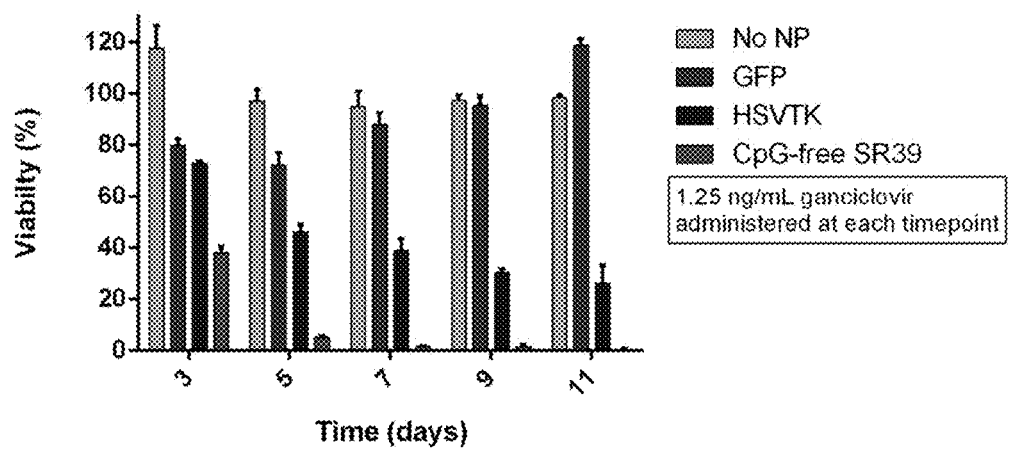
Figure 13:
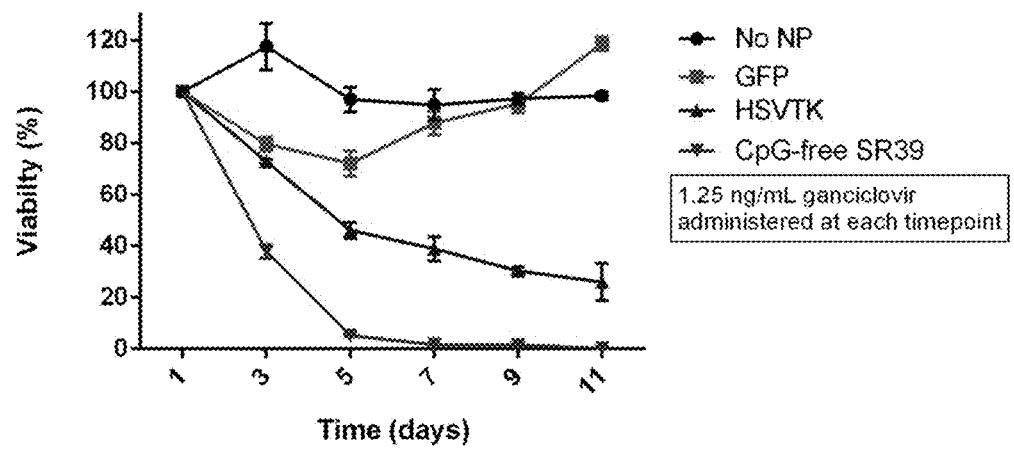
Figure 14:
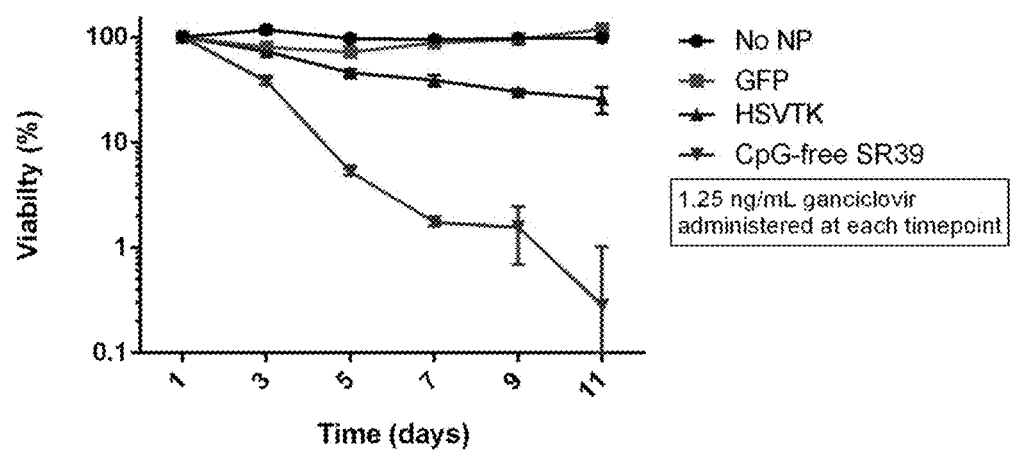
Figure 15:
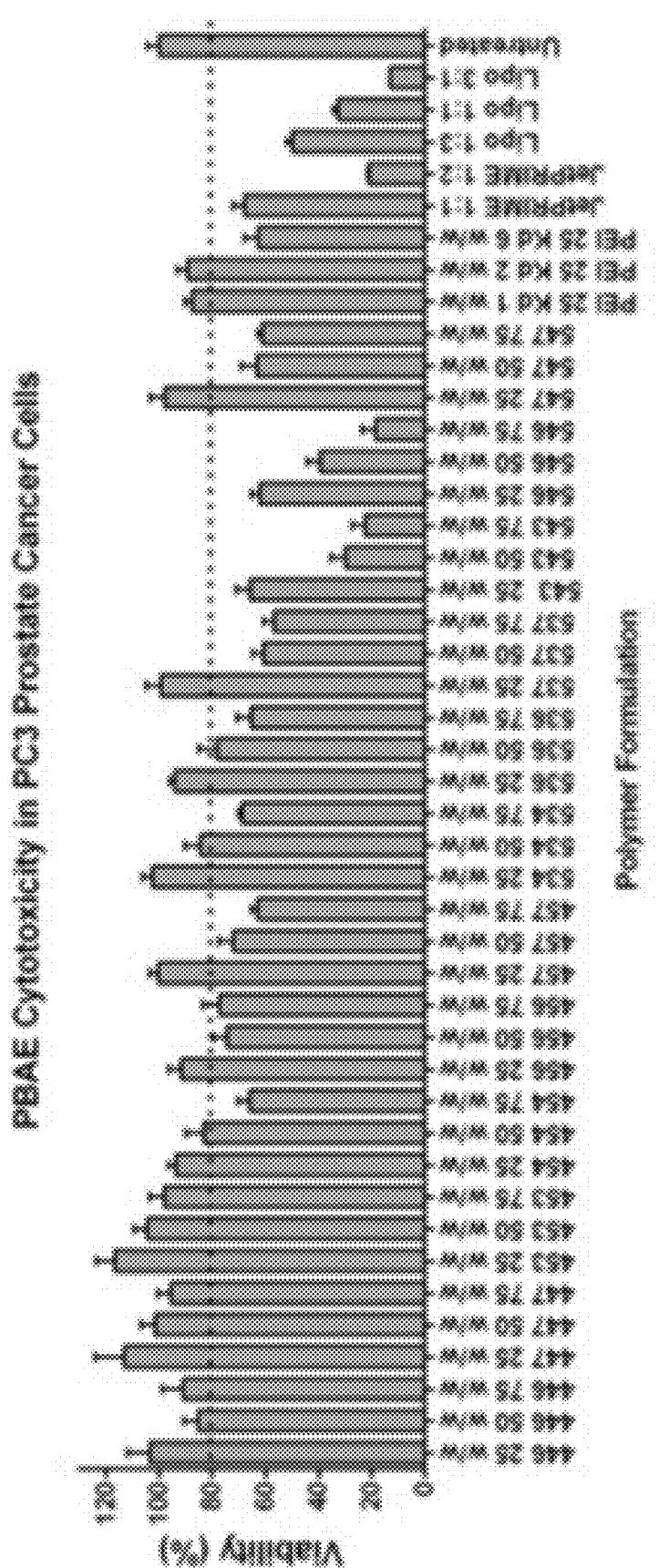
Figure 16:
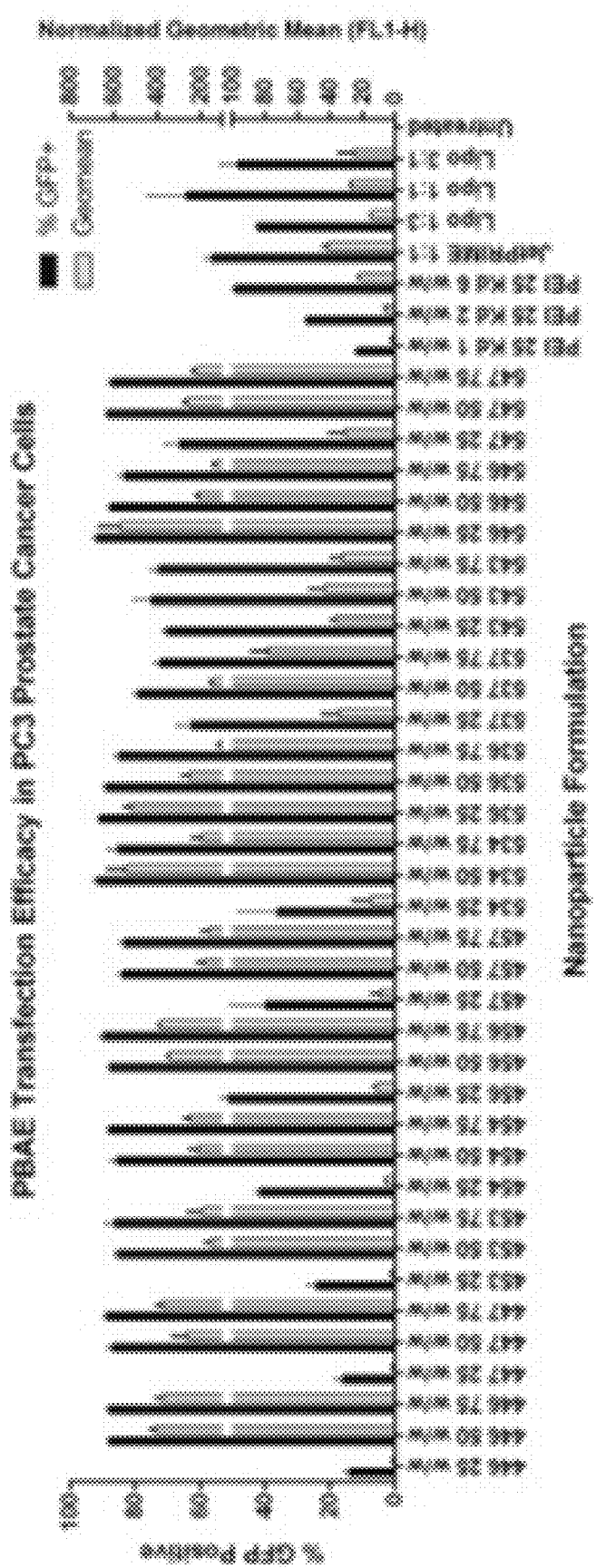
Figure 17A:
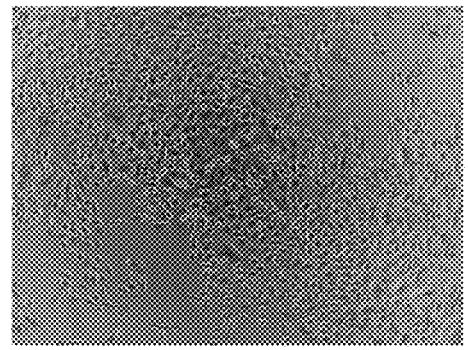
Figure 17B:
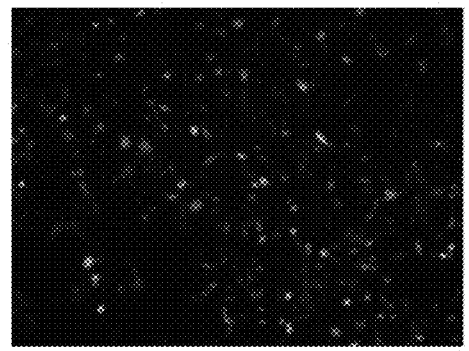
Figure 17C:
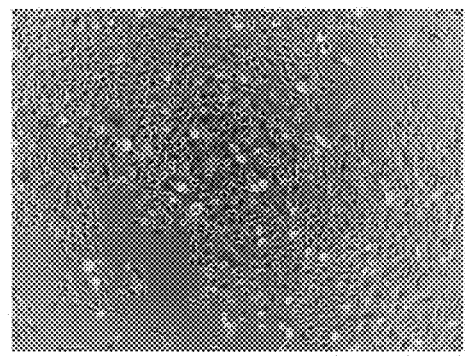
Figure 18:
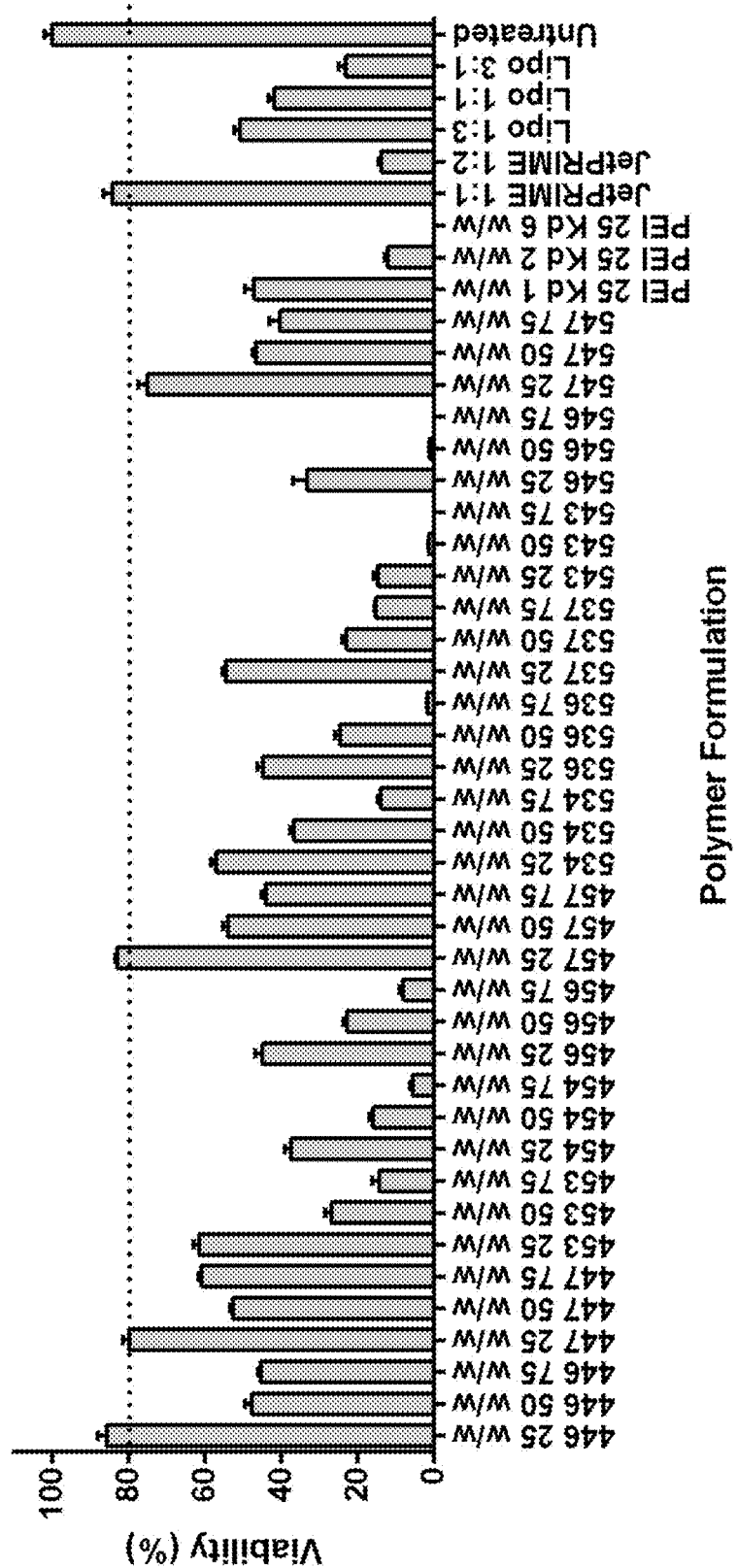
Figure 19:
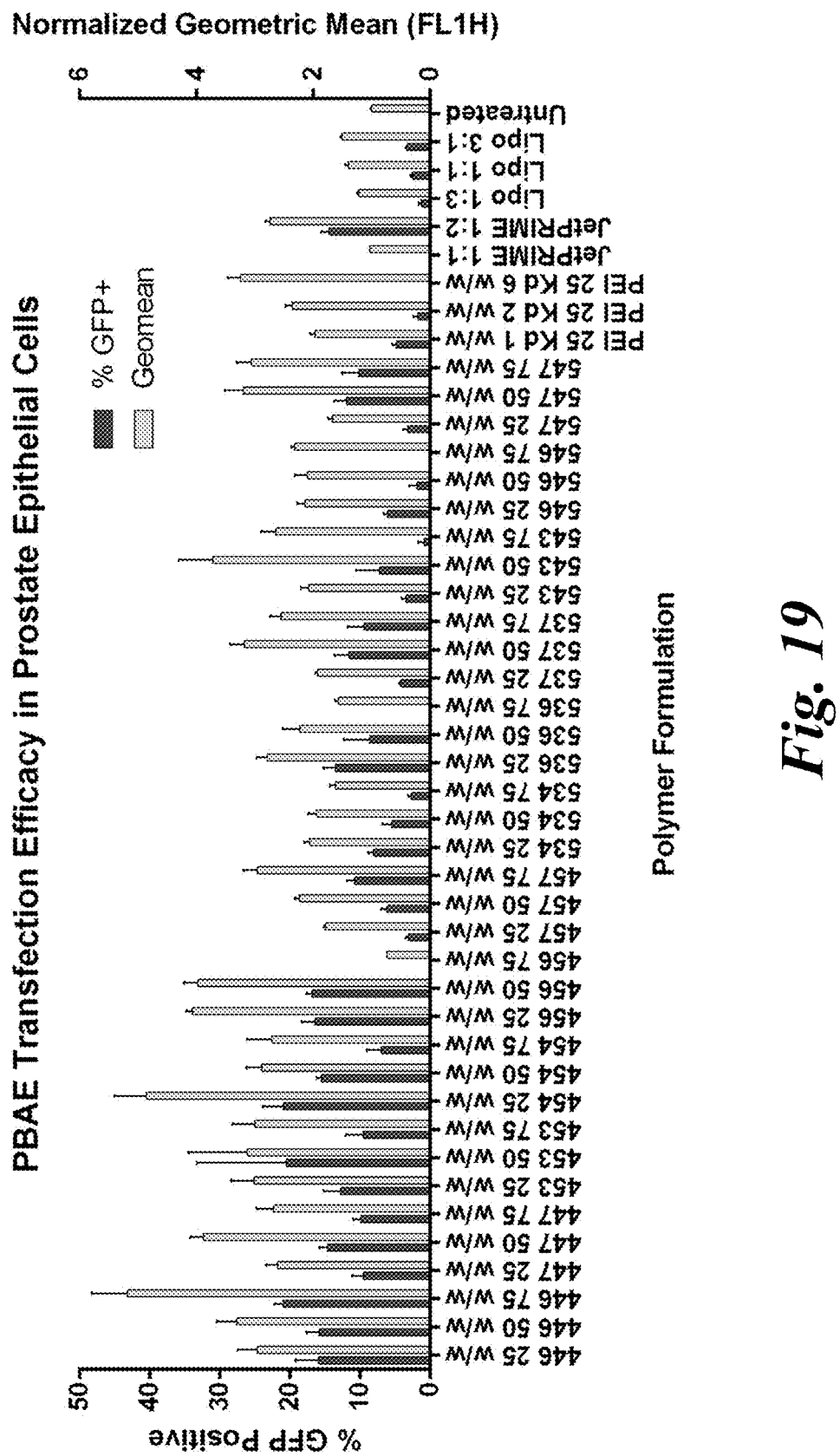
Figure 20A:
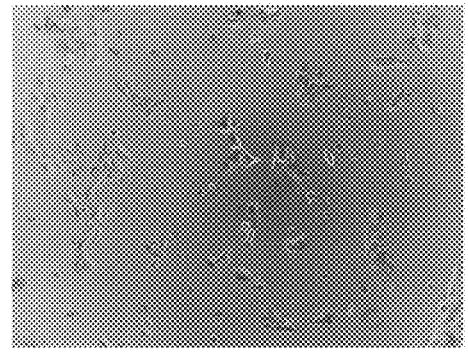
Figure 20B:
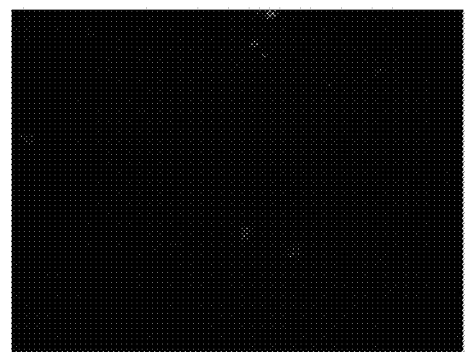
Figure 20C:
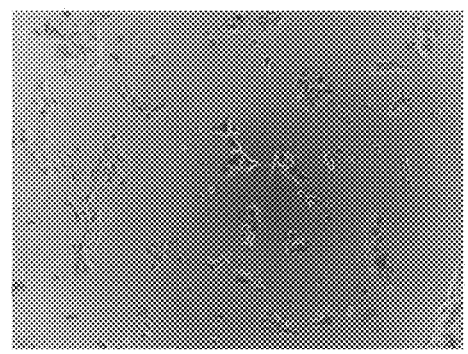
Figure 21:
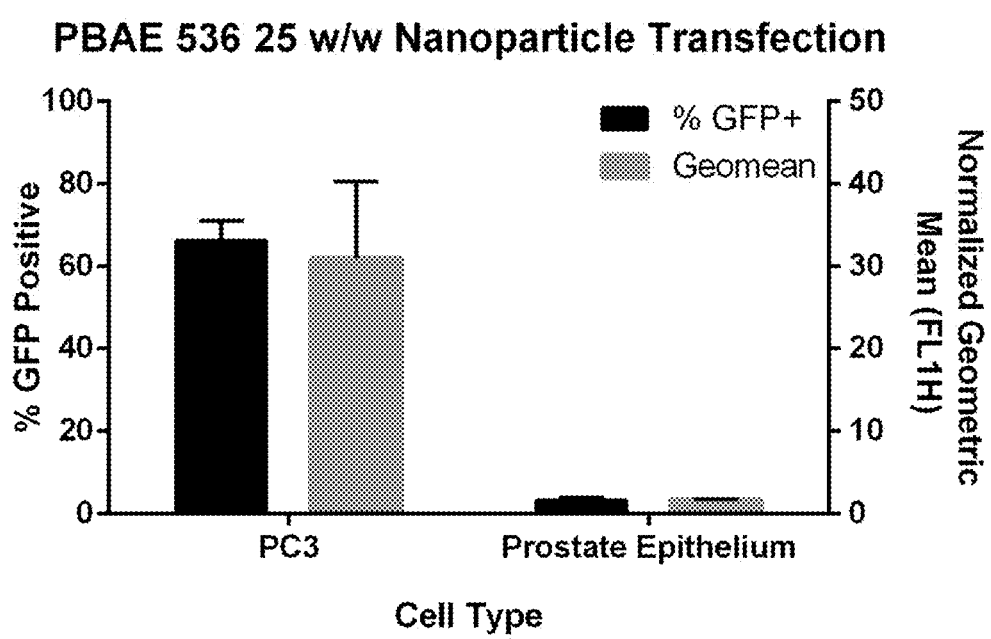
Figure 22:
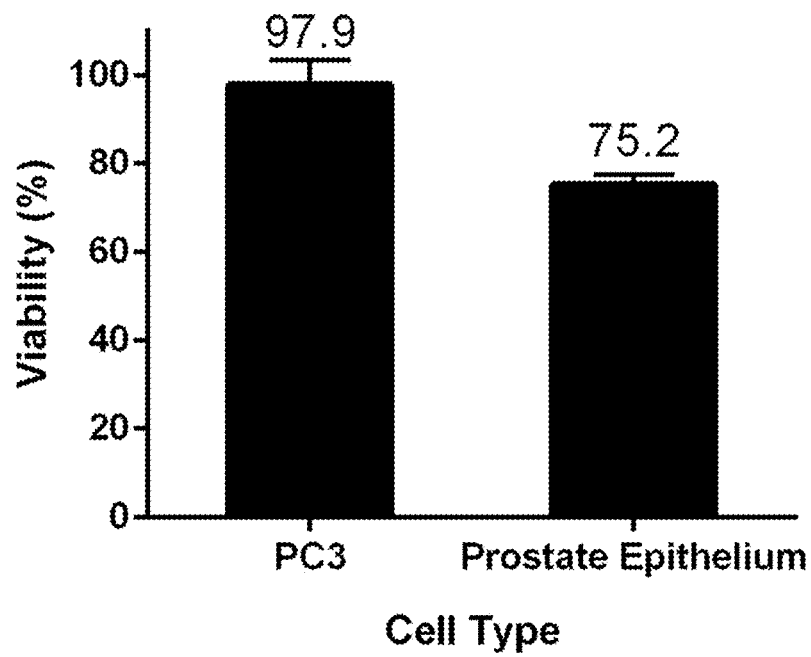
Figure 24:
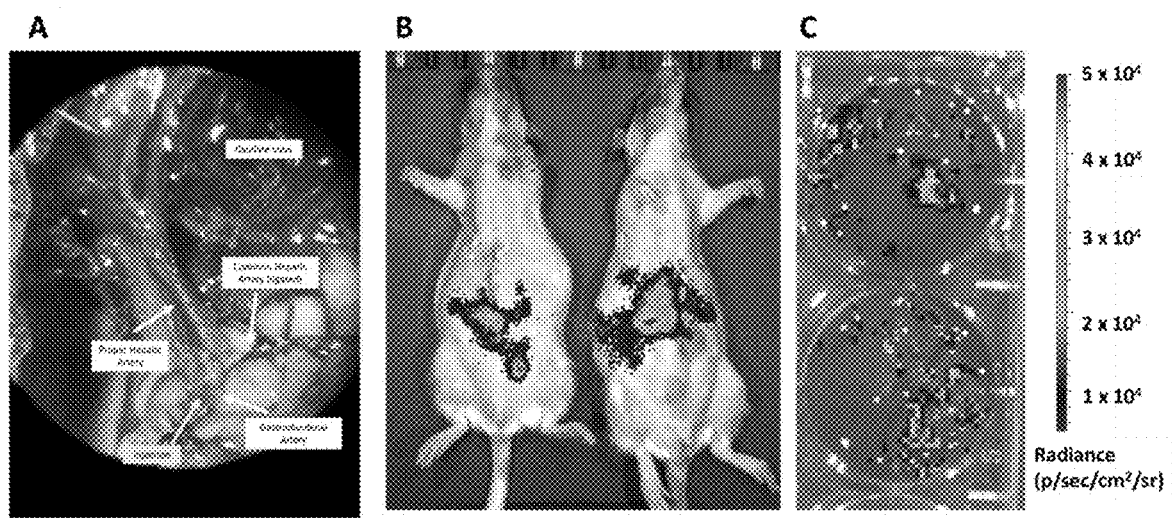
Figure 25:
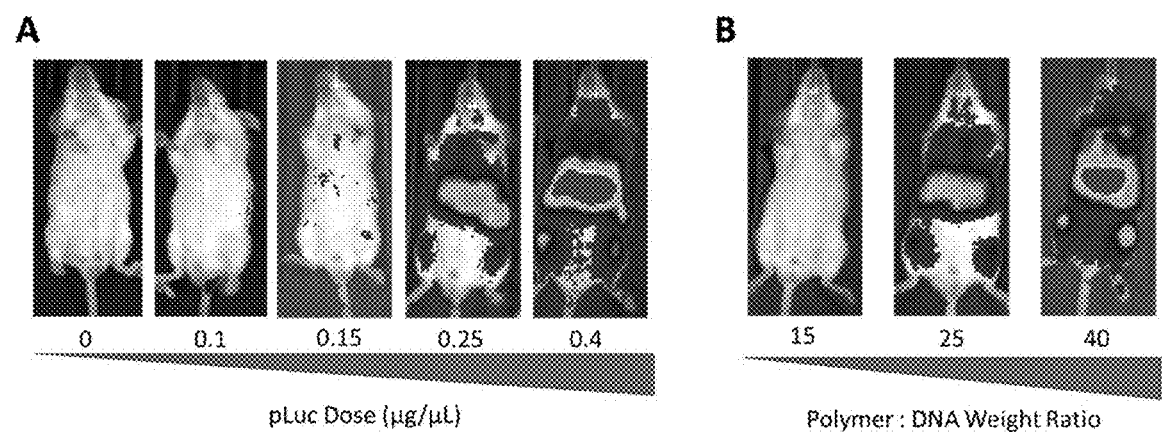
Figure 26:
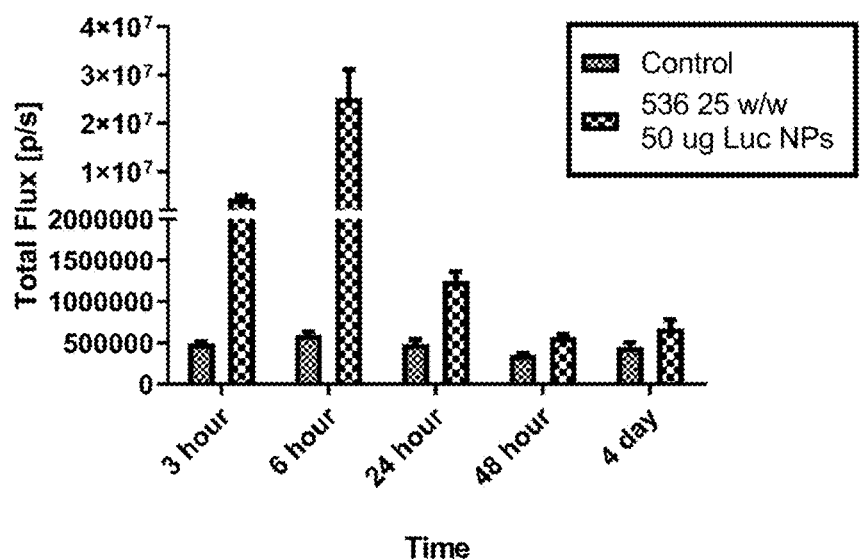
Figure 27:
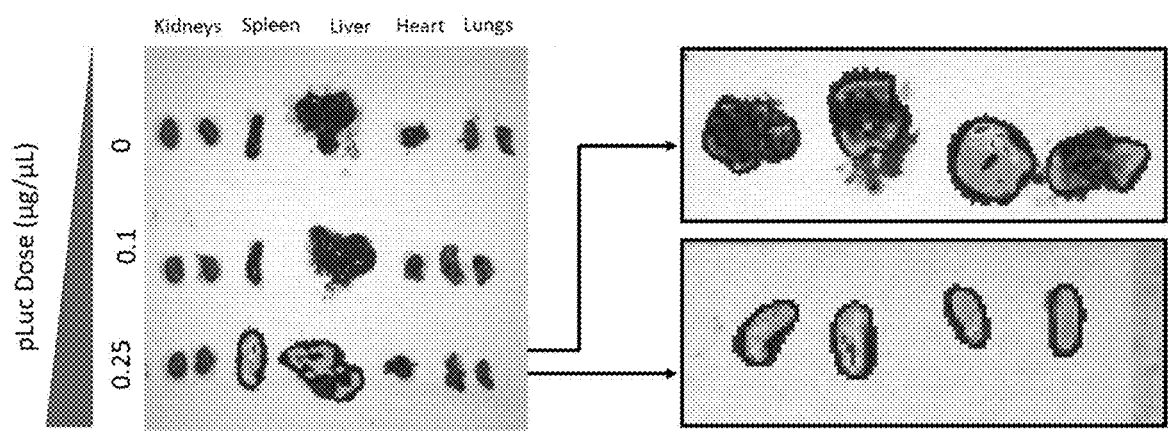
Figure 28:
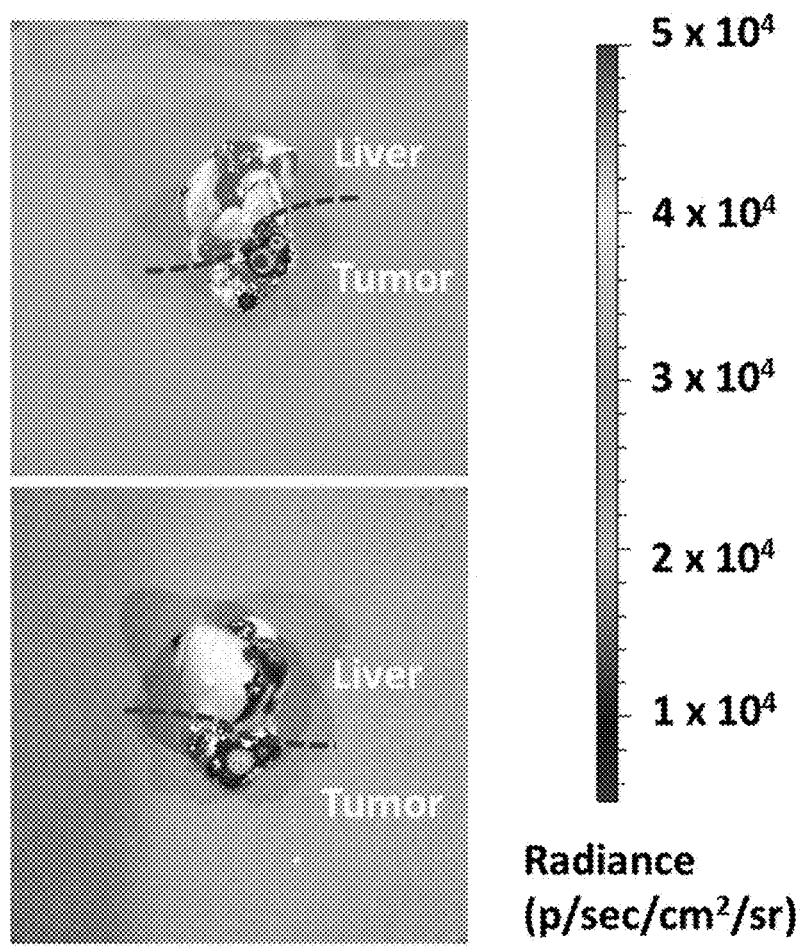
Figure 29:
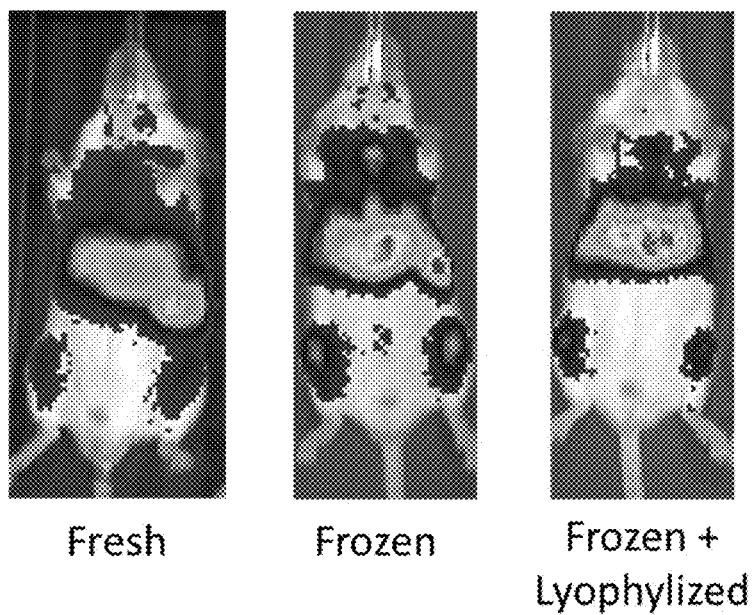
Figure 30:
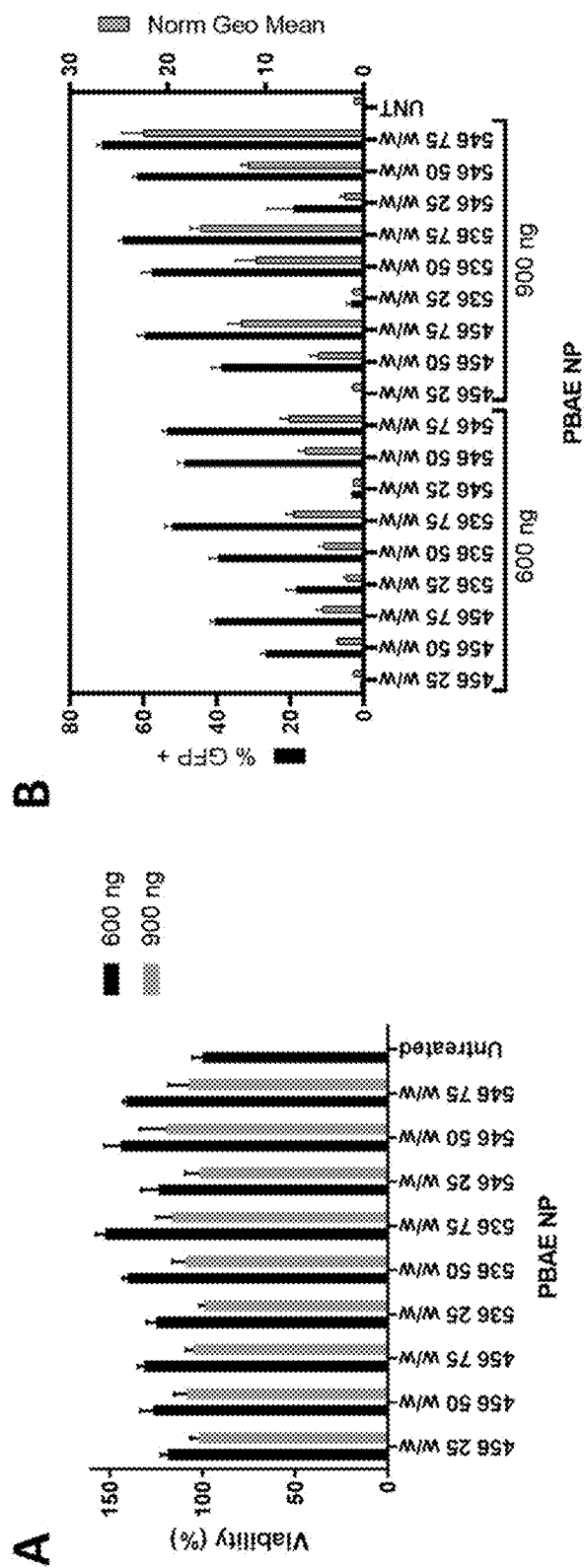
Figure 31:
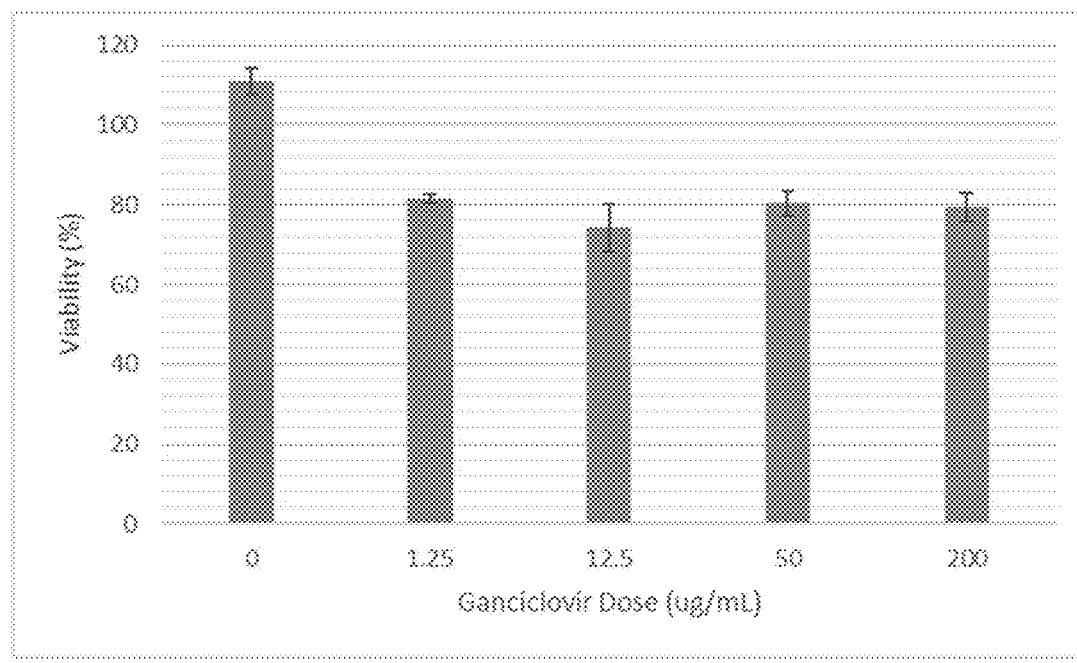
Figure 32:
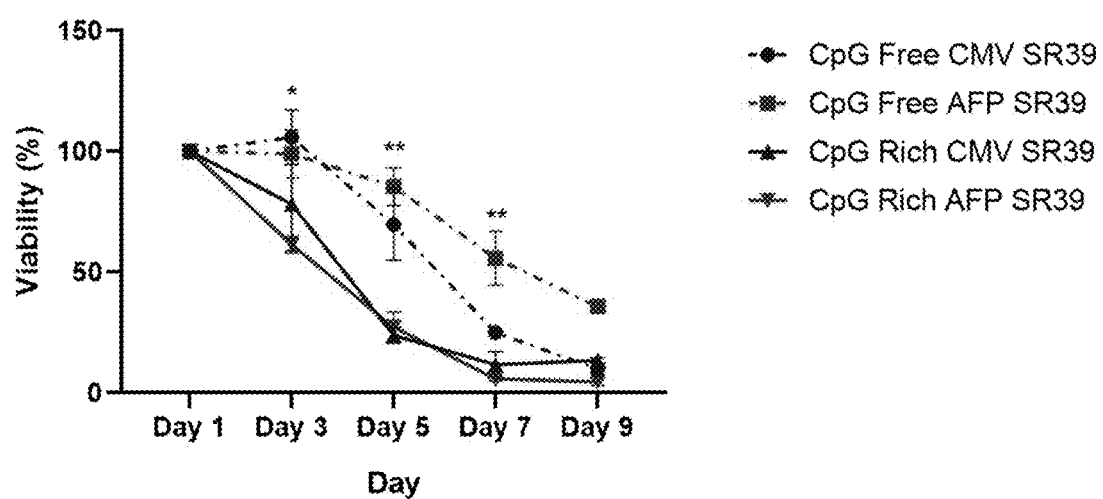

Having thus described the presently disclosed subject matter in general terms, reference will now be made to the accompanying Figures, which are not necessarily drawn to scale, and wherein:

FIG. 1 is a schematic of the AFP-SR39 theranostic gene delivery platform. The AFP-SR39 plasmid is combined with polymer PBAE 536 to form self-assembled PBAE polyplex nanoparticles (NPs). These particles transfect AFP-expressing HCC cells, where the PBAE NP facilitates intracellular delivery. When the transfected HCC cells are treated with GCV, the prodrug is phosphorylated by the SR39 enzyme and converted into a toxic inhibitor of DNA polymerase. Alternatively, transfected cells are treated with the radiotracer substrate [$^{18}$F]-FHBG, which is phosphorylated by the SR39 enzyme and leads to intracellular radiotracer accumulation;

FIG. 2A, FIG. 2B, FIG. 2C, FIG. 2D, and FIG. 2E shows PBAE NP 536 25 w/w eGFP-N1 characterization FIG. 2A is the chemical structure of PBAE 536; FIG. 2B shows the size and zeta potential of NPs measured by DLS; FIG. 2C is a TEM image of NPs; FIG. 2D shows the transfection efficacy of NPs in relevant cell lines measured by flow cytometry. *P<0.05 when compared with transfection in THLE3; FIG. 2E shows the cell viability 24 hours after transfection;

FIG. 3A and FIG. 3B show novel CpG free theranostic plasmids (FIG. 3A) pCpGfree-vitro-CMV-EF1-SR39 (CMV-SR39); and (FIG. 3B) pCpGfree-vitro-AFP-SR39 (AFP-SR39);

FIG. 4A and FIG. 4B show (FIG. 4A) relative expression of SR39 mRNA in transfected Hep3b cells. SR39 mRNA was detected using reverse transcription and qPCR, then normalized to untreated wells. *P<0.05 comparing CMV-SR39 to AFP-SR39 at each timepoint; and FIG. 4B viability of Hep 3b cells after transfection with eGFP-N1, HSV1-TK, or CMV-SR39 plasmids and treatment for 48 hours with varying doses of GCV. *P<0.001 comparing CMV-SR39 with HSV1-TK;

FIG. 5 shows AFP expression was quantified with immunostaining and flow cytometry in five relevant cell lines. % AFP+ describes the percentage of cells with intracellular AFP staining detectable by flow cytometry. Norm. Geo. Mean (Normalized Geometric Mean) describes the relative brightness of staining compared with background fluorescence in unstained cells. *P<0.05 comparing % AFP+ and Norm. Geo. Mean with all other cell lines;

FIG. 6A and FIG. 6B demonstrate the therapeutic effect of CpG free SR39 plasmids in AFP-producing HCC (Huh7, Hep3b), non-AFP producing HCC (SkHep1), prostate cancer (PC-3) and healthy hepatocytes (THLE3). FIG. 6A shows the viability of all cells transfected with CpGf-CMV-SR39 (solid) or wild-type HSV1-TK (dashed) and treated with GCV on Days 1, 3, 5, and 7. *P<0.05 comparing CpGf-CMV-SR39 with HSV1-TK for each cell line, where asterisk color indicates cell type; and FIG. 6B shows the viability of all cells transfected with CpGf-AFP-SR39 and treated with GCV on Days 1, 3, 5, and 7. *P<0.05;

FIG. 7A, FIG. 7B, and FIG. 7C shows [$^{18}$F]-FHBG accumulation in AFP-producing HCC (Huh7, Hep3b), non-AFP producing HCC (SkHep1), prostate cancer (PC-3) and healthy hepatocytes (THLE3); FIG. 7A shows 2 days post-transfection, cells were exposed to 10 μCi/mL [$^{18}$F]-FHBG for 1 hour, and intracellular accumulation was measured using a gamma counter; FIG. 7B shows 5 days post-transfection, cells were exposed to 10 μCi/mL [$^{18}$F]-FHBG for 1 hour, and intracellular accumulation was measured using a gamma counter; and FIG. 7C shows accumulation counts from Day 2 of transfection normalized to accumulation in THLE3 cells for each treatment *P<0.05 comparing between accumulation for cells transfected with CpGf-AFP-SR39;

FIG. 8 shows SR39+GCV mediated cell death in two AFP-producing HCC cell lines (Huh7 and Hep3b) and healthy hepatocytes (THLE3) transfected with PBAE nanoparticles delivering a plasmid encoding SR39 thymidine kinase under the control of either a constitutive promoter (CMV SR39) or AFP promoter (AFP SR39);

FIG. 9 shows FHBG accumulation in SR39-transfected Huh7, Hep3b, and THLE3 cells that were incubated with 9-(4-(18)F-fluoro-3-[hydroxymethyl]butyl) guanine ((18)F-FHBG);

FIG. 10 is flow cytometry gating and microscopy images of representative HCC lines and THLE-3 hepatocytes treated with 536 25 w/w;

FIG. 11 is bioluminescence images of subcutaneous Huh-7 xenograft mice at 6, 242, and 48 h following intra-tumoral injection of 536 25 w/w nanoparticles or PBS;

FIG. 12 and FIG. 13 show CpG-free SR39 delivery to hepatocellular carcinoma (HCC) cells, which demonstrates effective delivery of a representative theranostic gene, e.g., Cpg-free SR39, to HCC cells with minimal toxicity from control GFP nanoparticle;

FIG. 14 shows CpG-free SR39 delivery to hepatocellular carcinoma (HCC) cells, which demonstrates effective delivery of a representative theranostic gene, e.g., Cpg-free SR39, to HCC cells with minimal toxicity from control GFP nanoparticle;

FIG. 15 demonstrates that representative PBAEs exhibit low cytotoxicity in prostate cancer line (PC3);

FIG. 16 demonstrates that representative PBAEs exhibit high transfection efficacy in prostate cancer line (PC3);

FIG. 17A, FIG. 17B, and FIG. 17C are micrographs demonstrating that 446 50 w/w PBAE nanoparticles (FIG. 17A) maintain high viability to PC3 cells; (FIG. 17B) exhibit high transfection to PC3 cells; and (FIG. 17C) exhibit safe and effective transfection to PC3 cells;

FIG. 18 demonstrates that selected PBAE formulations exhibit low cytotoxicity in healthy prostate epithelial cells;

FIG. 19 demonstrates that selected PBAE formulations exhibit low transfection in healthy prostate epithelial cells with possible biomaterial-mediated targeting;

FIG. 20A, FIG. 20B, and FIG. 20C show that PBAE nanoparticles have low transfection to healthy prostate epithelial cells, demonstrating that the nanoparticles can enable specific gene delivery to prostate cancer cells over healthy cells, (FIG. 20A) 547 25 w/w nanoparticles; (FIG. 20B) 547 25 w/w nanoparticles GFP channel; and (FIG. 20C) 547 25 w/w nanoparticles channels merged;

FIG. 21 shows prostate cancer cell specificity for PBAE 547 25 w/w nanoparticle transfection head to head with healthy prostate epithelial cells;

FIG. 22 illustrates nanoparticle cell viability for PBAE 547 25 w/w with minimal cytotoxicity;

FIG. 23 is a table which sets forth the nucleic acid sequence and amino acid sequences described herein;

FIG. 24, Panels A-C show local delivery of representative presently disclosed nanoparticles to liver via proper hepatic artery. Polymeric nanoparticles optimized for hepatocellular carcinoma (HCC) tumor delivery (PBAE 536 NP) may be administered locally via the proper hepatic artery (Panel A), for effective gene reporter gene delivery in athymic nude rats (Panel B) and liver (Panel C). This local delivery route is known to preferentially feed HCC tumors over healthy liver and is a clinically used minimally invasive procedure established for transarterial chemoembolization (TACE);

FIG. 25, Panels A and B show delivery of representative presently disclosed nanoparticles to liver and spleen via tail vein. Intravenous administration of optimized polymeric nanoparticles (PBAE 536 25 w/w) results in dose responsive reporter DNA delivery in mice, showing enhanced expression with increasing DNA (Panel A) and polymer (Panel B) dose;

FIG. 26 shows whole body luminescence of systemic PBAE nanoparticles. Luminescence signal shows sustained expression of a reporter gene delivered by intravenously administered optimized polymer nanoparticles (PBAE 536 25 w/w, 25 μg DNA dose);

FIG. 27 shows intravenously delivered optimized polymer nanoparticles (PBAE 536 25 w/w, 25 μg DNA dose) facilitate reporter gene delivery to liver and spleen in healthy mice. Transfection in these tissues highlights the importance of transcriptional targeting to cancer cells for selective HCC killing;

FIG. 28 shows delivery of representative presently disclosed nanoparticles to HCC tumor via tail vein. Intravenous administration of optimized polymeric nanoparticles (PBAE 536 25 w/w, 25 μg DNA dose) results in selective delivery of reporter DNA to orthotopic xenograft HCC tumor in athymic nude mice;

FIG. 29 shows alternative nanoparticle formulations including freezing and lyophilization. PBAE 536 25 w/w NPs may be formulated with 90 mg/mL sucrose and frozen at −80° C. or lyophilized, then thawed or reconstituted in water with similar delivery efficacy to fresh nanoparticles. This example demonstrates effective storage and stability of both the polymer and nucleic acid that make up the presently disclosed biodegradable gene delivery product;

FIG. 30, Panels A and B show PBAE nanoparticle screening and CMV-SR39 efficacy in mouse HCC cells (Hepa1-6). PBAE nanoparticles are nontoxic to Hepa1-6 mouse HCC cells (Panel A) and achieve effective gene delivery with a diverse library of nanoparticle formulations (Panel B). Achieving safe and efficient gene delivery in mouse liver cancer cells enables testing various therapeutic plasmids in a syngeneic mouse HCC model;

FIG. 31 shows mouse HCC cell line Hepa1-6 treated with PBAE 547 75 w/w nanoparticles harboring CMV-SR39 DNA and ganciclovir prodrug show significant decrease in viability after 3 days, which suggests this plasmid may be applied to syngeneic murine models of HCC; and FIG. 32 shows CpG-rich plasmids. In some embodiments, CpG-rich versions of the CMV SR39 and AFP SR39 plasmids are preferred. For example, for an in vitro transfection, Hep3b cells treated with CpG-rich SR39 plasmids and 1.25 µg/mL ganciclovir show a decrease in viability over a 9-day time course. All four plasmids show efficacy in this in vitro system and CpG can provide in vivo benefits beyond an in vitro assay.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Transcriptionally Targeted and Cpg-Free Plasmid for Theranostic Gene Therapy

As provided in more detail herein below, in some embodiments, the presently disclosed subject matter provides a CpG-free plasmid encoding a mutant thymidine kinase (TK), such as the SR39 mutant (described in e.g., Black et al., *Cancer Res.*, 61(7): 3022-3026 (2001); Wiewrodt et al., Cancer Gene Ther. 2003, 10(5):353-64; and Barton et al., Mol Ther 2011, 19(7):1353-9). In some embodiments, the CpG-free plasmid encoding the SR39 gene is driven by a promoter region comprising a CMV promoter (e.g., a mouse CMV promoter) and a human EF1 enhancer (CMV-SR39 promoter). In some embodiments, the presently disclosed subject matter provides a composite CpG-free AFP promoter and enhancer. In other embodiments, a plasmid expressing SR39 driven by the AFP promoter is disclosed. In particular embodiments, a CpG-free plasmid encoding the SR39 gene driven by the AFP (AFP-SR39) promoter is disclosed.

The presently disclosed subject matter also provides a non-viral gene delivery vector/particle encapsulating said plasmid types, including CMV-SR39 and AFP-SR39. In particular embodiments, the presently disclosed subject matter provides a polymeric nanoparticle comprising a cationic polymer and plasmid CMV-SR39 or AFP-SR39, or a derivative thereof.

The presently disclosed plasmids and compositions thereof can be used for diagnostics, therapy, or research, including, but not limited to, use as a diagnostic/imaging agent, or in cancer therapy, in particular liver cancer or prostate cancer diagnostics, research, or therapy.

A. CpG-Free CMV-SR39 and AFP-SR39

In some embodiments, the presently disclosed subject matter provides a nucleic acid molecule comprising a nucleic acid sequence encoding a mutant thymidine kinase (TK) protein operatively linked to an alpha-fetoprotein (AFP) gene promoter.

As used herein, a "promoter" is a DNA sequence that directs the binding of RNA polymerase and thereby promotes RNA synthesis. A nucleic acid sequence is "operably linked" or "operatively linked" to a promoter when the promoter is capable of directing transcription of that nucleic acid sequence. A promoter can be native or non-native to the nucleic acid sequence to which it is operably or operatively linked. Techniques for operably linking sequences together are well known in the art. The term "constitutive promoter," as used herein, refers to an unregulated promoter that allows for continual transcription of its associated gene in a variety of cell types. Suitable constitutive promoters are known in the art and can be used in connection with the present disclosure. Non-CpG-free AFP promoters have been described by Zhang et al., 2012, and Kim et al., 2002.

In some embodiments, the constitutive promoter comprises all or part of a cytomegalovirus (CMV) promoter. In one embodiment, the constitutive promoter may comprise a mouse CMV promoter and a human EF1 enhancer. A "cancer-specific promoter" is a promoter that is preferentially activated in a cells of a specific cancer type (e.g., hepatocellular cancer cells), which allows for selective expression of an associated gene in cancer cells where the promoter is active. A variety of cancer-specific promoters are known in the art, including promoters specifically activated in hepatocellular and prostate cancer cells, and any such promoters may be used in the context of the present disclosure. In some embodiments, the cancer-specific promoter is the promoter of the alpha fetoprotein (AFP) gene.

In particular embodiments, the nucleic acid sequence encodes a TK mutant protein comprising the amino acid sequence of SEQ ID NO: 1. In certain embodiments, the nucleic acid sequence encoding a mutant TK protein lacks CpG dinucleotides. In more certain embodiments, the AFP gene promoter lacks CpG dinucleotides. In yet more certain embodiments, the AFP gene promoter comprises the nucleic acid sequence of SEQ ID NO: 3.

In other embodiments, the presently disclosed subject matter provides a nucleic acid molecule comprising a nucleic acid sequence encoding a mutant thymidine kinase (TK) protein operatively liked to a non-native promoter, wherein the nucleic acid sequence lacks CpG dinucleotides. In particular embodiments, the nucleic acid sequence encodes a TK mutant protein comprising the amino acid sequence of SEQ ID NO: 1. In certain embodiments, the nucleic acid sequence encoding a mutant TK protein lacks CpG dinucleotides. In more certain embodiments, the non-native promoter comprises a mouse CMV promoter and human EF1 enhancer.

In particular embodiments, the nucleic acid molecule is plasmid DNA.

In other embodiments, the presently disclosed subject matter provides an isolated nucleic acid sequence comprising an alpha-fetoprotein (AFP) gene promoter which lacks CpG dinucleotides. In particular embodiments, the isolated nucleic acid sequence comprises SEQ ID NO: 3.

In certain embodiments, the presently disclosed subject matter provides a composition comprising the above-described nucleic acid molecule and biodegradable particles comprising a PBAE of formula (I), as disclosed herein below, for delivering nucleic acids, including plasmid DNA, to cells, such as cancer cells. The presently disclosed particles provide for efficient transfection of cells with nucleic acid, including plasmid DNA. Accordingly, the presently disclosed subject matter provides an efficient gene therapy platform, involving either ex vivo or in vivo plasmid DNA delivery.

B. Representative Compositions of Formula (I)

The presently disclosed subject matter provides multi-component degradable cationic polymers for gene delivery to cells, including hepatocellular carcinoma (HCC) cells and prostate cancer cells. The presently disclosed polymers have the property of biphasic degradation and modifications to the polymer structure can result in a change in the release of therapeutic agents, e.g., a DNA plasmid. In some embodiments, the presently disclosed polymers include a minority structure, e.g., an endcapping group, which differs from the majority structure comprising most of the polymer backbone. In other embodiments, the bioreducible oligomers form block copolymers with hydrolytically degradable oligomers. In yet other embodiments, the end group/minority structure comprises an amino acid or chain of amino acids, while the backbone degrades hydrolytically and/or is bioreducible.

Small changes in the monomer ratio used during polymerization, in combination with modifications to the chemical structure of the end-capping groups used post-polymerization, can affect the efficacy of delivery of a therapeutic agent, including, but not limited to DNA plasmid, to a target. Further, changes in the chemical structure of the polymer, either in the backbone of the polymer or end-capping groups, or both, can change the efficacy of gene delivery to a cell, e.g., a cancerous fibroblast line or a human primary fibroblast. In some embodiments, small changes to the molecular weight of the polymer or changes to the endcapping groups of the polymer, while leaving the main chain, i.e., backbone, of the polymer the same, can enhance or decrease the overall delivery of the gene to a cell. Further, the "R" groups that comprise the backbone or main chain of the polymer can be selected to degrade via different biodegradation mechanisms within the same polymer molecule. Such mechanisms include, but are not limited to, hydrolytic, bioreducible, enzymatic, and/or other modes of degradation.

The properties of the presently disclosed multicomponent degradable cationic polymers can be tuned to impart one or more of the following characteristics to the composition: independent control of cell-specific uptake and/or intracellular delivery of a particle; independent control of endosomal buffering and endosomal escape; independent control of DNA release; triggered release of an active agent; modification of a particle surface charge; increased diffusion through a cytoplasm of a cell; increased active transport through a cytoplasm of a cell; increased nuclear import within a cell; increased transcription of an associated DNA within a cell; increased translation of an associated DNA within a cell; and/or increased persistence of an associated therapeutic agent within a cell.

If a hydrophilic peptide/protein is to be encapsulated, a hydrophilic polymer is chosen as the multicomponent material. If a hydrophobic peptide/protein is to be encapsulated than a hydrophobic polymer is chosen. The polymer backbone, side chain, and/or terminal group can be modified to increase the hydrophobic or hydrophilic character of the polymer. The peptide/protein to be encapsulated can be first dissolved in a suitable solvent, such as DMSO or PBS. Then, it is combined with the polymer in, for example, sodium acetate (NaAc). This solution is then diluted with either sodium acetate, OptiMem, DMEM, PBS, or water depending on the particle size desired. The solution in vortexed to mix and then left to incubate for a period of time for particle assembly to take place. The particles can self-assemble with nucleic acid, including plasmid DNA, to form nanoparticles that can be in the range of 50 nm to 500 nm in size. The particles provide for efficient transfection of cells with plasmid DNA, either in vivo or ex vivo.

Representative multicomponent degradable cationic polymers are disclosed in the following U.S. patents and U.S. patent application publications, each of which is incorporated herein by reference in its entirety:

U.S. Patent Application Publication No. 20180177881 for Multicomponent Degradable Cationic Polymers, to Green et al., published Jun. 28, 2018;

U.S. Patent Application Publication No. 20150250881 for Multicomponent Degradable Cationic Polymers, to Green et al., published Sep. 10, 2015;

U.S. Patent Application Publication No. 20120128782 for Multicomponent Degradable Cationic Polymers, to Green et al., published May 24, 2012;

U.S. Patent Application Publication No. 20180112038 for Poly(beta-amino ester)-co-polyethylene glycol (PEG-PBAE-PEG) Polymers for Gene and Drug Delivery, to Green et al., published Apr. 26, 2018;

U.S. Patent Application Publication No. 20180028455 for Peptide/Particle Delivery Systems, to Green et al., published Feb. 1, 2018;

U.S. Patent Application Publication No. 20160374949 for Peptide/Particle Delivery Systems, to Green et al., published Dec. 29, 2016;

U.S. Patent Application Publication No. 20120114759 for Peptide/Particle Delivery Systems, to Green et al., published Dec. 29, 2016;

U.S. Patent Application Publication No. 20160122390 for A Biomimetic Peptide and Biodegradable Delivery Platform for the Treatment of Angiogenesis- and Lymphangiogenesis-Dependent Diseases, to Popel, et al, published May 5, 2016.

U.S. Patent Application Publication No. 20150273071 for Bioreducible Poly (Beta-Amino Ester)s for siRNA Delivery, to Green et al., published Oct. 1, 2015;

U.S. Pat. No. 9,884,118 for Multicomponent Degradable Cationic Polymers, to Green, et al., issued Feb. 6, 2018;

U.S. Pat. No. 9,717,694 for Peptide/particle Delivery Systems, Green, et al., issued Aug. 1, 2017; and U.S. Pat. No. 8,992,991 for Multicomponent Degradable Cationic Polymers, to Green, et al., issued Mar. 31, 2015.

U.S. Pat. No. 8,287,849 for Biodegradable Poly(beta-amino esters) and Uses Thereof, to Langer, et al., issued Oct. 16, 2012;

The presently disclosed multicomponent degradable cationic polymers can be prepared by the following reaction scheme:

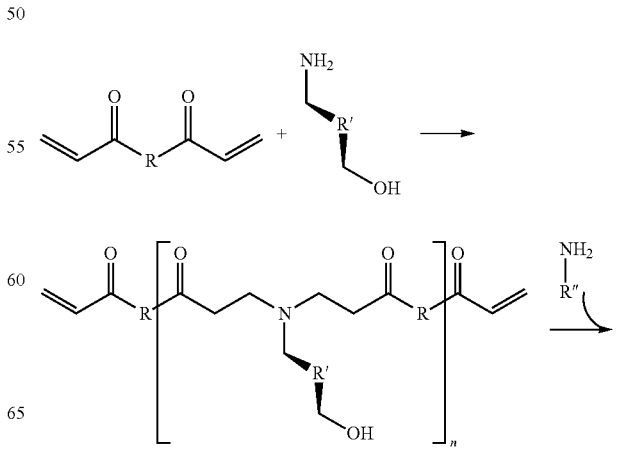

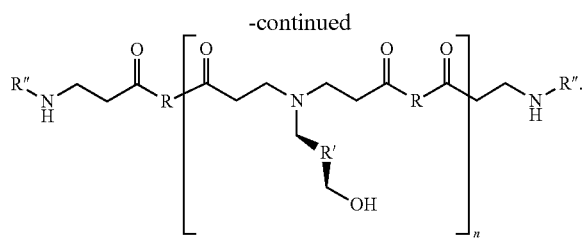

Generally, the presently disclosed multicomponent degradable cationic polymers include a backbone derived from a diacrylate monomer (designated herein below as "B"), an amino-alcohol side chain monomer (designated herein below as "S"), and an amine-containing end-cap monomer (designated herein below as "E"). The end group structures are distinct and separate from the polymer backbone structures and the side chain structures of the intermediate precursor molecule for a given polymeric material. The presently disclosed PBAE compositions can be designated, for example, as B5-S4-E7 or 547, in which R is B5, R' is S4, and R" is E7, and the like, where B is for backbone and S is for the side chain, followed by the number of carbons in their hydrocarbon chain. Endcapping monomers, E, are sequentially numbered according to similarities in their amine structures.

The polymer backbone can comprise a diacrylate having the following general formula, where $R_o$ comprises a linear, branched, and/or substituted alkylene, and may comprise one or more heteroatoms, such as O, N, or S, and may include one or more carbocyclic, heterocyclic, and aromatic groups:

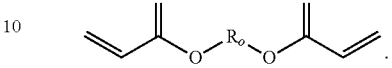

In some embodiments, the diacrylate has the general formula of:

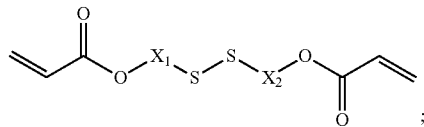

where $X_1$ and $X_2$ are each independently $C_1$—$C_{30}$ alkylene chains.

In particular embodiments, the diacrylate monomer for the polymer backbone is selected from:

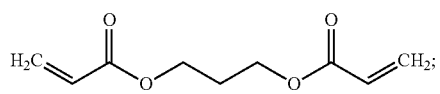

(B3)

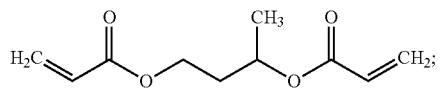

(B3b)

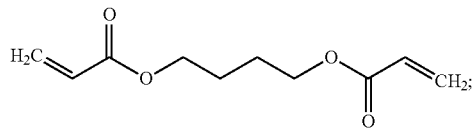

(B4)

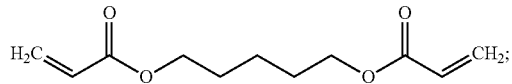

(B5)

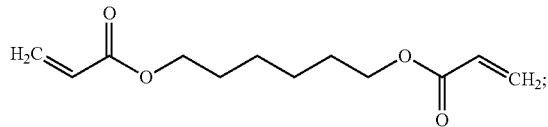

(B6)

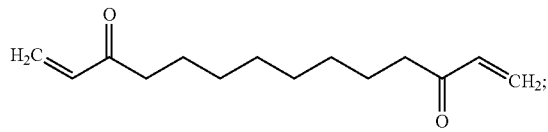

(B8)

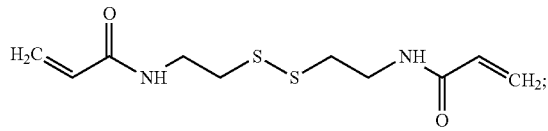

(BSS)

-continued
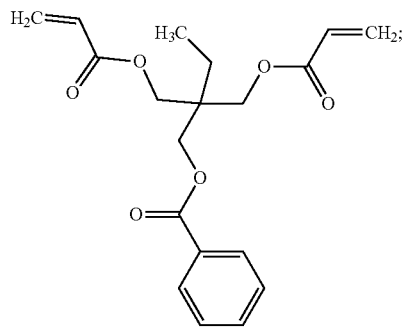
(BL1)
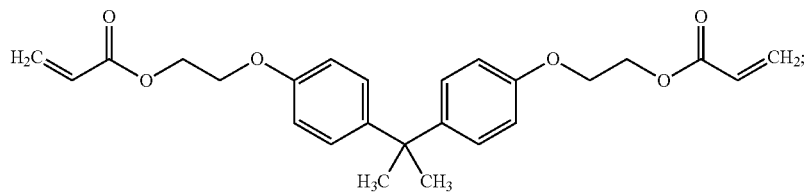
(BL2)
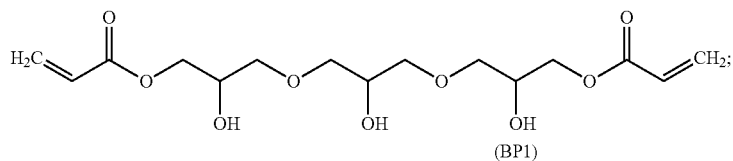
(BH1)
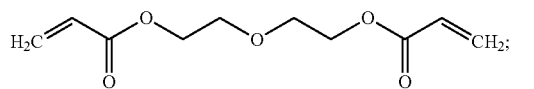
(BP1)
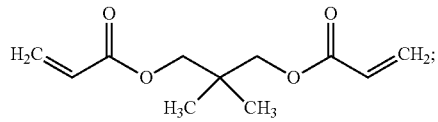
(BP2)
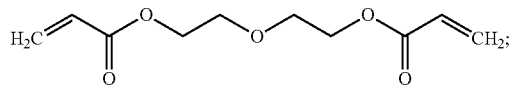
(BP1)
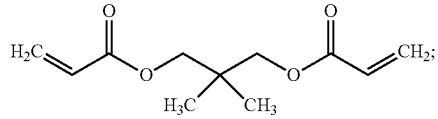
(BP2)
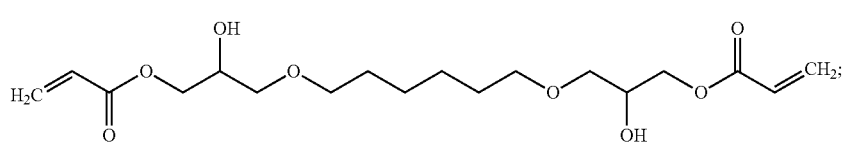
(BP3)
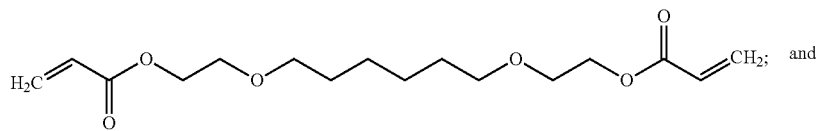
(BP4) and
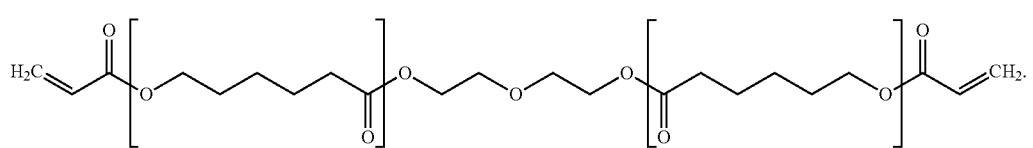
(BP6)

As shown in the reaction scheme provided hereinabove, acrylate monomers can be condensed with amine-containing side chain monomers. In some embodiments, the side chain monomers comprise a primary amine, but, in other embodiments, comprise secondary and tertiary amines. Side chain monomers may further comprise a $C_1$ to $C_8$ linear or branched alkylene, which is optionally substituted. Illustrative substituents include hydroxyl, alkyl, alkenyl, thiol, amine, carbonyl, and halogen.

In particular embodiments, the side chain monomer is selected from:

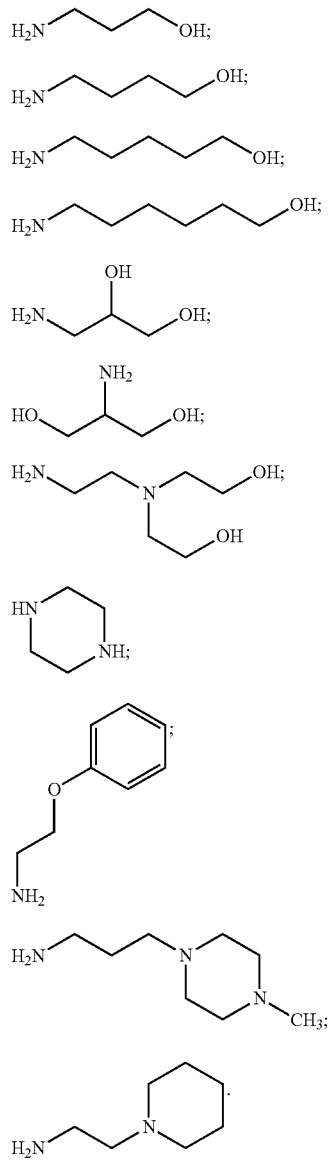

The PBAE polymer further comprises an end group, which may include one or more primary, secondary or tertiary amines, and may include aromatic and non-aromatic carbocyclic and heterocyclic groups, such as carbocyclic and heterocyclic groups of 5 or 6 atoms. The end group in some embodiments may comprise one or more ether, thioether, or disulfide linkages.

Representative end groups include, but are not limited to:

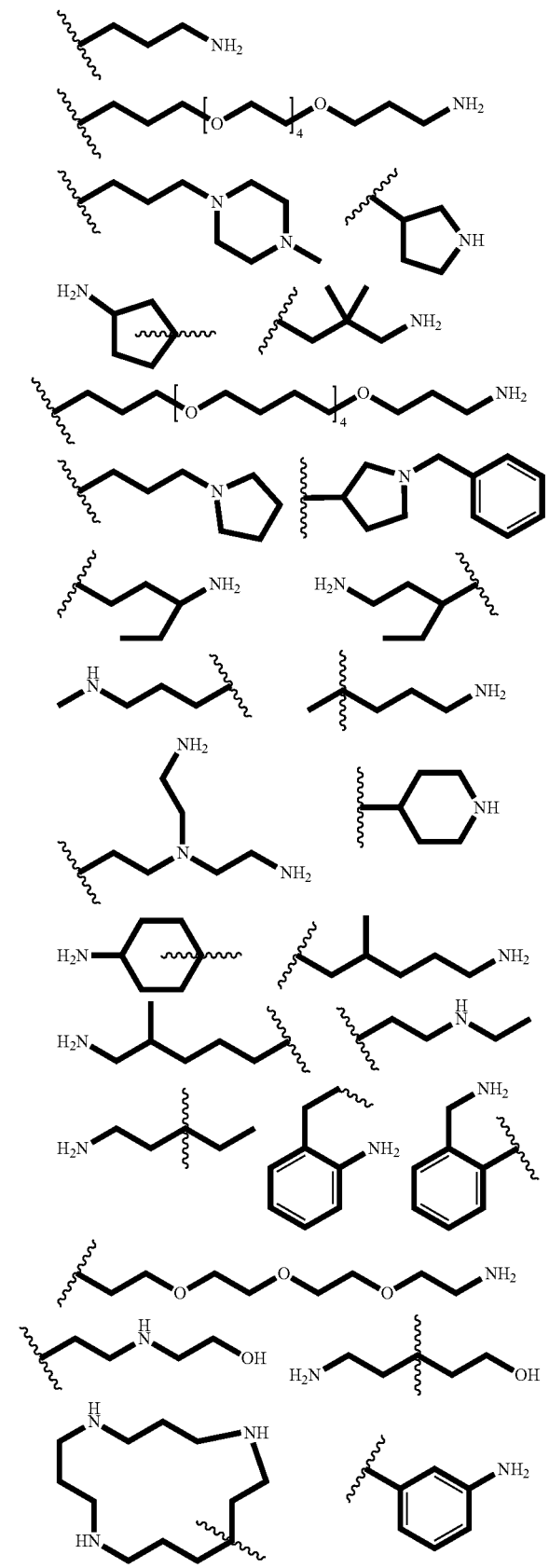

-continued
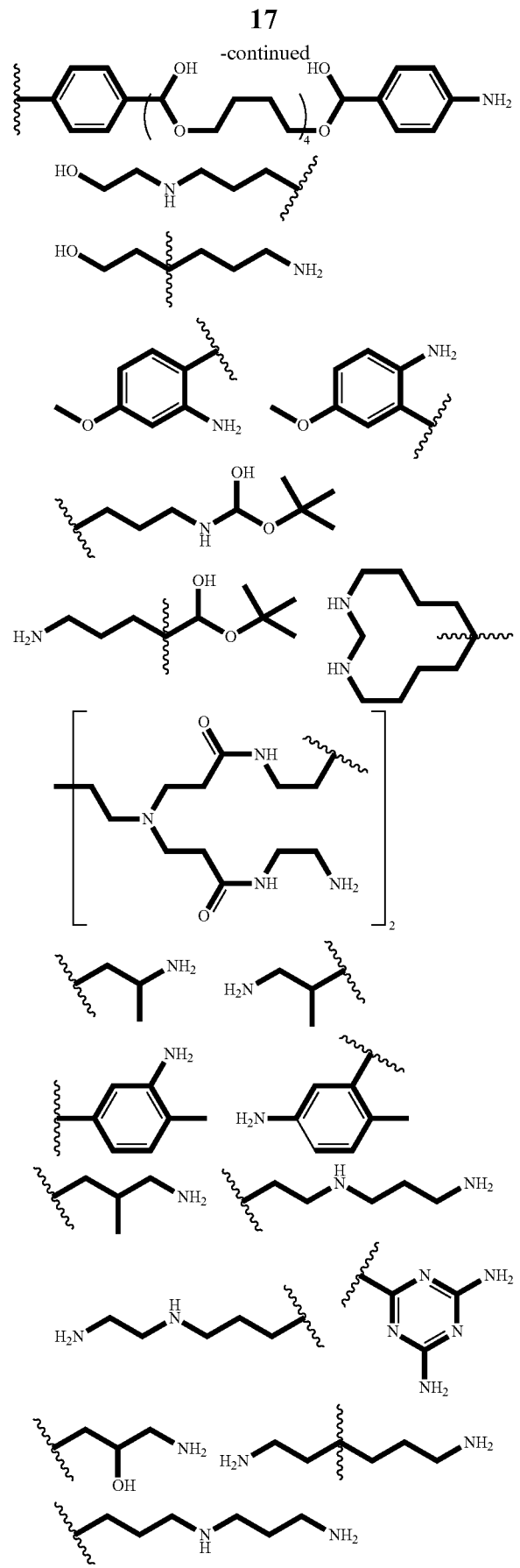
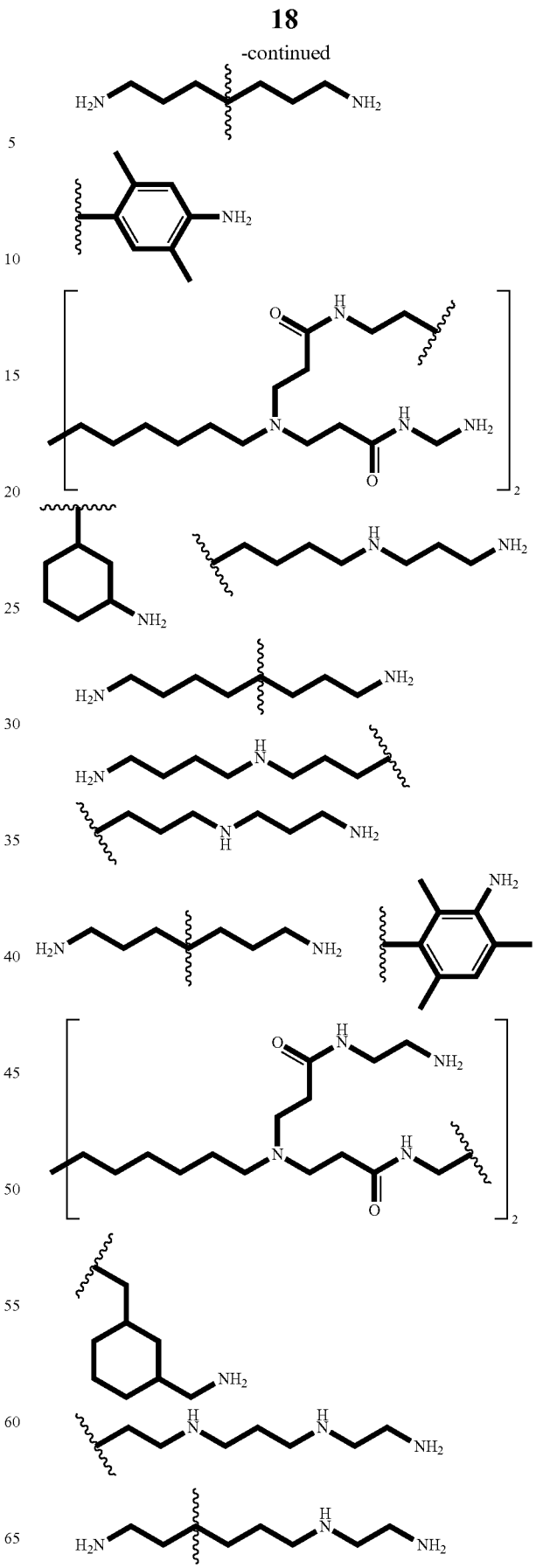

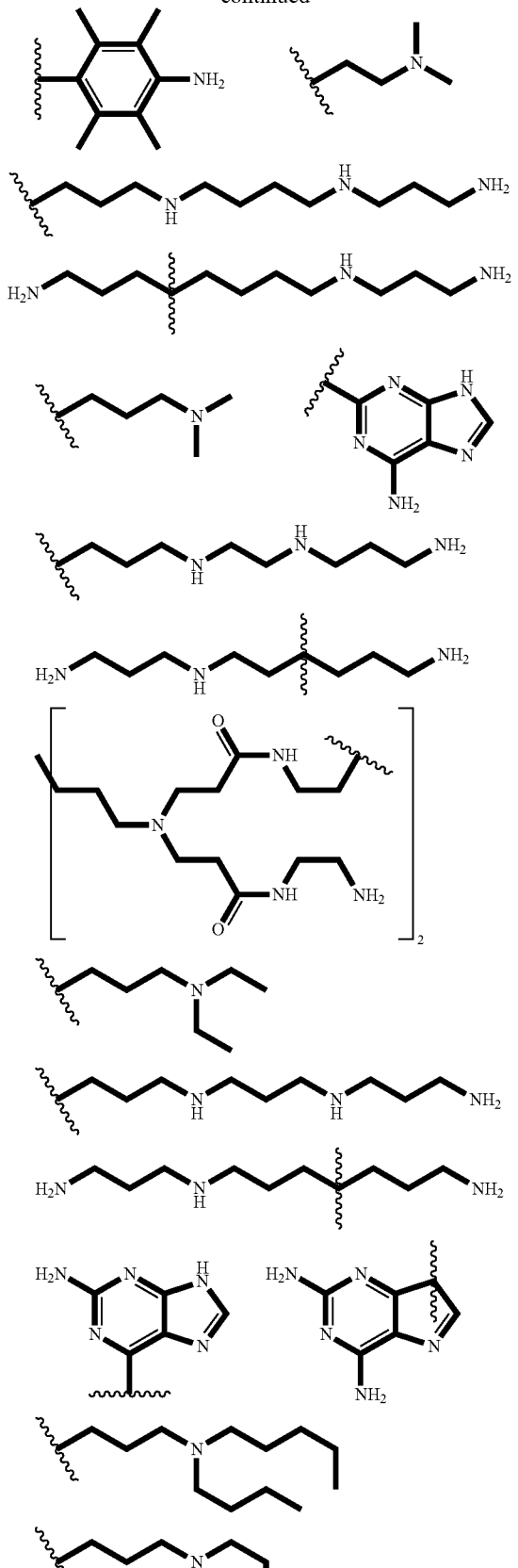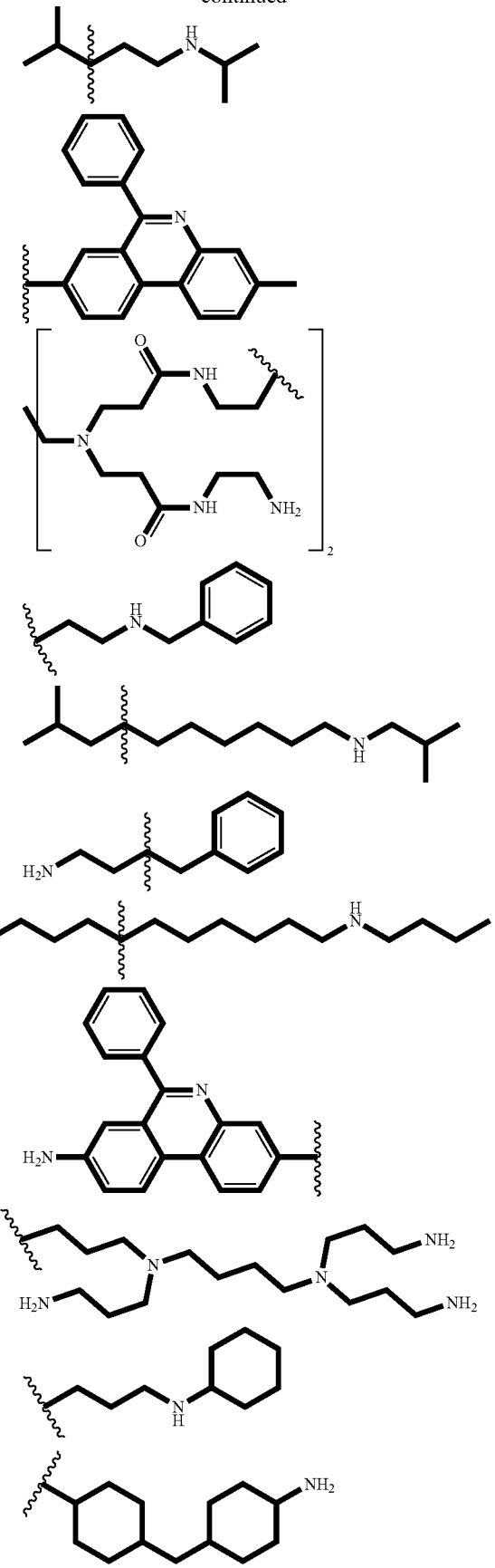

-continued

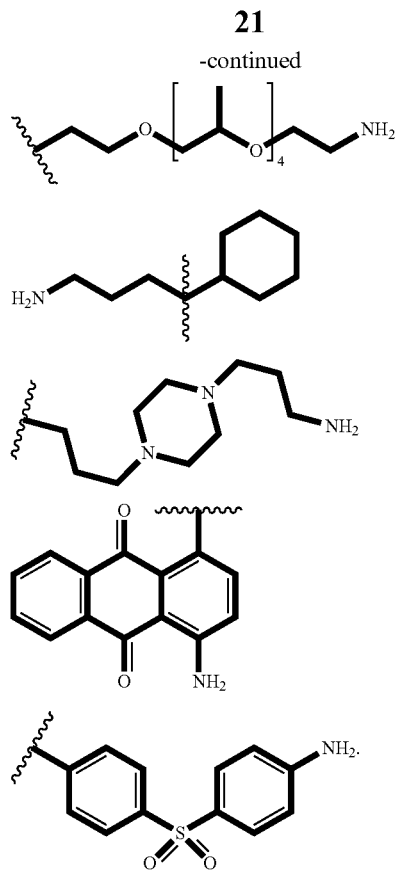

In particular embodiments, the PBAE is constructed with an end group monomer selected from:

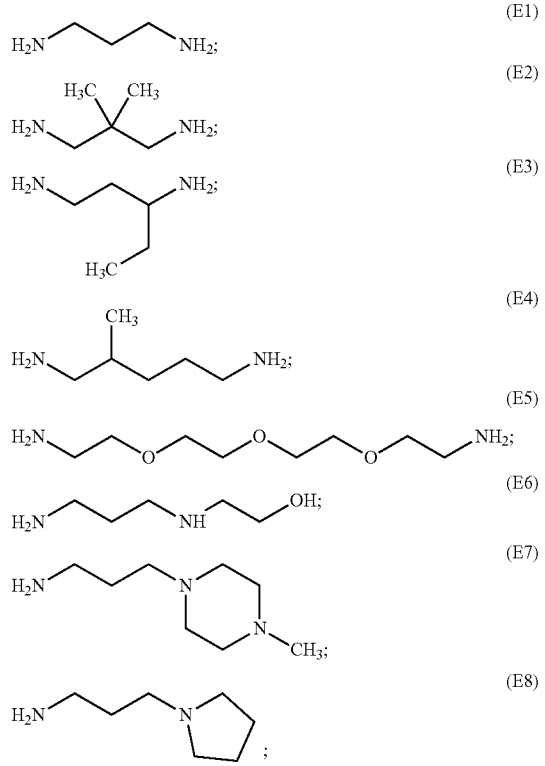

-continued

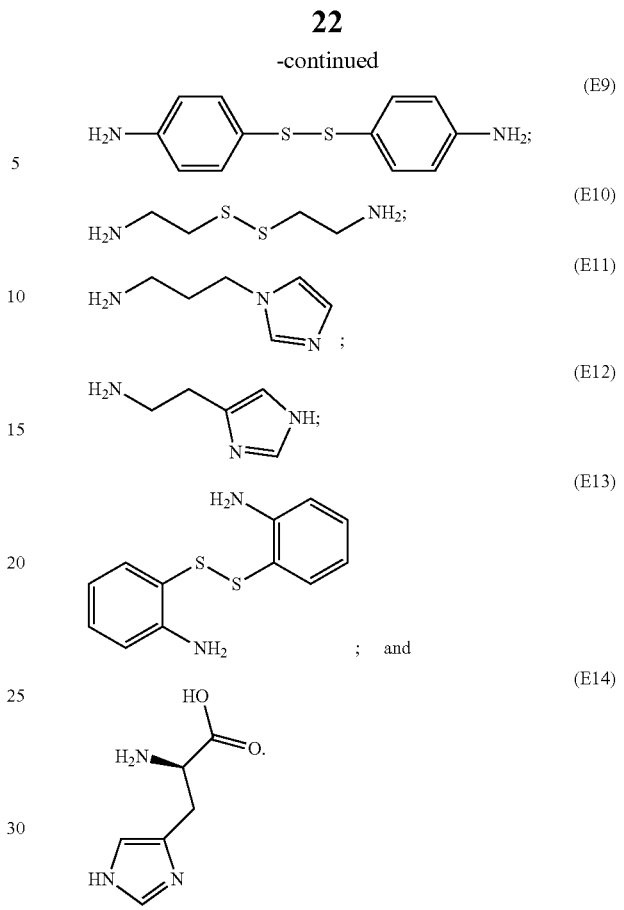

In particular embodiments, the presently disclosed subject matter provides a composition comprising a poly(beta-amino ester) (PBAE) of formula (I):

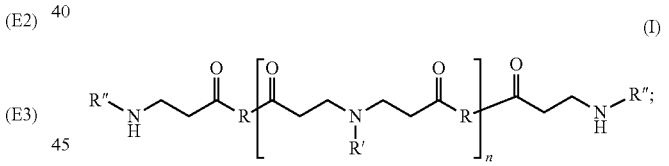

(I)

and a DNA plasmid comprising a nucleic acid sequence encoding SR39 thymidine kinase; wherein: n is an integer from 1 to 10,000; each R is independently selected from the group consisting of:

(B3)

(B4)

(B5)

-continued
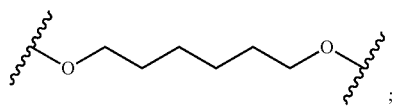 (B6)
each R' is independently selected from the group consisting of:
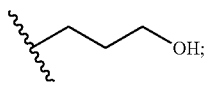 (S3)
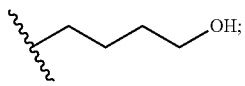 (S4)
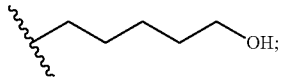 (S5)
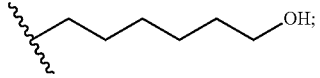 (S6)
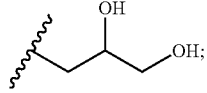 (S7)
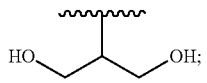 (S8)
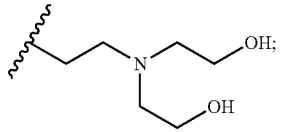 (S9)
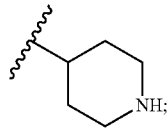 (S10)
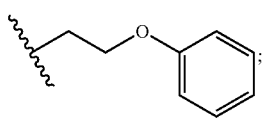 (S11)
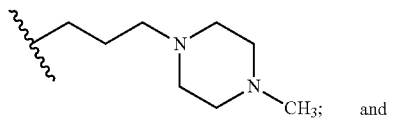 (S12)
and
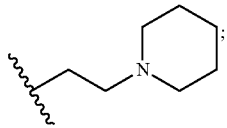 (S13)
each R" is independently selected from the group consisting of:
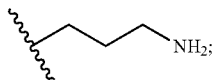 (E1)
 (E2)
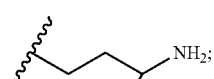 (E3)
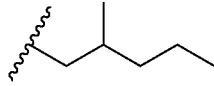 (E4)
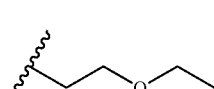 (E5)
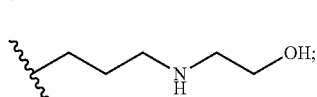 (E6)
 (E7)
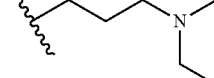 (E8)
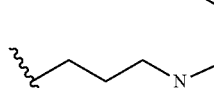 (E9)
 (E10)
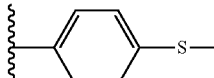 (E11)
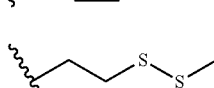 (E12)
 (E13)
and -continued

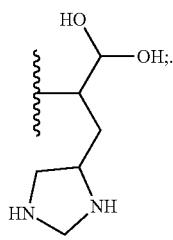
(E14)

In more particular embodiments, each R is independently selected from the group consisting of:

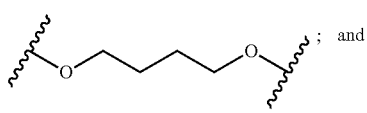
(B4) ; and

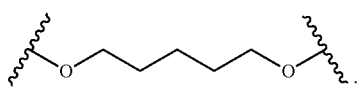
(B5)

In more particular embodiments, each R' is independently selected from the group consisting of:

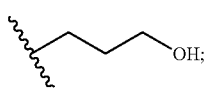
(S3)

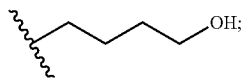
(S4)

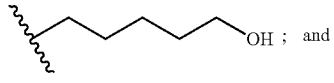
(S5) ; and

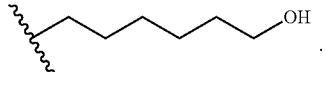
(S6)

In more particular embodiments, each R" is independently selected from the group consisting of:

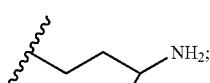
(E3)

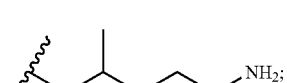
(E4)

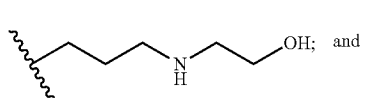
(E6) ; and

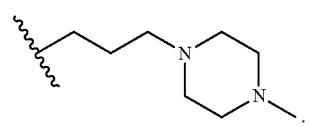
(E7)

In yet more particular embodiments, each R is independently selected from the group consisting of;

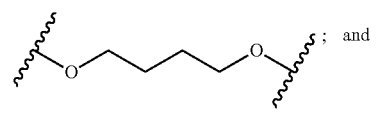
(B4) ; and

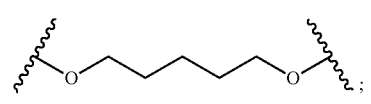
(B5) ;

each R' is independently selected from the group consisting of:

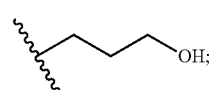
(S3)

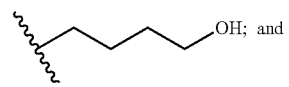
(S4) ; and

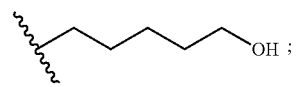
(S5)

and each R" is independently selected from the group consisting of:

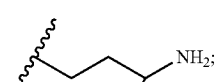
(E3)

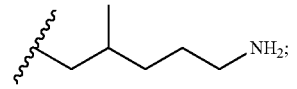
(E4)

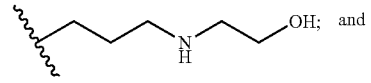
(E6) ; and

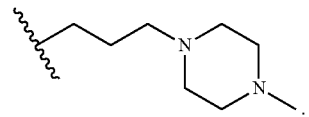
(E7)

In even more particular embodiments, a combination of R, R', and R" is selected from the group consisting of:

| Compound Code | R | R' | R'' |
|---|---|---|---|
| 446 | (B4) | (S4) | (E6) |
| 447 | (B4) | (S4) | (E7) |
| 453 | (B4) | (S5) | (E3) |
| 454 | (B4) | (S5) | (E4) |
| 456 | (B4) | (S5) | (E6) |
| 457 | (B4) | (S5) | (E7) |
| 534 | (B5) | (S3) | (E4) |
| 536 | (B5) | (S3) | (E6) |
| 537 | (B5) | (S3) | (E7) |
| 543 | (B5) | (S4) | (E3) |

-continued
| Compound Code | R | R' | R" |
|---|---|---|---|
| 544 | 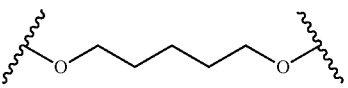 (B5) | 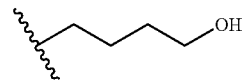 (S4) | 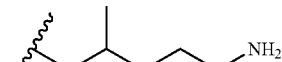 (E4) |
| 546 |  (B5) | 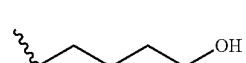 (S4) | 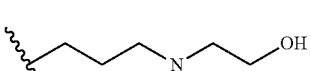 (E6) |
| 547 | 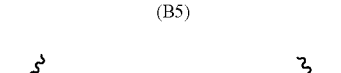 (B5) | 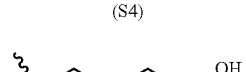 (S4) | 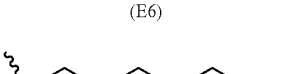 (E7) |
In even yet more particular embodiments, the PBAE of formula (I) is selected from the group consisting of:
446
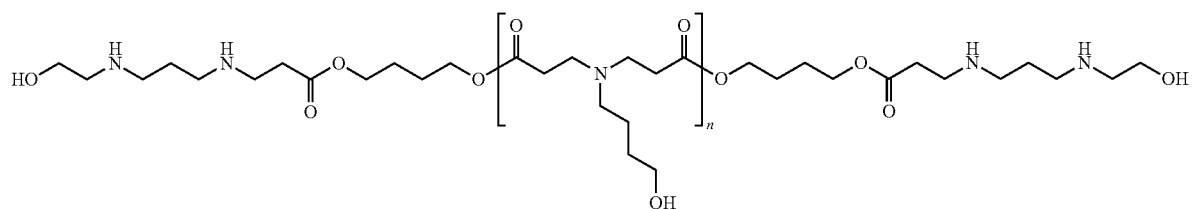
447
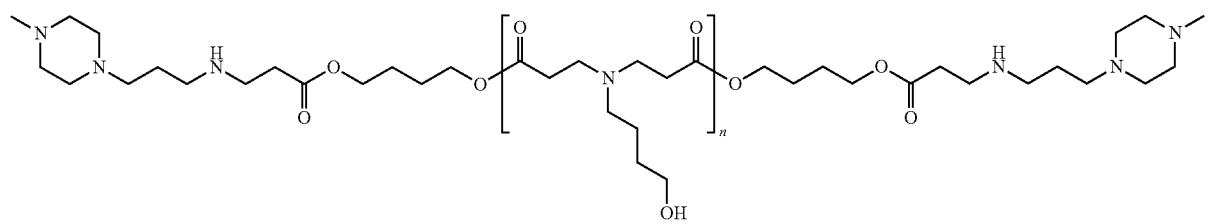
453
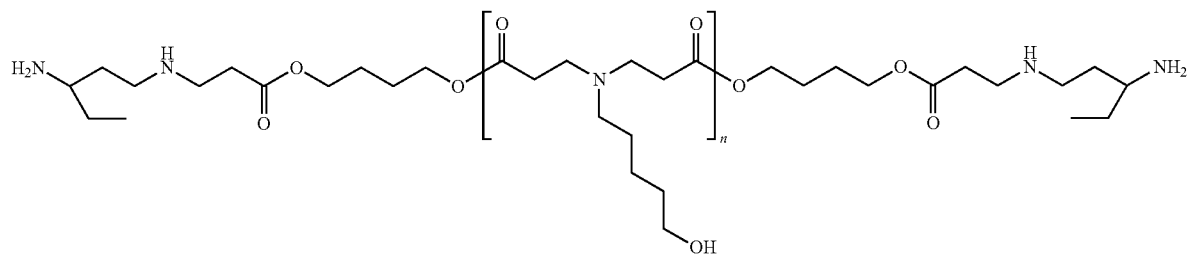

454
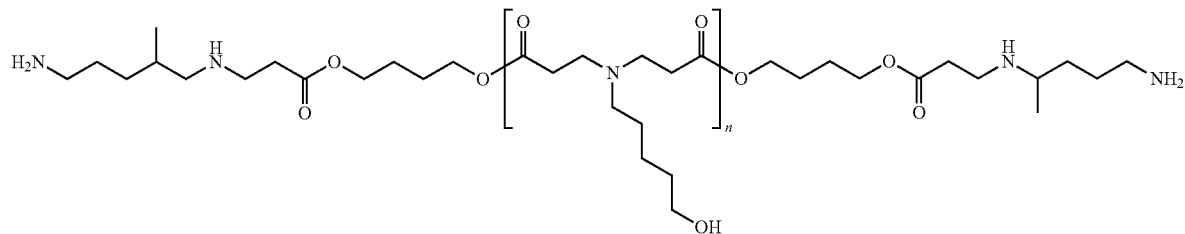
456
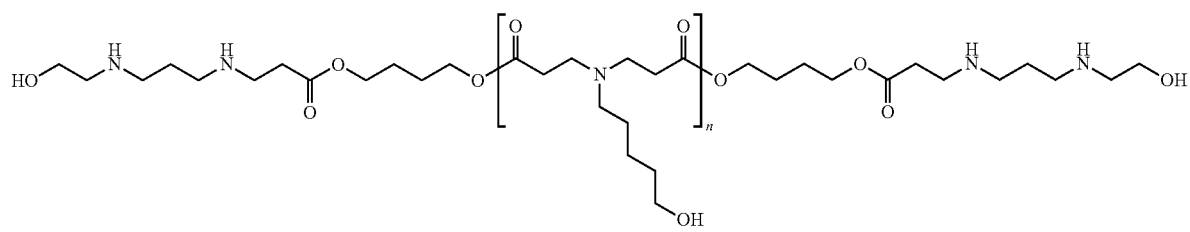
457
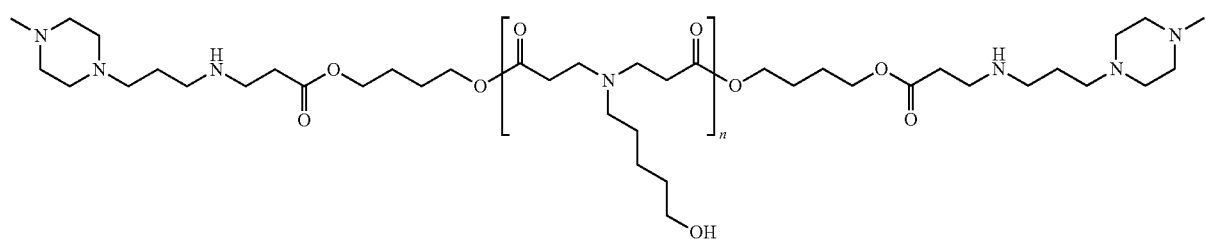
534
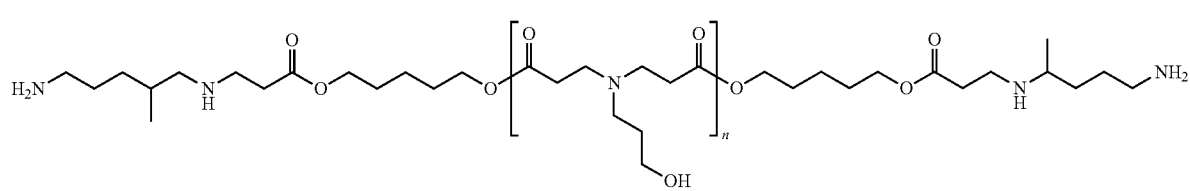
536
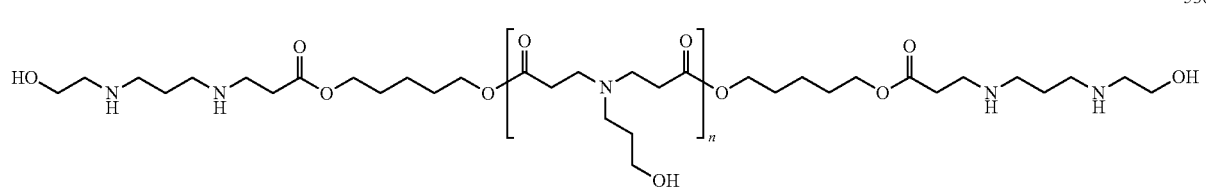
537
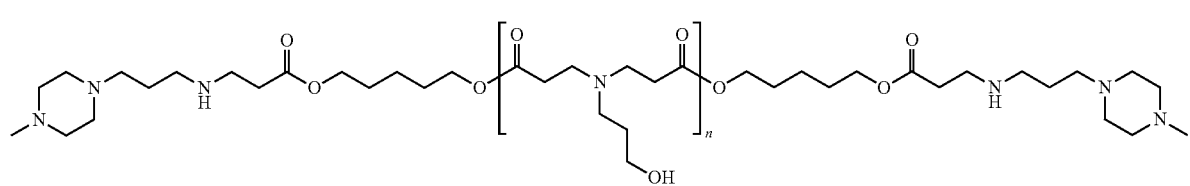
543
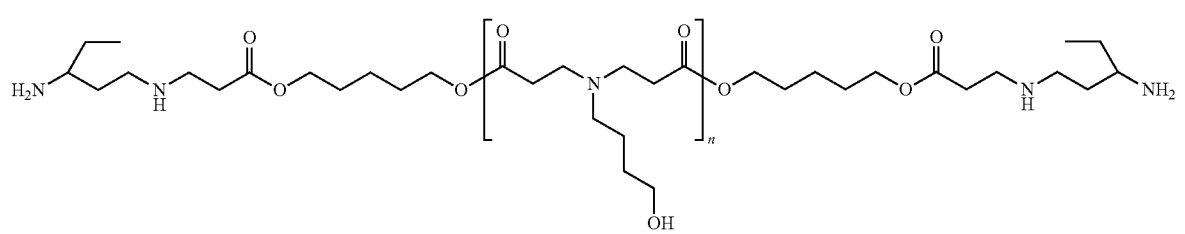

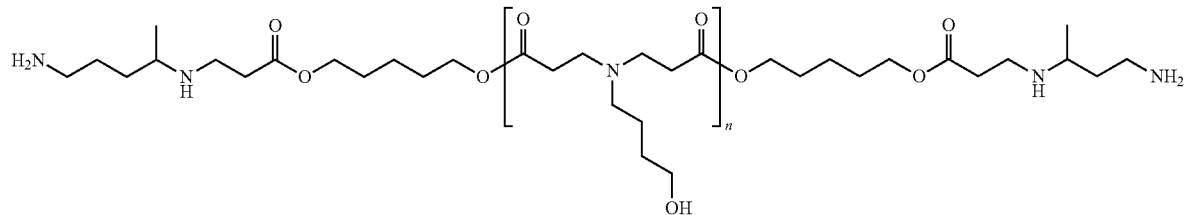

544

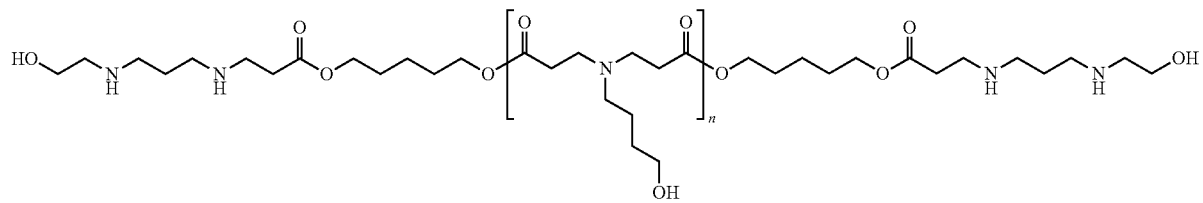

546

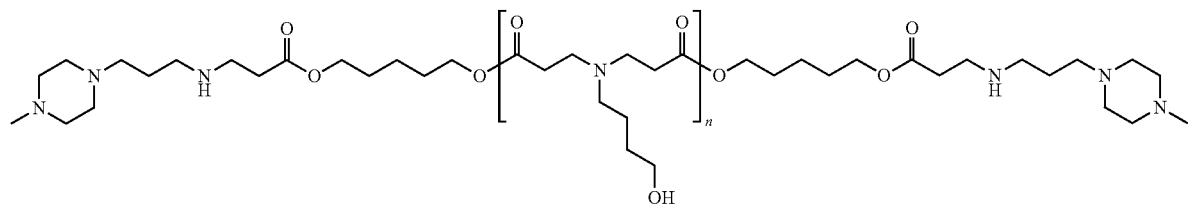

547

In certain embodiments, the PBAE of formula (I) is 547:

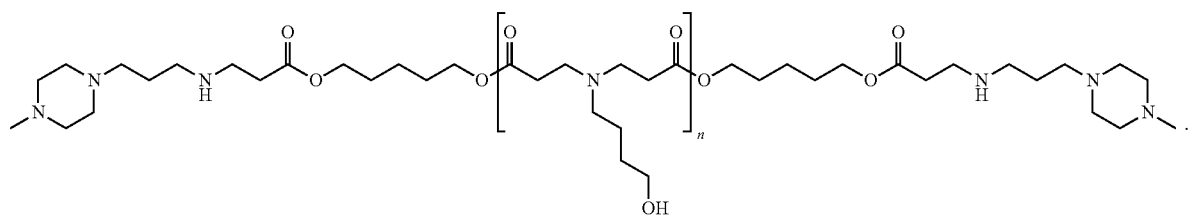

In some embodiments, n is selected from the group consisting of: an integer from 1 to 1,000; an integer from 1 to 100; an integer from 1 to 30; an integer from 5 to 20; an integer from 10 to 15; and an integer from 1 to 10.

In particular embodiments, the composition has a PBAE-to-DNA plasmid weight-to-weight ratio (w/w) selected from the group consisting of, in some embodiments, about 75 w/w to about 10 w/w, in some embodiments, about 50 w/w to about 20 w/w, in some embodiments, about 25 w/w, and, in some embodiments, about 50 w/w.

In certain embodiments, the linear and/or branched PBAE polymer has a molecular weight of from 5 to 10 kDa, or a molecular weight of from 10 to 15 kDa, or a molecular weight of from 15 to 25 kDa, or a molecular weight of from 25 to 50 kDa.

In certain embodiments, the presently disclosed subject matter provides a pharmaceutical formulation comprising the above-described nucleic acid molecule and a poly(beta-amino ester) (PBAE) of formula (I) in a pharmaceutically acceptable carrier.

As used herein, "pharmaceutically acceptable carrier" is intended to include, but is not limited to, water, saline, dextrose solutions, human serum albumin, liposomes, hydrogels, microparticles and nanoparticles. The use of such media and agents for pharmaceutically active compositions is well known in the art, and thus further examples and methods of incorporating each into compositions at effective levels need not be discussed here.

In particular embodiments, the pharmaceutical formulation further comprises one or more therapeutic agents. In yet more particular embodiments, the one or more therapeutic agents is ganciclovir (GCV) or valganciclovir:

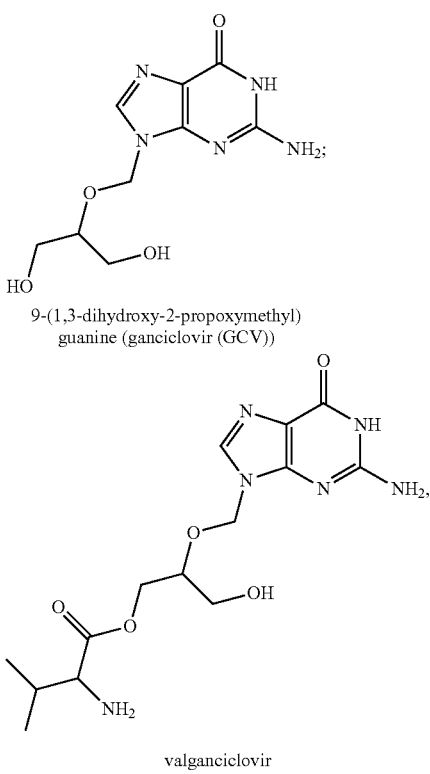

9-(1,3-dihydroxy-2-propoxymethyl) guanine (ganciclovir (GCV))

valganciclovir or another small molecule that is acted upon by the SR39 kinase to have a therapeutic effect.

In other embodiments, the pharmaceutical formulation further comprises one or more imaging agents. In particular embodiments, the one or more imaging agents is 9-(4-(18) F-fluoro-3-[hydroxymethyl]butyl) guanine ((18)F-FHBG), or another small molecule that is acted upon by the SR39 kinase to have a diagnostic effect.

In yet other embodiments, the pharmaceutical formulation further comprises a nanoparticle or microparticle of the PBAE of formula (I). The PBAE polymers in some embodiments can self-assemble with nucleic acid, including plasmid DNA, to form nanoparticles which may be in the range of 50 to 500 nm in size. In embodiments, the particle has at least one dimension in the range of about 50 nm to about 500 nm, or from about 50 to about 200 nm. Exemplary particles may have an average size (e.g., average diameter) of about 50, about 75, about 100, about 125, about 150, about 200, about 250, about 300, about 400 or about 500 nm. In some embodiments, the nanoparticle has an average diameter of from about 50 nm to about 500 nm, from about 50 nm to about 300 nm, or from about 50 nm to about 200 nm, or from about 50 nm to about 150 nm, or from about 70 to about 100 nm. In embodiments, the nanoparticle has an average diameter of from about 200 nm to about 500 nm. In embodiments, the nanoparticle has at least one dimension, e.g., average diameter, of about 50 to about 100 nm. Nanoparticles are usually desirable for in vivo applications. For example, a nanoparticle of less than about 200 nm will better distribute to target tissues in vivo.

In some embodiments, the presently disclosed particles may comprise other combinations of cationic polymeric blends or block co-polymers. Additional polymers include polycaprolactone (PCL), polyglycolic acid (PGA), polylactic acid (PLA), poly(acrylic acid) (PAA), poly-3-hydroxy-butyrate (P3HB), poly(hydroxybutyrate-co-hydroxyvalerate), and polyethylene glycol (PEG). In embodiments, a particle includes blends of other polymer materials to modulate a particle's surface properties. For example, the blend may include non-degradable polymers that are used in the art, such as polystyrene. Thus, in embodiments, a degradable polymer or polymers from above are blended to create a copolymer system. In yet other embodiments, the presently disclosed particle comprises a polymer blend of PBAE, e.g., a mixture of PBAE polymers.

In embodiments, the particles are spherical in shape. In embodiments, the particles have a non-spherical shape. In embodiments, the particles have an ellipsoidal shape with an aspect ratio of the long axis to the short axis between 2 and 10.

In certain embodiments, nanoparticles formed through the presently disclosed procedures that encapsulate active agents, such as DNA plasmid, are themselves encapsulated into a larger nanoparticle, microparticle, or device. In some embodiments, this larger structure is degradable and in other embodiments it is not degradable and instead serves as a reservoir that can be refilled with the nanoparticles. These larger nanoparticles, microparticles, and/or devices can be constructed with any biomaterials and methods that one skilled in the art would be aware. In some embodiments they can be constructed with multi-component degradable cationic polymers as described herein. In other embodiments, they can be constructed with FDA-approved biomaterials, including, but not limited to, poly(lactic-co-glycolic acid) (PLGA). In the case of PLGA and the double emulsion fabrication process as an example, the nanoparticles are part of the aqueous phase in the primary emulsion. In the final PLGA nano- or microparticles, the nanoparticles will remain in the aqueous phase and in the pores/pockets of the PLGA nano- or microparticles. As the microparticles degrade, the nanoparticles will be released, thereby allowing sustained release of the nanoparticles comprising the active agents. In particular embodiments, the nanoparticle or microparticle of the PBAE of formula (I) is encapsulated in a poly(lactic-co-glycolic acid) (PLGA) nanoparticle or microparticle.

In some embodiments, the presently disclosed subject matter also includes a method of using and storing the polymers and particles described herein whereby a cryoprotectant (including, but not limited to, a sugar) is added to the polymer and/or particle solution and it is lyophilized and stored as a powder. Such a powder is designed to remain stable and be reconstituted easily with aqueous buffer as one skilled in the art could utilize.

In certain embodiments, the nanoparticle targeting (through biomaterial selection, nanoparticle biophysical properties, and/or a targeting ligand) is combined with transcriptional targeting of a therapeutic gene to a particular cell type (e.g., cancer cells). Transcriptional targeting includes designing nucleic acid cargo which comprises a promoter that is active in cells or tissue types of interest so that the delivered nanoparticles express the nucleic acid cargo in a tissue-specific manner.

In particular embodiments, the presently disclosed particles carry plasmid DNA comprising a nucleic acid sequence encoding a SR39 thymidine kinase to a cancer cell. The cell may be a eukaryotic cell, such as an animal cell or plant cell. In further embodiments, the animal cell is a mammalian cell (e.g., a human cell). In some embodiments, the cell is transfected with the particles for ex vivo gene therapy. In some embodiments, the particles are delivered directly to an organism, such as mammalian subject, to thereby direct gene therapy in vivo.

In some embodiments, including for delivery of nucleic acids to cells ex vivo, the cell is a stem cell or progenitor cell. The cell may be multipotent or pluripotent. In some embodiments, the cell is a stem cell, such as an embryonic stem cell or adult stem cell. In some embodiments, the cell is a hematopoietic stem cell. In some embodiments, including for delivering nucleic acids to cells in vivo, the cell is a cancer cell or malignant cell.

For in vivo gene therapy, particles can be formulated for a variety of modes of administration, including systemic and topical or localized administration. Thus, the pharmaceutical compositions can be formulated for administration to patients by any appropriate route, including intravenous administration, intra-arterial administration, subcutaneous administration, intradermal administration, intralymphatic administration, and intra-tumoral administration. In some embodiments, the composition is lyophilized and reconstituted prior to administration.

B. Methods for Treating or Diagnosing a Cancer

In some embodiments, the presently disclosed subject matter provides a method for treating or diagnosing a cancer, the method comprising administering a composition or formulation comprising a nucleic acid molecule encoding a mutant TK protein and PBAE composition of formula (I) as described herein to a subject in need of treatment thereof.

Any suitable cancer may be treated or diagnosed using the methods described herein. A "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within a subject, or circulate in the blood stream as independent cells, for example, leukemic cells.

A cancer can include, but is not limited to, acute lymphocytic leukemia, acute myelogenous leukemia, angiosarcoma, basal cell carcinoma, bladder cancer, brain cancer (e.g., gliomas), breast cancer, cervical cancer, choriocarcinoma, colon cancer, colorectal cancer, corpus uteri cancer, endocrine cancer, esophageal cancer, Ewing's Sarcoma, eye or ocular cancer, gastrointestinal cancer, head cancer, head and neck cancer, hemangioendothelioma, hemangiomas, hepatocellular carcinoma (HCC), Kaposi's Sarcoma, larynx cancer, leukemia/lymphoma, liver cancer, lung cancer, lymphoma, lymphangiogenesis, melanoma, mouth/pharynx cancer, neck cancer, neuroblastoma, neurofibromatosis, oral cancer, ovarian cancer, pancreatic cancer, prostate cancer, rectal cancer, renal cancer, rhabdomyosarcoma, stomach cancer, skin cancer, small cell lung cancer, squamous cell carcinoma, testicular cancer, throat cancer, tuberous sclerosis, urinary cancer, uterine cancer, Wilms Tumor, benign and malignant tumors, and adenomas.

In some embodiments, the cancer is hepatocellular carcinoma (HCC) or prostate cancer.

In certain embodiments, the presently disclosed method further comprises administering to the subject one or more therapeutic agents simultaneously or sequentially with the PBAE composition of formula (I) or a formulation thereof. In particular embodiments, the one or more therapeutic agents is ganciclovir (GCV) or valganciclovir.

In other embodiments, the presently disclosed method further comprises administering to the subject one or more imaging agents simultaneously or sequentially with the PBAE composition of formula (I) or a formulation thereof. In particular embodiments, the one or more imaging agents is 9-(4-(18)F-fluoro-3-[hydroxymethyl]butyl) guanine ((18)F-FHBG).

In such embodiments, the presently disclosed method further comprises acquiring an image. In particular embodiments, the image is a positron emission tomography (PET) image.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

As used herein, the term "inhibit," and grammatical derivations thereof, refers to the ability of a presently disclosed compound, e.g., a presently disclosed compound of formula (I), to block, partially block, interfere, decrease, or reduce the growth and/or metastasis of a cancer cell. Thus, one of ordinary skill in the art would appreciate that the term "inhibit" encompasses a complete and/or partial decrease in the growth and/or metastasis of a cancer cell, e.g., a decrease by at least 10%, in some embodiments, a decrease by at least 20%, 30%, 50%, 75%, 95%, 98%, and up to and including 100%.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of formula (I) and at least one therapeutic agent and/or imaging agent. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of formula (I) described herein can be administered alone or in combination with adjuvants that enhance stability of the compounds of formula (I), alone or in combination with one or more therapeutic agents and/or imaging agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of formula (I) and at least one additional therapeutic agent can be varied so long as the beneficial effects of the combination of these agents are achieved. Accordingly, the phrase "in combination with" refers to the administration of a compound of formula (I) and at least one additional therapeutic agent either simultaneously, sequentially, or a combination thereof. Therefore, a subject administered a combination of a compound of formula (I) and at least one additional therapeutic agent can receive compound of formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) and at least one additional therapeutic agent are administered simultaneously, they can be administered to the subject as separate pharmaceutical compositions, each comprising either a compound of formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index(SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

C. Kits

In some embodiments, the presently disclosed subject matter provides a kit. In general, the presently disclosed kit contains some or all of the components, reagents, supplies, and the like to practice a method according to the presently disclosed subject matter.

More particularly, the presently disclosed kit comprises the nucleic acid molecule described herein, e.g., a CMV-SR39 or AFP-SR39 plasmid, or derivatives thereof, either alone or as part of a composition comprising a PBAE of formula (I). In some embodiments, the kit includes a transfection reagent, including, but not limited to, a polymer, a lipid, a nanoparticle, or an electroporation/nucleofection solution. In some embodiments, the kit further comprises one or more therapeutic agents. In particular embodiments, the one or more therapeutic agents is ganciclovir (GCV) or valganciclovir.

In other embodiments, the kit further comprises one or more imaging agents. In particular embodiments, the one or more imaging agents is 9-(4-(18)F-fluoro-3-[hydroxymethyl]butyl) guanine ((18)F-FHBG).

In certain embodiments, the kit further comprises one of more of multiple dosage units of the composition, a pharmaceutically acceptable carrier, a device for administration of the composition, instructions for use, and combinations thereof.

D. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

Further, as used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 µm). In such embodiments, the particle also can be referred to as a "microparticle. Thus, the term "microparticle" includes particles having at least one dimension in the range of about one micrometer (µm), i.e., $1\times10^{-6}$ meters, to about 1000 µm. The term "particle" as used herein is meant to include nanoparticles and microparticles.

It will be appreciated by one of ordinary skill in the art that nanoparticles suitable for use with the presently disclosed methods can exist in a variety of shapes, including, but not limited to, spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes. In particular embodiments, the presently disclosed nanoparticles have a spherical shape.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Biocompatible": The term "biocompatible", as used herein is intended to describe compounds that are not toxic to cells. Compounds are "biocompatible" if their addition to cells in vitro results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

"Peptide" or "protein": A "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., C$_{1-10}$ means one to ten carbons, including 1, 2, 3, 4, 5, 6, 7, 8, 9, and 10 carbons). In particular embodiments, the term "alkyl" refers to C$_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_{1-8}$ straight-chain alkyls. In other embodiments, "alkyl" refers, in particular, to C$_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "heteroalkyl," by itself or in combination with another term, means, unless otherwise stated, a stable straight or branched chain having from 1 to 20 carbon atoms or heteroatoms or a cyclic hydrocarbon group having from 3 to 10 carbon atoms or heteroatoms, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkylene moiety, also as defined above, e.g., a $C_{1-20}$ alkylene moiety. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated hydrocarbon has one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{2-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$), —CH—CH═CH—CH; —CH═CH—CH$_2$—; —CH$_2$CH$_2$CH$_2$CH$_2$—, —CH$_2$CH═CHCH$_2$—, —CH$_2$CsCCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

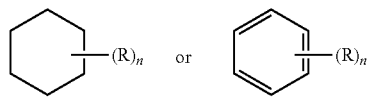

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

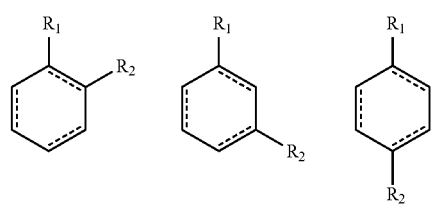

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⌇ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO₂R', —C(O)NR'R", —OC(O)NR'R", —NR"C(O)R', —NR'—C(O)NR"R'", —NR"C(O)OR', —NR—C(NR'R")=NR'", —S(O)R', —S(O)₂R', —S(O)₂NR'R", —NRSO₂R', —CN, CF₃, fluorinated $C_{1-4}$ alkyl, and —NO₂ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR"", —NR—C(NR'R")=NR'''—S(O)R', —S(O)$_2$R', —S(O)$_2$NR'R", —NRSO$_2$R', —CN and —NO$_2$, —R', —N$_3$, —CH(Ph)$_2$, fluoro(C$_{1-4}$)alkoxo, and fluoro(C$_{1-4}$)alkyl, in a number ranging from zero to the total number of open valences on aromatic ring system; and where R', R", R''' and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl)acetyl- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The term "cyano" refers to the —C≡N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

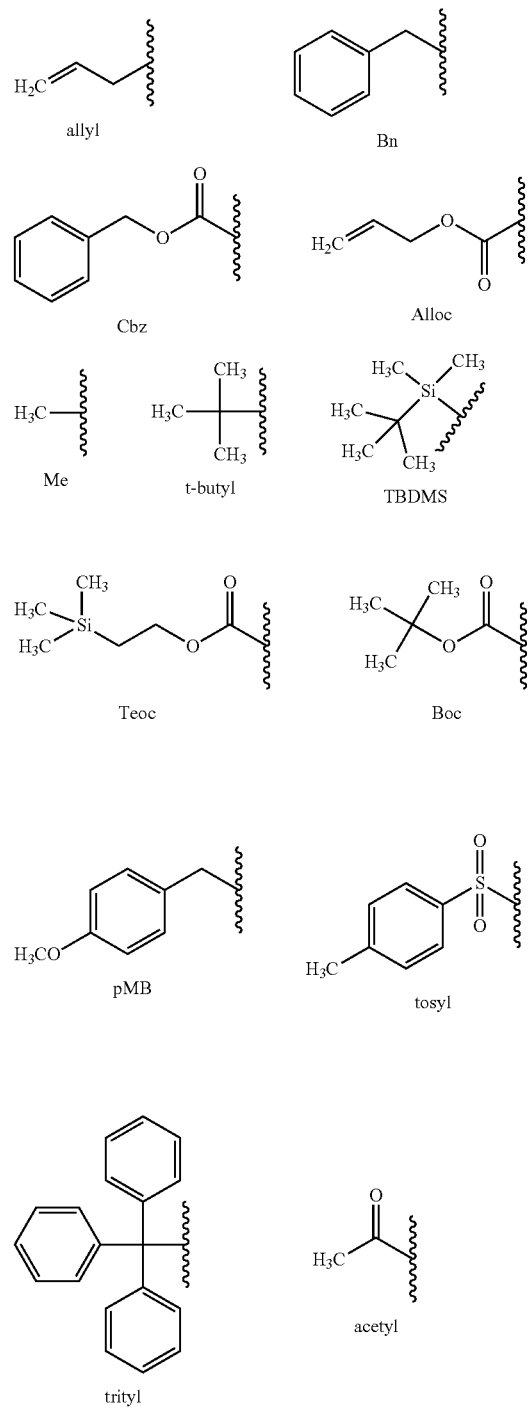

-continued

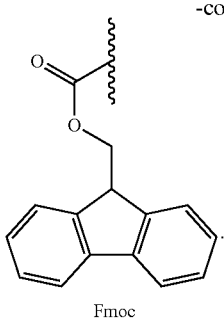

Fmoc

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

CpG-Free CMV-SR39 and AFP-SR39

1.1 Background

Hepatocellular carcinoma (HCC) is the third most common cause of cancer deaths worldwide and has the fastest growing mortality rate in the United States. See Tanaka et al., 2006. The majority of HCC cases arise from preexisting chronic liver conditions, such as hepatitis B or C viral infections, and underlying disease causes significant damage to the liver, putting HCC patients at risk for liver failure. See El-Serag et al., 2008. The vast majority of patients are not eligible for curative treatments, such as surgical resection and liver transplantation. Other therapeutic modalities, including chemotherapy, radiation, and trans arterial chemoembolization, are largely palliative and cancer recurrence is common. See Arzumanyan et al., 2013. Accordingly, an urgent need exists for a highly cancer-specific therapeutic to treat HCC malignancies while minimizing cytotoxicity to the liver parenchyma.

Gene therapies provide control over cellular functions and can induce a wide range of therapeutic effects. Viruses have traditionally served as the delivery vehicle for gene therapies and have shown clinical promise due to high efficiency of in vivo transfection. See Wang et al., 2000; Nathwani et al., 2011. However, there are concerns regarding the safety of viruses, as they can be highly immunogenic and have the potential to cause cancer from insertional mutagenesis. See Marshall 1999; Check 2002.

Nanoparticle gene delivery is a promising non-viral option, offering preferential delivery of cargos to tumor sites by passive targeting via the enhanced permeation and retention effect. Iyer et al., 2006. Nanoparticles also provide protection for cargo in circulation and can be engineered for controlled release at the desired site, for example in the tumor microenvironment or inside a cancer cell. See Karlsson et al., 2018; Riley and Vermerris, 2017. Therefore, nanoparticles have been extensively explored for cancer-specific gene therapy.

Poly beta amino esters (PBAEs) are biodegradable cationic polymers which self-assemble with plasmid DNA to form polyplex nanoparticles. See Anderson et al., 2005. PBAE structures can be modified by combining different backbone, sidechain, and endcap monomers, affecting the chemical and physical properties of the resulting nanoparticles and influencing transfection efficiency. See Kim et al., 2013; Sunshine et al., 2011. Further, certain nanoparticle formulations have been shown to selectively transfect cancer cells over healthy cells. See Tzeng et al., 2013; Tzeng et al., 2011. Recent work has demonstrated this biomaterial-mediated specificity in liver cancer cells, suggesting that a PBAE gene delivery platform may facilitate targeted gene delivery to HCC tumors. See Zamboni et al., 2017.

A well-characterized therapeutic gene is the Herpes Simplex Virus-1 Thymidine Kinase (HSV1-TK). See Dey and Evans, 2011. This therapy involves inducing HSV1-TK expression in cancer cells, then systemically administering the prodrug ganciclovir (GCV). This small molecule drug is monophosphorylated by HSV1-TK, then endogenous cellular kinases further phosphorylate the compound. The triphosphate form of GCV is a toxic DNA polymerase inhibitor which induces apoptosis, particularly in rapidly dividing cancer cells. One mutant form of HSV1-TK, termed SR39, has demonstrated enhanced enzymatic activity over the wild-type form, resulting in an approximately 100-fold more potent therapeutic effect. See Black et al., 2001. SR39 is a theranostic treatment, indicating that it can simultaneously serve therapeutic and diagnostic functions. The SR39 kinase phosphorylates radiotracer F(18)-HBG and causes intracellular accumulation of radioactive fluorine, which can be imaged using Positron Emission Tomography (PET) to monitor SR39 expression within a tumor. Therefore, treatment with SR39 and GCV causes a toxic therapeutic effect while treatment with SR39 and [$^{18}$F]-FHBG enables diagnostic monitoring.

Genetic changes in cancer cells drive abnormal gene expression and upregulate activity of cancer-specific transcription factors. In HCC, alpha-feto protein (AFP) is expressed in 80% of tumors but is not expressed in healthy adult tissues. See Lan et al, 1997. Therefore, placing a therapeutic gene under the control of an AFP promoter restricts its expression to AFP-producing HCC cells and reduces off-target toxicity. This transcriptional targeting strategy has been successfully employed in viral HSV1-TK therapies for HCC. See Ido et al., 1995.

1.2 Overview

The presently disclosed subject matter provides a novel gene delivery system for selective expression of the theranostic SR39 gene in AFP-producing HCC cells. To achieve a high degree of targeting, two distinct targeting modalities were incorporated into a nanoparticle gene delivery platform: (1) therapeutic DNA was packaged into biodegradable PBAE nanoparticles with biomaterial-mediated HCC-targeting properties; and (2) the gene cargo was engineered for transcriptional targeting of HCC cells using a cancer-specific promoter (see FIG. 1). Further, the gene cargo was manipulated to remove all CpG dinucleotide sequences, which has been shown to reduce immunogenicity and increase the duration of gene expression in vivo. See Hyde et al., 2008. The resulting therapy offers highly targeted and effective diagnostic and therapeutic treatment in HCC cells.

1.3 Materials and Methods 1.3.1. Cell Culture

SK-HEP-1, Hep-3B, PC-3 and THLE-3 cells were purchased from the ATCC cell bank and cultured according the company's specifications for each line. Huh-7 cells were kindly provided by Dr. Tran's Lab at Johns Hopkins University and grown in high-glucose DMEM with 10% heat-inactivated FBS and 1% penicillin-streptomycin. For in vitro experiments, cells were seeded at a density of 2,500-10,000 cells per well depending on the length of the individual experiment in tissue culture-treated 96-well plates 24 hours before transfections with NPs.

1.3.2. Plasmid Synthesis 1.3.2a. CpG Free SR39

The 1131 base pair sequence of the wild type herpes simplex virus (type 1/strain RH2) thymidine kinase gene, obtained from the European Nucleotide Archive, was modified to produce the SR39 mutant, see Black et al., 2001, in which Leu, Ile, Phe, Ala, and Leu residues are replaced with Ile, Phe, Leu, Phe, and Met in the amino acid positions 159, 160, 161, 168 and 169, respectively. Next, in order to eliminate all 2'-Deoxyribo (cytidine-phosphateguanosine) (CpG) dinucleotides within the SR39 gene, CpG-creating codons, i.e., containing a CpG or forming a CpG with the preceding or succeeding codons, were replaced with non-CpG-creating synonyms by following the degenerate human genetic code. The selection of the synonymous triplet substituting a CpG-creating codon was based on the Codon Usage Tabulated from GenBank (CUTG) and always prioritized synonyms with higher frequency of occurrence in humans. In order to ensure that changes in codons did not cause changes in the amino acid sequence, the final CpG free SR39 gene was translated into its amino acid counterpart with the Addgene sequence analyzer tool, and the amino acid residues were then compared to the original SR39's. A 10 nucleotide construct containing the ScaI (5'-AGTACT-3') restriction endonuclease cutting site, and a 10 nucleotide sequence containing the NheI (5'-GCTAGC-3') restriction site were designed to flank the 5' and 3' ends of the gene, respectively. This initial construct was sent to Integrated DNA Technologies (IDT) for custom gene synthesis, and the product delivered as a circularized plasmid carrying ampicillin resistance. A 10-nucleotide overhang containing the ApaLI (5'-GTGCAC-3') restriction site was subsequently incorporated into the 5' end by PCR using FP: AAT-TCTGTGCACAGCTTAGACCAGTACTAT and RP: TGCTTATGCTTATATGGCTAATGCTAGCTC as primers and the Q5 High-fidelity 2× Master Mix (NEB catalog #M0492S). The restriction sites were chosen on basis of: (1) presence of the cutting site, a single time, on the recipient vector for subcloning (pCpGfree-vitroNmcs from Invivogen; catalog #pcpgvtn-mcsg2), (2) absence of the cutting site within the CpG free SR39 gene, (3) commercial availability, (4) compatibility between 5' and 3' endonucleases regarding digestion buffer and temperature, and (5) availability of high-fidelity options. Geneious 8.0.4 (Biomatters) was employed throughout the plasmid design process. The 5488-base pair vector and 1187 base pair insert (PCR product containing an ApaLI overhang) were separately double digested with the restriction enzymes ApaLI (NEB catalog #R0507S) and NheI-HF (NEB catalog #R3131S) following the manufacturer's protocol. The digested DNA products were stained with ethidium bromide, separated by gel electrophoresis, and visualized under UV light. Fragments with the predicted vector and insert sizes were then excised from the agarose gel. Subsequently, vector and insert were separately recovered using the QIAquick Gel Extraction Kit (Qiagen catalog #28704) following the manufacturer's protocol, except for the use of water rather than elution buffer to elute DNA from columns. DNA concentration from extraction products was assessed with Nano-Drop 2000 Spectrophotometer (Thermo Scientific), and ligation was carried out at a 1 to 7 vector to insert ratio, each at a 100 ng/µL. These parameters were chosen to overcome the difficulties related to the low transformation efficacy of the applied bacteria strain. T4 DNA Ligase and buffer (NEB catalog #M0202S) were mixed with DNA at 4° C. before the 10 µL ligation reaction could proceed at 16° C. overnight. ChemiComp GT115 *E. coli*, acquired frozen from Invivogen (catalog #gt115-11), were transformed via heat shock using 54, of the ligation product. Bacteria were allowed to grow in 450 µL of SOC outgrowth medium (NEB catalog #B9020S) for 1 hour at 37° C. The full 500 µL of the bacteria suspension was streaked in an LB agar plate with kanamycin at 50 µg/mL. The plate was placed in a 37° C. dark incubator for 14 hours. A single colony was then harvested and bacteria allowed to grow for additional 8 hours in LB Broth (Quality Biological catalog #340-004-101). QIAprep Spin Miniprep Kit (Qiagen catalog #27104) was used to isolate plasmid DNA, which was then sent for DNA sequencing (Sanger Method).

1.3.2b. CpG Free AFP SR39

The 2144 base pair composite AFP enhancer and promoter sequence, obtained from the pDRVE-AFP-hAFP plasmid (Invivogen catalog #pdrive-afphafp), was evaluated for putative transcription factor binding sites using the TRANSFAC database (version 8.3) through the PROMO website. See Farre et al., 2003; Messeguer et al., 2002. A 95% similarity between predicted regulatory site and transcription factor matrix was the established threshold for a hit to be reported. CpG sequences within the AFP enhancer and promoter sequence were identified (total of 6) and modified according to the following strategies: (1) only one nucleotide was replaced within each CpG dinucleotide and their purine or pyrimidine identity was maintained, i. e., cytosines were replaced by thymidines and guanines by adenines, (2) the selection of cytosine or guanine for substitution was based on the distribution of regulatory sites. For example, if one of the two CpG nucleotides were shown to be part of a transcription factor binding site, this nucleotide was maintained and the other was replaced. In the AFP promoter and enhancer, there were no cases in which both nucleotides were identified as being a part of predicted transcription factor binding sites. Next, a designed construct consisting of the CpG free SR39 gene was added to the 3' end of the CpG free AFP sequence. Also, a 1520 base pair sequence, corresponding to base pairs 4403 to 435 of the pCpGfree-vitroNmcs vector and containing the EcoRI restriction site, was added to the 5' end of the CpG free AFP sequence. This entire construct was then sent for custom synthesis by Genscript. EcoRI was selected as the restriction endonuclease binding site at the insert's 5' position due to the fact that it was the only suitable restriction site 5' from the vector's composite promoter (mouse CMV promoter and human EF1 enhancer), and, digestion in this position guaranties the elimination of these original regulatory sequences from the vector. Double digestion with EcoRI-HF (NEB catalog #R3101S) and NheI-HF was carried out separately for vector and insert. The linearized digestion products were then identified by gel electrophoresis and UV light exposure, and recovered by gel extraction as described in the previous session. Vector and insert were ligated in a 10 µL reaction with T4 DNA Ligase/buffer at a 1 to 7 vector to insert ratio. ChemiComp GT115 *E. coli* transformation was carried out with 5 µL of ligation product applying the heat shock method, followed by one-hour incubation at 37° C. in 450 µL of SOC outgrowth medium. Bacteria were seeded (full 500 µL suspension volume) in LB agar plate with kanamycin at 50 µg/mL and allowed to grow for 24 hours at 37'C. The subsequent steps followed the same protocol described above for the CpG free SR39 gene.

1.3.3. Polymer Synthesis

The polymer 536 was synthesized through a two-step method. First, the sidechain monomer S3 [3-amino-1-propanol (Alfa Aesar)] was added to the backbone monomer B5 [1,5-pentanediol diacrylate (Monomer-Polymer and Dajac Labs, Trevose, Pa.)] at a 1.1:1 ratio and the reaction was placed in a magnetic stirrer at 90° C. After 24 hours, THS-dissolved end-capping monomer E6 [2-(3-aminopropylamino)ethanol (Sigma-Aldrich, St. Louis, Mo.)] was added to the reaction at a 10-fold excess and the solution stirred in room temperature for 1 hour. Ether was used to precipitate the resulting polymer and vacuum to remove ether excess. Anhydrous DMSO was utilized to dissolve the polymer, which was then kept frozen (−20° C.) and protect from humidity until use. For a detailed explanation on the synthesis process, please refer to our previous publication. See Zamboni et al., 2017.

1.3.4. Polymer Analysis

The structure of the polymer 2-((3-aminopropyl)amino) ethanol end-modified poly(1,5-pentanediol diacrylate-co-3-amino-1-propanol), referred to as "536" for the sake of simplicity, was analyzed by proton nuclear magnetic resonance ($^1$H-NMR; Bruker Avance III 500 MHz NMR spectrometer in CDCl 3) and gel permeation chromatography (GPC; Waters 2414 Refractive Index Detector, Milford, Mass.). For GPC, number average ($M_n$), weight average ($M_w$), and polydispersity (PDI) were measured relatively to monodisperse polystyrene standards.

1.3.5. Nanoparticle Synthesis and Transfection In Vitro

Plasmid and polymer were separately dissolved in a 25 mM solution of sodium acetate (pH=5) and these solutions mixed at a 25 polymer-to-DNA weight-to-weight (w/w) ratio, herein referred to as 25 w/w ratio. NPs were allowed to form for 10 minutes in room temperature and 20 µL of the NP solution, containing 30 ng/µL of DNA, was added to a cell monolayer in 100 µL of culture media.

1.3.6. Analysis of Nanoparticles Properties

NPs were characterized for average hydrodynamic size and zeta potential by Malvern Zetasizer Nano ZS (Malvern Instruments, Malvern, UK), and for shape and size by transmission electronic microscopy (TEM, Philips/FEI BioTwin CM120 TEM, Eindhoven, Netherlands).

1.3.7. Measurement of Expression Half-Life In Vitro

Hep-3B cells were transfected with the CMV-SR39 or AFP-SR39 plasmids and harvested at days 2, 6, 10 and 14 for RT-PCR. RNA was isolated from cells using the Qiagen RNeasy Mini Kit (Qiagen catalog #74104) and on-column digestion with the Qiagen RNase-free DNase set (Qiagen catalog #79254) according to manufacturer's instructions. Reverse transcription was performed using Power SYBR™ Green Cells-to-$C_T$™ Kit (ThermoFisher catalog #4402953), and qPCR was performed using Power SYBR™ Green reagent and sequence-specific primers for HSV1-TK and SR39 using Applied Biosystems Real Time PCR Machine with cycling conditions specified by the Cells-to-$C_T$™ Kit. The following primers were used for analysis: HSV1-TK FP ACGGCGACCTGTACAACGTG (SEQ ID NO: 7) and RP AAACGCCTCCGTCCCATG (SEQ ID NO: 8), SR39 FP GCCCTTCCTGAGGACAGACAC (SEQ ID NO: 9) and RP GGGTTTATGGGCTGCTTGCC (SEQ ID NO: 10). Gene expression was analyzed per well by normalizing CT values for transfected wells to untreated wells. Fold expression was calculated by $2^{-\Delta CT}$. All PCR studies were performed with 3 biological replicates and 2 technical replicates.

1.3.8. Assessment of Native AFP Expression by Cells Lines

Huh-7, Hep 3b, SK-HEP-1, PC-3, and THLE3 cells were stained for native AFP expression using immunocytochemistry. 150,000 cells were fixed using BD Phosflow™ Fix Buffer I (BD Biosciences catalog #557870) at 37° C. for 10 minutes. After washing with BD Pharmingen™ Stain Buffer (FBS) (BD Biosences catalog #554656), cells were permeabilized using cold BD Phosflow™ Perm Buffer III (BD Biosciences catalog #558050) on ice for 30 minutes and washed twice with stain buffer. Cells were stained with PE Mouse Anti-Human Alpha-fetoprotein (BD Biosciences catalog #563002) at a 1:20 dilution in stain buffer for 20 minutes. Cells were then washed twice with PBS then resuspended in a buffer solution (2% FBS in1×PBS). Stained cells were run through a HyperCyt™ autosampler (Intelli-Cyt Corporation, Albuquerque, N. Mex.) connected to a BD Accuri™ C6 Flow Cytometer (BD Biosciences, San Jose, Calif.). The collected data was analyzed using the FlowJo™ software v.10.1r7 (Ashland, Oreg.) for percentage (AFP positive %) and intensity of AFP expression (geometric mean). Gating was performed using unstained samples and was adjusted to account for varying autofluorescence between cell types. Staining was performed in triplicate.

1.3.9. Measurement of Expression Efficacy In Vitro

For efficacy studies, SK-HEP-1, Hep-3B, Huh-7, PC-3 and THLE-3 cells were transfected with the eGFP-N1, CMV-SR39, AFP-SR39, or HSV1-TK plasmids and treated with either the prodrug ganciclovir (GCV; Invivogen catalog #sud-gcv) or the PET radiotracer 9-(4-(18)F-Fluoro-3-[hydroxymethyl]butyl)guanine, herein referred as [$^{18}$F]-FHBG, which is labeled immediately prior to the study. See Castanares et al., 2014; Ponde et al., 2004. Cells receiving no treatment were used as controls.

For dose response studies, Hep 3b cells were transfected with eGFP-N1, HSV1-TK, or CMV-SR39 and treated with GCV 24 hours after transfection. Viability was measured 48 hours after GCV treatment using the MTS viability assay from Promega (CellTiter 96 AQueous Nonradioactive Cell Proliferation Assay; Madison, Wis.) and the Synergy 2 Multi-mode Reader/Gen5™ software (Biotek, Winooski, Vt.). Viability was estimated calculating the average metabolic activity of cells from each treatment condition relative to untreated controls.

For time course studies, GCV-treated cells received the prodrug either 24 hours after transfection or 1, 3, 5, and 7 days after transfection. Viability of cells treated with GCV was assessed at days 1, 3, 5, 7 and 9 post-transfection using the same method described above. All in vitro GCV studies were performed in quadruplicate.

At day 2 and 5 post-transfection, [$^{18}$F]-FHBG uptake studies were performed. Huh-7, Hep3b, SK-HEP-1, and PC-3 cells were treated with serum-free media for 24 hours to sync cell cycles. THLE3 was not serum starved due to the sensitivity of this cell line. One hour prior to treatment, serum-free media was replaced with serum-containing media. Cells were incubated with 10 µCi/mL freshly-prepared [$^{18}$F]-FHBG for one hour at 37° C. then washed 5× with RPMI media containing 10% serum to remove extracellular [$^{18}$F]-FHBG. 50 µL 1×RIPA buffer was added to the cells and incubated on ice for 5 minutes until cells were completely lysed. Radioactivity of the cell lysate samples were measured using an automated gamma counter (LKB Wallace 1282 Compugamma CS Universal Gamma Counter). 15 serial dilutions of [$^{18}$F]-FHBG were used as standards to calculate radiotracer accumulation. Protein content for each sample was measured by Pierce™ BCA Protein Assay Kit (ThermoFisher catalog #23225) as directed by the manufacturer. Data was recorded as radioactivity (µCi) normalized to protein mass (µg). [$^{18}$F]-FHBG uptake studies were performed in triplicate.

Cells transfected with NP carrying eGFP-N1 were also evaluated with flow cytometry for a fluorescent-based quantification of transfection efficacy. Briefly, cells resuspended in a buffer solution (2% FBS in1×PBS) containing propidium iodide (PI) run through a HyperCyt™ autosampler (IntelliCyt Corporation, Albuquerque, N. Mex.) connected to a BD Accuri™ C6 Flow Cytometer (BD Biosciences, San Jose, Calif.). The collected data was analyzed using the FlowJo™ software v.10.1r7 (Ashland, Oreg.) for percentage (eGFP positive %) and intensity of eGFP expression (geometric mean). Dead cells, which stain for PI, could be gated out of the final cell population.

1.4 Results 1.4.1. Nonviral Gene Delivery to HCC

PBAE 536 self-assembles with plasmid DNA to form nanoparticles (NPs) of 157 nm diameter and 18.2 mV surface charge (see FIG. 2A). See also Zamboni et al., 2017. The particles have a uniform spherical morphology when observed using TEM (FIG. 2B).

The transfection efficacy was evaluated in five cell lines of interest: three liver cancer lines (Huh7, Hep3b, SkHep1), one prostate cancer line (PC3), and one healthy hepatocyte line (THLE3) (FIG. 2C). See also Zamboni et al., 2017. eGFP expression ranged from 51.4% to 91.0% in the cancer cell lines, while only 21.5% of the healthy hepatocytes were GFP+. The normalized geometric mean fluorescence was 21.3 to 25.6 in the HCC cell lines and 520.1 in PC-3 but dropped to 3.1 in healthy hepatocytes. These results indicate that PBAE 536 at 25 w/w demonstrates cancer-specific transfection in the cell lines of interest. Cell viability was maintained above 65% for all cell lines tested, indicating minimal cytotoxicity from the NPs. (See FIG. 2D). See also Zamboni et al., 2017.

1.4.2. Development and Characterization of CpG Free SR39 Theranostic Plasmids

A plasmid placing a gene encoding SR39 under the control of an EF1 promoter and CMV enhancer for strong, ubiquitous expression in a wide range of cell lines was designed and constructed. The SR39 gene was edited to remove all CpG sequences, and was inserted into the backbone pCpGfree-vitro, which is completely CpG free including a CpG free CMV enhancer and EF1 promoter. The final CpG free pCpGfree-vitro-CMV-EF1-SR39 plasmid is 6620 base pairs in size, which is suitable for nonviral gene delivery with PBAE NPs. This plasmid is referred to in the text as CMV-SR39 (FIG. 3A).

To add HCC-specificity to the SR39 gene, a second plasmid was developed to restrict the expression of SR39 to AFP-producing cells. Transcriptional targeting was implemented by replacing the CMV-EF1 promoter with an AFP promoter and enhancer. The AFP promoter enhancer was edited to remove all CpG sequences. The resulting CpG free pCpGfree-vitro-AFP-SR39 construct was 7922 bp in size. This plasmid is referred to in the text as AFP-SR39 (FIG. 3B).

The process of gene and promoter editing can negatively affect gene expression. To verify SR39 expression in vitro, Hep3b cells were transfected with the engineered CMV-SR39 or AFP-SR39 PBAE NPs (FIG. 4A). SR39 expression was detected in transfected cells up to 14 days, indicating that transfection with the CpG free pSR39 plasmids led to durable SR39 expression. Therefore, the changes to the SR39 gene and AFP promoter sequences did not prevent SR39 expression in HCC cells. CMV-SR39 drove stronger expression than AFP-SR39, which is due to the relative strength of the two promoters and enhancers.

To assess the therapeutic function of the transcribed SR39 protein, Hep3b HCC cells were transfected with CMV-SR39 in vitro and treated with low doses of GCV over 9 days. (FIG. 4B). Cells transfected with the eGFP control plasmid showed no significant cytotoxicity at the tested doses of GCV. Both HSV1-TK and CMV-SR39 transfected cells showed a dose-dependent response to GCV, and CMV-SR39 had a more potent effect than HSV1-TK with significantly enhanced cancer cell killing. At the lowest dose of GCV tested, 1.25 ng/µL, HSV1-TK-transfected cells maintained 82% viability while the viability of CMV-SR39 transfected cells was reduced to 51%. Thus, the CMV-SR39 plasmid demonstrated a cell killing effect in vitro, which was more potent than wild-type HSV1-TK, which allows lower doses of GCV to be used for a therapeutic effect. Manipulations to remove CpG dinucleotide from the gene and promoter did not disrupt the formation of a functional SR39 protein.

Because successful transcriptional targeting depends on AFP expression, immunostaining was performed on relevant cell lines to validate AFP (FIG. 5). Huh-7 and Hep 3b, both regarded as AFP-expressing cell lines, had 10% and 13% AFP expression detectable by flow cytometry and a normalized geometric mean fluorescence of 1.97 and 2.47 respectively. SK-HEP-1, PC-3, and THLE3 cells showed no AFP expression detectable with flow cytometry. Therefore, SK-HEP-1 serves as a non-AFP-producing HCC control; PC-3 serves as a non-AFP producing non-HCC cancer control. Finally, healthy hepatocyte THLE3 cells do not produce AFP, which restricts transcriptional targeting within the liver to HCC cells.

1.4.3. In Vitro Targeted Therapeutic Effect

All five cell lines were transfected in vitro with the ubiquitously expressed CMV-SR39 gene to validate sensitivity to the SR39 gene therapy (FIG. 6A). Transfection with CMV-SR39 induced rapid cell death in all cell lines, indicating strong ubiquitous SR39 expression. By Day 9, viability for all cell lines had dropped below 20%. When compared with the wild-type HSV1-TK treatment, CMV-SR39 induced a significantly stronger cell death response by Day 9 in Huh7, SkHep1, PC-3, and THLE3, validating the enhanced therapeutic effect of this engineered mutant construct.

To test the transcriptional targeting capabilities of the AFP-SR39 plasmid, all five cell lines were transfected in vitro with AFP-SR39 and exposed to 1.25 µg/mL GCV every other day (FIG. 6B). Again, cell viability was measured on days 3, 5, 7, and 9 with an MTS metabolic assay. Viability in AFP-expressing Huh7 and Hep3b HCC cell lines dropped to 15% and 25% respectively by Day 9. Thus, the AFP promoter and enhancer drive strong SR39 gene expression in AFP-producing HCC cells, though the effect is slightly less potent than CMV-SR39. In SK-HEP-1 cells, viability was maintained above 70%, and PC-3 prostate cancer cells remained above 90% viable over the course of the study, indicating that the transcriptional targeting is AFP-specific and will not affect non-AFP-producing cancer cells. THLE3 cells also remained over 90% viable for the duration of the study. Thus, the AFP enhancer and promoter serve to restrict SR39 expression to AFP-producing cells, which limits cell death to HCC. Further, editing this promoter and enhancer to remove all CpG dinucleotides did not damage its function or specificity.

1.4.4. In Vitro Targeted Diagnostic Effect

For this platform to serve dual therapeutic and diagnostic functions, the potency and specificity of the designed plasmids must lead to cancer-specific radiotracer accumulation, which will facilitate diagnostic PET imaging. To test the diagnostic efficacy of this therapy, transfected cells were exposed to the radiotracer [$^{18}$F]-FHBG at 10 µCi/mL for one hour. Cellular uptake of the radiotracer was quantified with a gamma counter and normalized to total protein content in the sample (FIG. 7A). CMV-SR39 transfected cells showed significant levels of radiotracer uptake in all cell lines, particularly in the highly transfected cancer lines. AFP-SR39 transfected cells showed AFP-specific uptake, with high levels of accumulation in Huh7 and Hep3b cells, low levels in SkHep1 cells, and background levels in PC-3 and THLE3 cells. The high level of uptake in CMV-SR39 and AFP-SR39-transfected AFP expressing HCC cells was maintained 5 days post-transfection, indicating persistent SR39 expression (FIG. 7B). When the radioactivity of cancer cells was normalized to that of healthy cells, there was a 40 to 50-fold higher accumulation in AFP-SR39-transfected Hep3b and Huh7 cells than in healthy hepatocytes (FIG. 7C). Although CMV-SR39 transfection led to higher levels of accumulation, the fold-expression was less favorable, indicating that transcriptional targeting could improve cancer specificity for PET imaging.

1.5 Discussion

A novel CpG free version of the SR39 gene was developed and utilized in two theranostic plasmids, CMV-SR39 and AFP-SR39, which is the first reported use of a CpG free SR39 gene. Research-grade plasmids containing CpG dinucleotides activate toll-like receptor 9 and initiate an innate immune response, which can lead to gene silencing as well as dangerous and potentially fatal toxicity. Removing CpG sequences is expected to extend the duration of gene expression in vivo, leading to improved therapeutic outcomes and extended monitoring.

Despite extensive alterations to the gene sequence, CMV-SR39 caused a potent cell death effect in HCC cell lines. This CMV-SR39 plasmid has a significantly stronger therapeutic effect over HSV1-TK therapy, even with very low concentrations of GCV. This increased sensitivity could reduce the incidence of clinical complications, such as immunosuppression, which are associated with high GCV doses. Interestingly, the cytotoxic effect of SR39 treatment resulted in >80% cell death in cell lines with only modest levels of transfection, such as THLE3 hepatocyte cells. This can be explained by the bystander effect that is seen with HSV1-TK therapy, where untransfected cells can be affected by the toxic triphosphorylated GCV compound produced by nearby transfected cells. Therefore, additional layers of cancer-targeting must be employed in addition to PBAE biomaterial-mediated targeting to avoid off-target toxicity to healthy tissues.

To add additional specificity to the cancer-specific PBAE NP delivery system, a novel CpG free version of the AFP promoter and enhancer sequence was developed. This is first reported use of a CpG free AFP promoter and the first reported use of AFP transcriptional targeting for an SR39 gene therapy. The targeted AFP-SR39 construct showed a high degree of specificity, with therapeutic effects limited to AFP-producing HCC cells, which is predicted to minimize off-target liver toxicity with GCV therapy. Additionally, AFP transcriptional targeting significantly increased the relative accumulation of [$^{18}$F]-FHBG in HCC over healthy hepatocytes, which is expected to decrease the background signal for PET imaging. Because 80% of HCC tumors express AFP, this targeted construct has the potential to affect a large number of patients.

Current treatment options for the vast majority of liver cancer patients are limited to palliative therapies with high risk of liver failure. The developed NP-based gene therapy is not only targeted and effective, it is designed for clinical use. The PBAE NP system is non-viral, avoiding risks of dangerous immunogenicity. PBAE polymers are also biodegradable, which reduces cytotoxicity and risk of inflammatory reaction. The SR39 gene demonstrates improved sensitivity to GCV, which could reduce the amount of the prodrug needed for treatment, and the AFP promoter and enhancer can direct the therapy to AFP-expressing HCCs, reducing off-target side effects. Further, by designing these plasmids to be CpG free, they are not expected to trigger a TLR9-mediated immune response and can be compatible with delivery to humans. Finally, therapeutic and molecular imaging are combined into a single platform to enable simultaneous treatment and monitoring. These plasmids when combined with the nanoparticle delivery system have the potential to transform the standard of care for HCC patients.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

El-Serag, H. B. and Rudolph, K. L., 2007. *Hepatocellular carcinoma: epidemiology and molecular carcinogenesis*. Gastroenterology, pp. 2557-2576.

Zhang, K. J., Zhang, J. Wu, Y. M, Qian, J., Liu, X. J., Yan, L. C., Zhou, X. M., Xiao, R. J., Wang, Y. G., Cao, X., Wei, N., Liu, X. R., Tang, B., Jiao, X. Y., Chen, K., and Liu, X. Y., *Complete eradication of hepatomas using an oncolytic adenovirus containing AFP promoter controlling E1A and an E1B deletion to drive IL-24 expression*. Cancer Gene Ther. 2012, 19(9):619-29.

Kim J., Lee, B., Kim, J. S., Yun C. O., Kim, J. H., Lee, Y. J., Joo, C. H., and Lee, H., *Antitumoral effects of recombinant adenovirus YKL-1001, conditionally replicating in alpha-fetoprotein-producing human liver cancer cells*. Cancer Lett., 2002, 180(1):23-32.

Wiewrodt, R., Amin K., Kiefer M., Jovanovic V. P., Kapoor V., Force S., Chang M., Lanuti M., Black M. E., Kaiser L. R., and Albelda S. M., *Adenovirus-mediated gene transfer of enhanced Herpes simplex virus thymidine kinase mutants improves prodrug-mediated tumor cell killing*. Cancer Gene Ther. 2003, 10(5):353-64.

Barton K. N., Stricker H., Elshaikh M. A., Pegg J., Cheng J., Zhang Y., Karvelis K. C., Lu M., Movsas B., and Freytag S. O., *Feasibility of adenovirus-mediated hNIS gene transfer and 131I radioiodine therapy as a definitive treatment for localized prostate cancer*. Mol Ther 2011, 19(7): 1353-9.

Tanaka, Y., et al., *Molecular tracing of the global hepatitis C virus epidemic predicts regional patterns of hepatocellular carcinoma mortality*. Gastroenterology, 2006. 130(3): p. 703-714.

El-Serag, H. B. and K. L. Rudolph, *Hepatocellular Carcinoma: Epidemiology and Molecular Carcinogenesis*. Gastroenterology, 2007. 132(7): p. 2557-2576.

Arzumanyan, A., H. M. Reis, and M. A. Feitelson, *Pathogenic mechanisms in HBV-and HCV-associated hepatocellular carcinoma*. Nature Reviews Cancer, 2013. 13(2): p. 123.

Wang, B., J Li, and X. Xiao, *Adeno-associated virus vector carrying human minidystrophin genes effectively ameliorates muscular dystrophy in mdx mouse model*. Proceedings of the National Academy of Sciences, 2000. 97(25): p. 13714-13719.

Nathwani. A C., et al., *Adenovirus-associated virus vector-mediated gene transfer in hemophilia B*. New England Journal of Medicine, 2011. 365(25): p. 2357-2365.

Marshall, E., *Gene therapy: death prompts review of adenovirus vector*. Science, 1999. 286(5448): p. 2244-2245.

Check, E., *Gene therapy: a tragic setback*. 2002, Nature Publishing Group.

Iyer, A. K., et al., *Exploiting the enhanced permeability and retention effect for tumor targeting*. Drug discovery today, 2006. 11(17-18): p. 812-818

Karlsson, J., H. J. Vaughan, and J. J. Green, *Biodegradable Polymeric Nanoparticles for Therapeutic Cancer Treatments*. Annual review of chemical and biomolecular engineering, 2018 (0).

Riley, M. K. and W. Vermerris, *Recent advances in nanomaterials for gene delivery—a review*. Nanomaterials, 2017. 7(5): p. 94.

Anderson, D G., et al., *Structure/property studies of polymeric gene delivery using a library of poly (β-amino esters)*. Molecular Therapy, 2005. 11(3): p. 426-434.

Kim, J., J. C. Sunshine, and J. J. Green, *Differential polymer structure tunes mechanism of cellular uptake and transfection routes of poly (β-amino ester) polyplexes in human breast cancer cells*. Bioconjugate chemistry, 2013. 25(1): p. 43-51.

Sunshine, J. C., et al., *Affects of base polymer hydrophobicity and end-group modification on polymeric gene delivery*. Biomacromolecules, 2011. 12(10): p. 3592-3600.

Tzeng., S. Y, et al., *Biomaterial-mediated cancer-specific DNA delivery to liver cell cultures using synthetic poly (beta-amino esters)*. Journal of biomedical materials research. Part A, 2013. 101(7): p. 1837.

Tzeng, S. Y., et al., *Non-viral gene delivery nanoparticles based on poly (β-amino esters) for treatment of glioblastoma*. Biomaterials, 2011. 32(23): p. 5402-5410.

Zamboni, C. G., et al., *Polymeric nanoparticles as cancer-specific DNA delivery vectors to human hepatocellular carcinoma*. Journal of Controlled Release. 2017. 263: p. 18-28.

Dey, D. and G. R. Evans, *Suicide gene therapy by herpes simplex virus-1 thymidine kinase (HSV-TK)*, in Targets in Gene Therapy. 2011. InTech.

Black, M. E., M. S. Kokoris. and P. Sabo. *Herpes simplex virus-1 thymidine kinase mutants created by semi-random sequence mutagenesis improve prodrug-mediated tumor cell killing*. Cancer research, 2001. 61(7): p. 3022-3026.

Lan, K.-H., et al., *In vivo selective gene expression and therapy mediated by adenoviral vectors for human carcinoembryonic antigen-producing gastric carcinoma*. Cancer research, 1997. 57(19): p. 4279-4284.

Ido, A., et al., *Gene therapy for hepatomna cells using a retrovirus vector carrying herpes simplex virus thymidine kinase gene under the control of human α-fetoprotein gene promoter*. Cancer Research, 1995. 55(14): p. 3105-3109.

Hyde. S. C., et al., *CpG-free plasmids confer reduced inflammation and sustained pulmonary gene expression*. Nature biotechnology, 2008. 26(5): p. 549.

Farré, D., et al., *Identification of patterns in biological sequences at the ALGGEN server: PROMO and MALGEN*. Nucleic acids research. 2003. 31(13): p. 3651-3653.

Messeguer, X., et al., *PROMO: detection of known transcription regulatory elements using species-tailored searches*. Bioinformatics, 2002. 18(2): p. 333-334.

Castanares. M. A., et al., *Evaluation of prostate-specific membrane antigen as an imaging reporter*. Journal of nuclear medicine: official publication, Society of Nuclear Medicine, 2014. 55(5): p. 805.

Ponde, D. E., et al., *Rapid and reproducible radiosynthesis of [18F] FHBG*. Nuclear medicine and biology, 2004. 31(1): p. 133-138.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A nucleic acid molecule comprising a nucleic acid sequence encoding a mutant thymidine kinase (TK) protein operatively linked to an alpha-fetoprotein (AFP) gene promoter, wherein the AFP gene promoter lacks CpG dinucleotides.

2. The nucleic acid molecule of claim 1, wherein the nucleic acid sequence encodes a mutant TK protein comprising the amino acid sequence of SEQ ID NO: 1.

3. The nucleic acid molecule of claim 1, wherein the AFP gene promoter lacks CpG dinucleotides.

4. The nucleic acid molecule of claim 3, wherein the AFP gene promoter comprises the nucleic acid sequence of SEQ ID NO: 3.

5. The nucleic acid molecule of claim 1, wherein the non-native promoter comprises a mouse CMV promoter and human EF1 enhancer.

6. The nucleic acid molecule of claim 1, wherein the nucleic acid molecule is plasmid DNA.

7. A composition comprising the nucleic acid molecule of claim 1 and a poly(beta-amino ester) (PBAE) of formula (I):

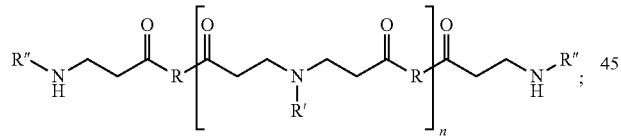
(I)

and wherein:
n is an integer from 1 to 10,000;
each R is independently selected from the group consisting of:

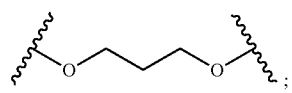
(B3)

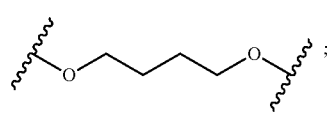
(B4)

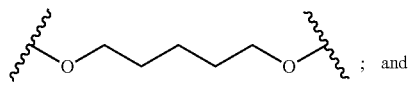
(B5)
; and

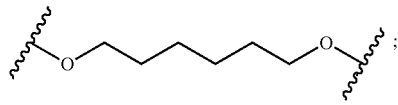
(B6)
;

each R' is independently selected from the group consisting of:

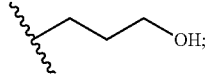
(S3)

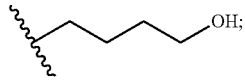
(S4)

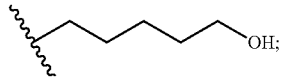
(S5)

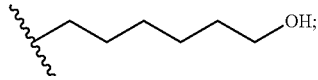
(S6)

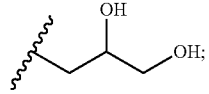
(S7)

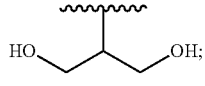
(S8)

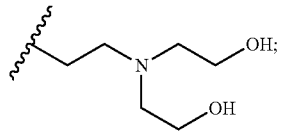
(S9)

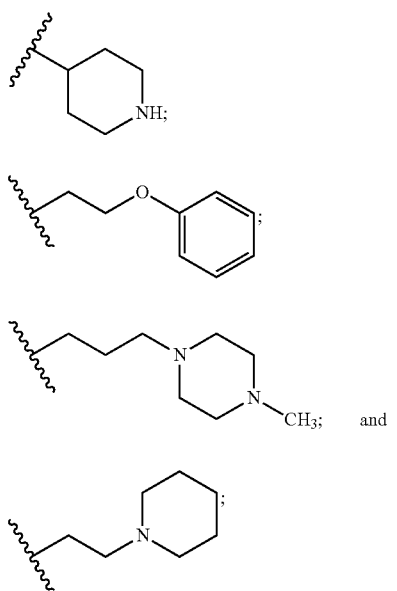
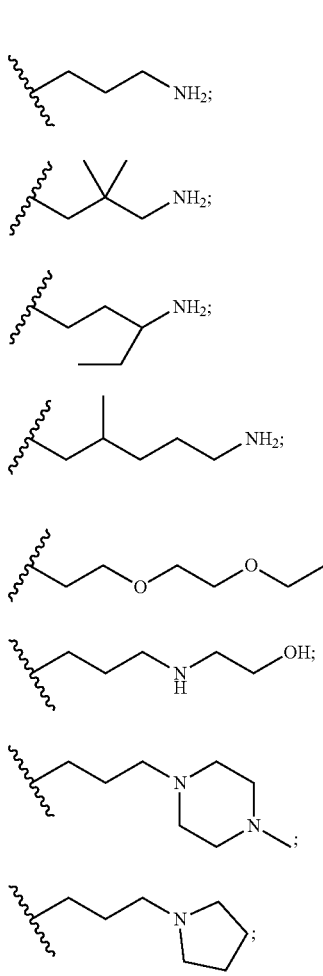
each R'' is independently selected from the group consisting of:
(E1) (E2) (E3) (E4) (E5) (E6) (E7) (E8)
(E9) (E10) (E11) (E12) (E13) (E14)
8. The composition of claim 7, wherein:
each R is independently selected from the group consisting of;
(B4) (B5)
each R' is independently selected from the group consisting of:
(S3) (S4)

-continued
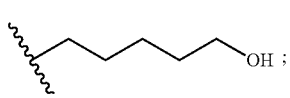
(S5)
and
each R″ is independently selected from the group consisting of:
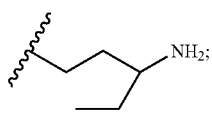
(E3)
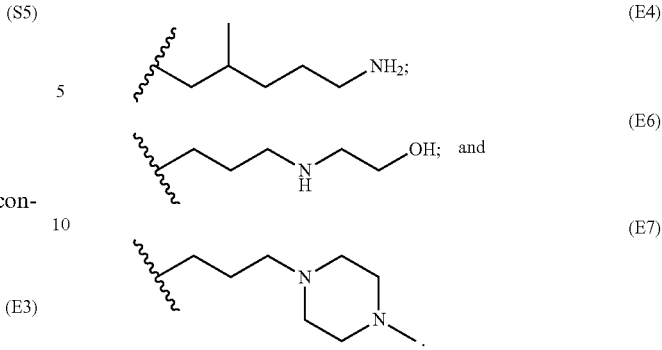
9. The composition of claim 8, wherein a combination of R, R′, and R″ is selected from the group consisting of:
| Compound Code | R | R′ | R″ |
|---|---|---|---|
| 446 | (B4) | (S4) | (E6) |
| 447 | (B4) | (S4) | (E7) |
| 453 | (B4) | (S5) | (E3) |
| 454 | (B4) | (S5) | (E4) |
| 456 | (B4) | (S5) | (E6) |
| 457 | (B4) | (S5) | (E7) |
| 534 | (B5) | (S3) | (E4) |

-continued
| Compound Code | R | R' | R" |
|---|---|---|---|
| 536 | (B5) | (S3) | (E6) |
| 537 | (B5) | (S3) | (E7) |
| 543 | (B5) | (S4) | (E3) |
| 544 | (B5) | (S4) | (E4) |
| 546 | (B5) | (S4) | (E6) |
| 547 | (B5) | (S4) | (E7) |
10. The composition of claim 9, wherein the PBAE of formula (I) is selected from the group consisting of:
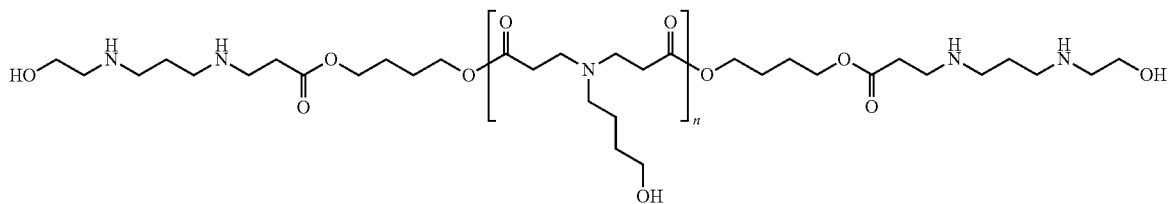
446
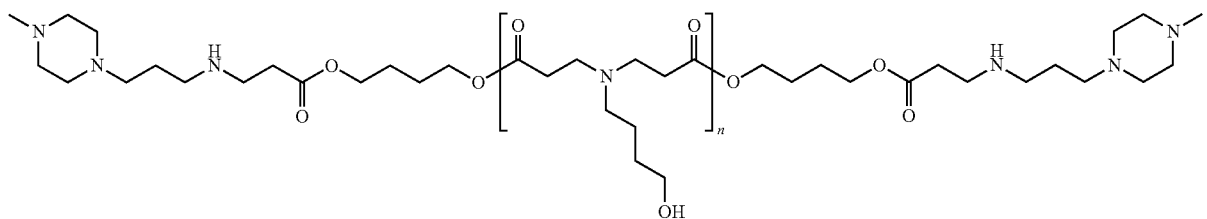
447

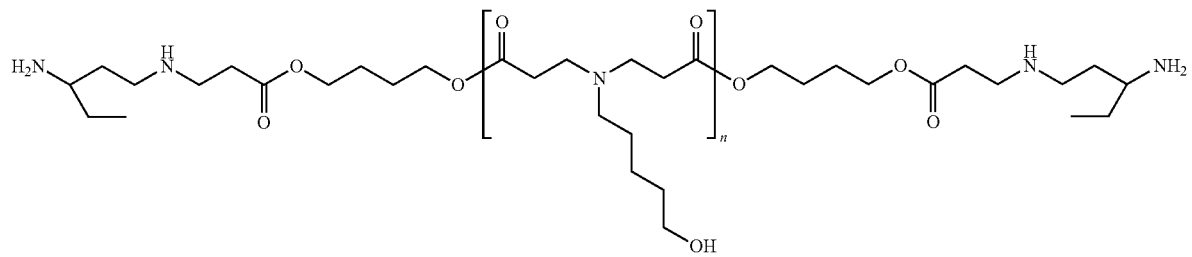
453
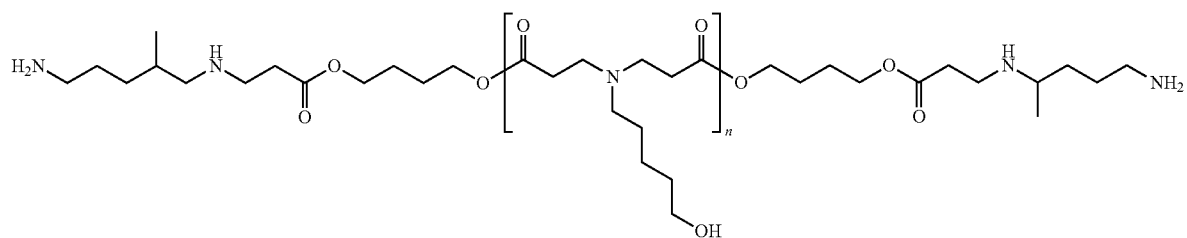
454
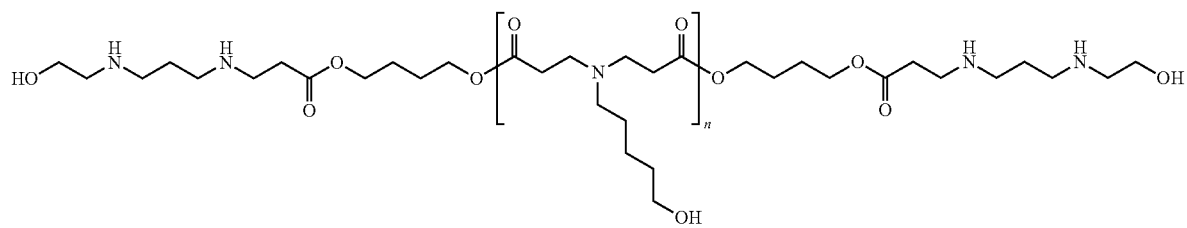
456
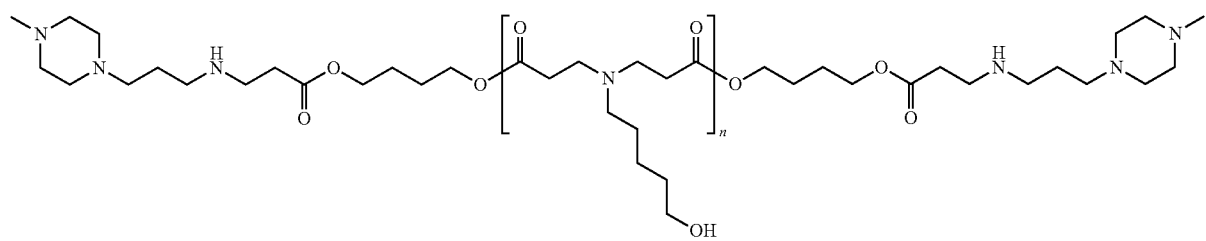
457
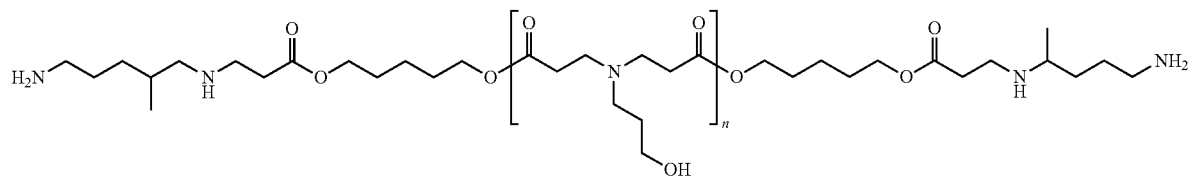
534
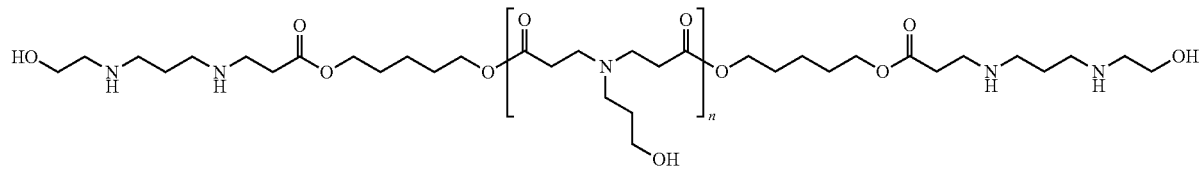
536

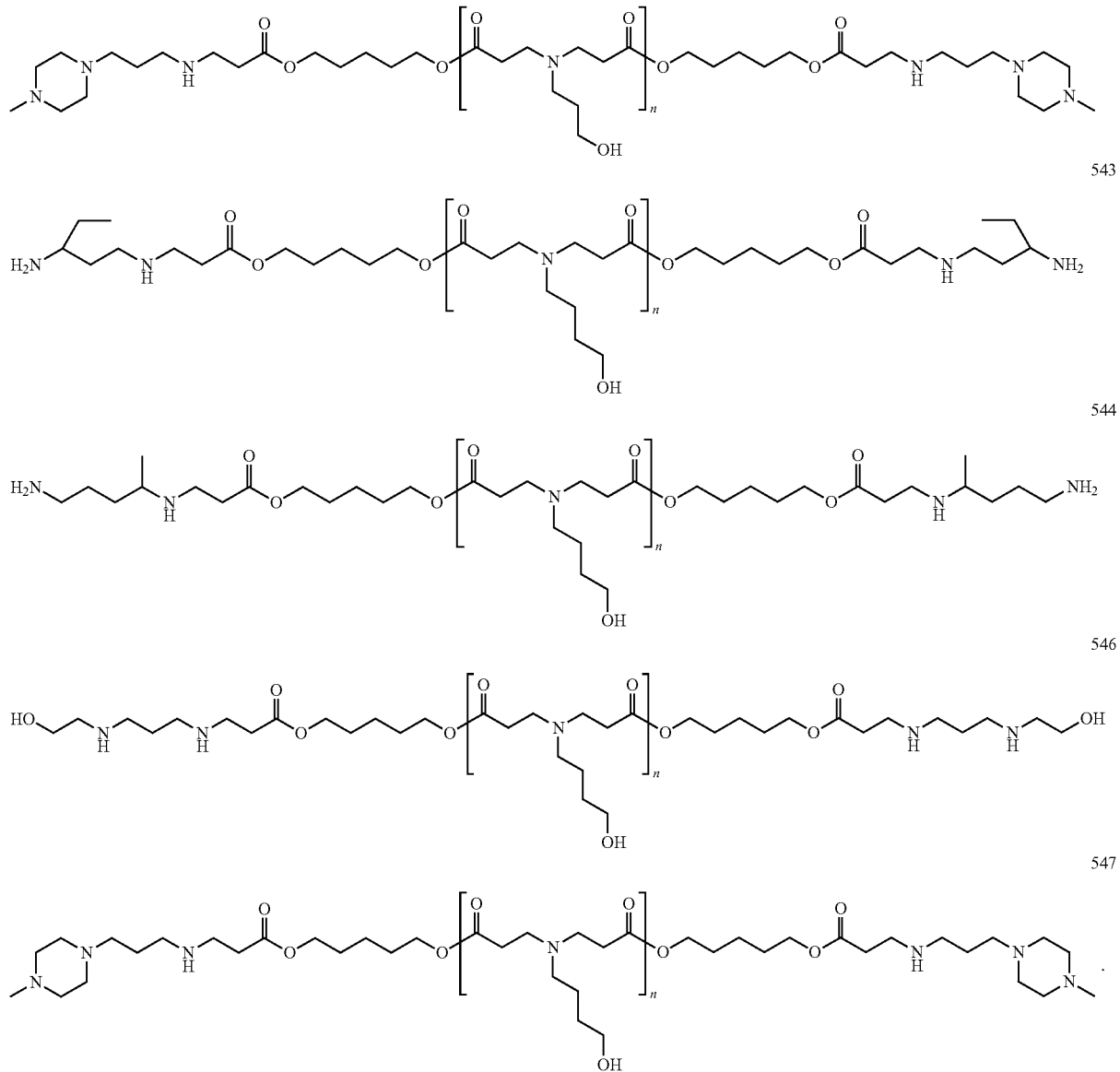

11. A pharmaceutical formulation comprising the composition of claim 7 in a pharmaceutically acceptable carrier.

12. The pharmaceutical formulation of claim 11, further comprising one or more therapeutic agents.

13. The pharmaceutical formulation of claim 12, wherein the one or more therapeutic agents is ganciclovir (GCV), valganciclovir, or another small molecule that is acted upon by the mutant TK protein to have a therapeutic effect.

14. The pharmaceutical formulation of claim 11, further comprising one or more imaging agents.

15. The pharmaceutical formulation of claim 14, wherein the one or more imaging agents is 9-(4-(18)F-fluoro-3-[hydroxymethyl]butyl) guanine ((18)F-FHBG) or another small molecule that is acted upon by the SR39 kinase to have a diagnostic effect.

16. The pharmaceutical formulation of claim 11, further comprising a nanoparticle or microparticle of the PBAE of formula (I).

17. The pharmaceutical formulation of claim 16, wherein the nanoparticle or microparticle of the PBAE of formula (I) is encapsulated in a poly(lactic-co-glycolic acid) (PLGA) nanoparticle or microparticle.

18. A method for treating or diagnosing a cancer, the method comprising administering an effective amount of a composition of claim 7 to a subject in need of treatment or diagnosing thereof.

19. The method of claim 18, wherein the cancer is hepatocellular carcinoma (HCC) or prostate cancer.

20. The method of claim 18, further comprising administering to the subject one or more therapeutic agents.

21. The method of claim 20, wherein the one or more therapeutic agents is ganciclovir (GCV) or valganciclovir.

22. The method of claim 18, further comprising administering to the subject one or more imaging agents.

23. The method of claim 22, wherein the one or more imaging agents is 9-(4-(18)F-fluoro-3-[hydroxymethyl]butyl) guanine ((18)F-FHBG).

24. The method of claim 22, further comprising acquiring an image.

25. The method of claim 24, wherein the image is a positron emission tomography (PET) image.

26. A kit comprising the nucleic acid molecule of claim 1 alone or in a PBAE composition of formula (I).

27. The kit of claim 26, further comprising a transfection reagent.

28. The kit of claim 27, wherein the transfection reagent is selected from the group consisting of a polymer, a lipid, a nanoparticle, or an electroporation/nucleofection solution.

29. The kit of claim 26, further comprising one or more therapeutic agents.

30. The kit of claim 29, wherein the one or more therapeutic agents is ganciclovir (GCV) or valganciclovir.

31. The kit of claim 26, further comprising one or more imaging agents.

32. The kit of claim 31, wherein the one or more imaging agents is 9-(4-(18)F-fluoro-3-[hydroxymethyl]butyl) guanine ((18)F-FHBG).

33. The kit of claim 26, further comprising one of more of multiple dosage units of the composition, a pharmaceutically acceptable carrier, a device for administration of the composition, instructions for use, and combinations thereof.

34. An isolated nucleic acid sequence comprising an alpha-fetoprotein (AFP) gene promoter which lacks CpG dinucleotides.

35. The isolated nucleic acid sequence of claim 34, which comprises SEQ ID NO: 3.

* * * * *

SEQUENCE LISTING

<160> NUMBER OF SEQ ID NOS: 10

<210> SEQ ID NO 1
<211> LENGTH: 376
<212> TYPE: PRT
<213> ORGANISM: Artificial sequence
<220> FEATURE:
<223> OTHER INFORMATION: Synthetic

<400> SEQUENCE: 1

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Ile Phe
145                 150                 155                 160

Leu Asp Arg His Pro Ile Ala Phe Met Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe

Ala Arg Glu Met Gly Glu Ala Asn
    370             375

<210> SEQ ID NO 2
<211> LENGTH: 1131
<212> TYPE: DNA
<213> ORGANISM: Artificial sequence
<220> FEATURE:
<223> OTHER INFORMATION: Synthetic

<400> SEQUENCE: 2

| | | | | |
|---|---|---|---|---|
| atggcttcct | accctggcca | tcagcatgcc | tctgcctttg | accaggctgc cagatctaga | 60 |
| ggccatagca | acagaagaac | tgccttgaga | cctagaagac | agcaagaagc cactgaagtc | 120 |
| agacctgagc | agaaaatgcc | caccctactg | agggtttata | tagatggtcc ccatgggatg | 180 |
| gggaaaacca | ccaccaccca | actgctggtg | ccctgggta | gcagagatga tattgtctat | 240 |
| gtacctgagc | ccatgactta | ctggaggtg | ctggggggctt | ctgagacaat tgccaacatc | 300 |
| tacaccacac | aacacagact | ggaccagggt | gagatatctg | ctggggatgc tgctgtggta | 360 |
| atgacatctg | cccagataac | aatgggcatg | cctatgctg | tgacagatgc tgttctggct | 420 |
| cctcatattg | gggggaggc | tgggagctca | catgcccctc | ccctgccct caccattttc | 480 |
| ctggacagac | atcccattgc | cttcatgctg | tgctaccctg | ctgccagata ccttatgggc | 540 |
| agcatgaccc | ccaggctgt | gctggccttt | gtggccctca | tcccccctac cttgcctggc | 600 |
| acaaacattg | tgttggggc | ccttcctgag | gacagacaca | ttgacagact ggccaaaaga | 660 |
| cagagacctg | gagagagact | tgacctggct | atgctggctg | ccattagaag ggtttatggg | 720 |
| ctgcttgcca | atactgtgag | atatctgcag | gaggagggt | cctggagaga ggattgggga | 780 |
| cagctttctg | ggactgctgt | gcctccccag | ggtgctgagc | cccagagcaa tgctggccca | 840 |
| agacccata | ttggggacac | cttatttacc | ctgtttagag | ccctgagtt gctggccccc | 900 |
| aatggagacc | tgtacaatgt | gtttgcctgg | gccttggatg | tcttggccaa agactcaga | 960 |
| cccatgcatg | tctttatcct | ggattatgac | caatcccctg | ctggctgcag agatgccctg | 1020 |
| ctgcaactta | cctctgggat | ggtccagacc | catgtcacca | ccctggctc catacccacc | 1080 |
| atctgtgacc | tggccagaac | cttgccaga | gagatggggg | aggctaactg a | 1131 |

<210> SEQ ID NO 3
<211> LENGTH: 2144
<212> TYPE: DNA
<213> ORGANISM: Artificial sequence
<220> FEATURE:
<223> OTHER INFORMATION: Synthetic

<400> SEQUENCE: 3

| | | | | |
|---|---|---|---|---|
| gcttagaaat | atgggggtag | ggtggtggt | ggtaattctg | ttttctcccc ataggtgaga | 60 |
| taagcattgg | gttaaatgtg | ctttctctct | ctccctctcc | tttcttaaga attaagggac | 120 |
| agactatggg | ctggaggact | tgaggatgt | ctgtctcata | acacttgggt tgtatctgtt | 180 |
| ctatggggct | tgttttaagc | ttggcaactt | gcaacagggt | tcactgactt tctccccagg | 240 |
| cccaaggtac | tgtcctcttt | tcatatctgt | tttggggcct | ctggggcttg aatatctgag | 300 |
| aaaatataaa | catttcaata | atgttctgtg | gtgagatgag | tatgagagat gtgtcattca | 360 |
| tttgtatcaa | tgaatgaatg | aggacaatta | gtgtataaat | ccttagtaca acaatctgag | 420 |
| ggtaggggtg | gtactattca | atttctattt | ataaagatac | ttatttctat ttatttatgc | 480 |

```
ttgtgacaaa tgttttgttt gggaccacag gaatcacaaa gatgagtctt tgaatttaag      540
aagttaatgg tccaggaata attacatagc ttacaaatga ctatgatata ccatcaaaca      600
agaggttcca tgagaaaata atctgaaagg tttaataagt tgtcaaaggt gagagggctc      660
ttctctagct agagactaat cagaaataca ttcagggata attatttgaa tagaccttaa      720
gggttgggta cattttgttc aagcattgat ggagaaggag agtgaatatt tgaaaacatt      780
ttcaactaac caaccaccca atccaacaaa caaaaaatga aaagaatctc agaaacagtg      840
agataagaga aggaattttc tcacaaccca catgtatagc tcaactgctc tgaagaagta      900
tatatctaat atttaacact aacatcatgc taataatgat aataattact gtcattttt       960 aatgtctata agtaccaggc atttagaaga tattattcca tttatatatc aaaataaact     1020 tgagggata gatcattttc atgatatatg agaaaaatta aaaatcagat tgaattattt     1080
gcctgtcata cagctaataa ttgaccataa gacaattaga tttaaattag ttttgaatct     1140
ttctaatacc aaagttcagt ttactgttcc atgttgcttc tgagtggctt cacagactta     1200
tgaaaaagta aatggaatca gaattacatc aatgcaaaag cattgctgtg aactctgtac     1260
ttaggactaa actttgagca ataacacata tagattgagg attgtttgct gttagtatac     1320
aaactctggt tcaaagctcc tctttattgc ttgtcttgga aaatttgctg ttcttcatgg     1380
tttctctttt cactgctatc tattttctc aaccactcac atggctacaa taactgtctg     1440
caagcttatg attcccaaat gtctatctct agcctcaatc ttgttccaga agataaaaag     1500
tagtattcaa atgcacatca acatctccac ttggagggct taaagatgtt tcaacataca     1560
aactggggag ttttgcctgg aatgtttcct aaaatgtgtc ctgtagcaca tagggtcctc     1620
ttgttcctta aaatctaatt acttttagcc cagtgctcat cccacctatg gggagatgag     1680
agtgaaaagg gagcctgatt aataattaca ctaagtcaat aggcatagag ccaggactgt     1740
ttgggtaaac tggtcacttt atcttaaact aaatatatcc aaaactgaac atgtacttag     1800
ttactaagtc tttgacttta tctcattcat accactcagc tttatccagg ccactagagt     1860
ttgaggagaa tatttgttat atttgcaaaa taaaataagt ttgcaagttt ttttttttctg     1920 ccccaaagag ctctgtgtcc ttgaactaaa aatacaaata actgctatgc tgttaattat     1980
tgacaaatgt cccatttca acctaaggaa ataccataaa gtaacagata taccaacaaa     2040
aggttactag ttaacaggca ttgcctgaaa agagtataaa agaatttcag catgattttc     2100
catattgtgc ttccaccact gccaataaca aaataactag caac                      2144

<210> SEQ ID NO 4
<211> LENGTH: 5488
<212> TYPE: DNA
<213> ORGANISM: Artificial sequence
<220> FEATURE:
<223> OTHER INFORMATION: Synthetic

<400> SEQUENCE: 4
ttaattaaaa ttatctctaa ggcatgtgaa ctggctgtct tggttttcat ctgtacttca       60
tctgctacct ctgtgacctg aaacatattt ataattccat taagctgtgc atatgataga      120
tttatcatat gtattttcct taaggattt ttgtaagaac taattgaatt gatacctgta      180
aagtctttat cacactaccc aataaataat aaatctcttt gttcagctct ctgtttctat      240
aaatatgtac cagttttatt gtttttagtg gtagtgattt tattctcttt ctatatatat      300
acacacacat gtgtgcattc ataaatatat acaattttta tgaataaaaa attattagca      360
atcaatattg aaaaccactg attttttgttt atgtgagcaa acagcagatt aaaaggaatt      420
```

| | |
|---|---|
| tcaattgcct gcaggagtca atgggaaaaa cccattggag ccaagtacac tgactcaata | 480 |
| gggactttcc attgggtttt gcccagtaca taaggtcaat aggggtgag tcaacaggaa | 540 |
| agtcccattg gagccaagta cattgagtca atagggactt tccaatgggt tttgcccagt | 600 |
| acataaggtc aatgggaggt aagccaatgg gttttccca ttactgacat gtatactgag | 660 |
| tcattaggga ctttccaatg ggttttgccc agtacataag gtcaataggg gtgaatcaac | 720 |
| aggaaagtcc cattggagcc aagtacactg agtcaatagg gactttccat ggggttttgc | 780 |
| ccagtacaaa aggtcaatag ggggtgagtc aatgggtttt tcccattatt ggcacataca | 840 |
| taaggtcaat aggggtgact agtggagaag agcatgcttg agggctgagt gcccctcagt | 900 |
| gggcagagag cacatggccc acagtccctg agaagttggg gggaggggtg ggcaattgaa | 960 |
| ctggtgccta gagaaggtgg ggcttgggta aactgggaaa gtgatgtggt gtactggctc | 1020 |
| caccttttc cccagggtgg gggagaacca tatataagtg cagtagtctc tgtgaacatt | 1080 |
| caagcttctg ccttctccct cctgtgagtt tggtaagtca ctgactgtct atgcctggga | 1140 |
| aagggtgggc aggagatggg gcagtgcagg aaaagtggca ctatgaaccc tgcagcccta | 1200 |
| gacaattgta ctaaccttct tctctttcct ctcctgacag gttggtgtac agtagcttcc | 1260 |
| aagtactaag atctagtgca cagggcccac catggagcta gctggccaga catgataaga | 1320 |
| tacattgatg agtttggaca aaccacaact agaatgcagt gaaaaaaatg ctttatttgt | 1380 |
| gaaatttgtg atgctattgc tttatttgta accattataa gctgcaataa acaagttaac | 1440 |
| aacaacaatt gcattcattt tatgtttcag gttcaggggg aggtgtggga ggttttttaa | 1500 |
| agcaagtaaa acctctacaa atgtggtatg gaattggagc cccactgtgt tcatcttaca | 1560 |
| gatggaaata ctgacattca gaggagttag ttaacttgcc taggtgattc agctaataag | 1620 |
| tgcaagaaag atttcaatcc aaggtgattt gattctgaag cctgtgctaa tcacattaca | 1680 |
| ccaagctaca acttcattta taataataa gtcagctttc aagggccttt caggtgtcct | 1740 |
| gcacttctac aagctgtgcc atttagtgaa cacaaaatga gccttctgat gaagtagtct | 1800 |
| tttcattatt tcagatatta gaacactaaa attcttagct gccagctgat tgaaggctgg | 1860 |
| gacaaaattc aaacatgcat ctacaacaat atatatctca atgttagtct ccaaattcta | 1920 |
| ttgacttcaa ctcaagagaa tataaagagc tagtctttat acactcttta aggtatgata | 1980 |
| tcatctggaa agtaacaaaa ttgatgcaaa tttgaatgaa ctttatcatg gtgtatttac | 2040 |
| acaatgtgtt tcttctccct gcaatgtatt tctttctcta attccttcca tttgatcttt | 2100 |
| catacacaat ctggttctga tgtatgtttt ttggatgcac ttttcaactc caaaagacag | 2160 |
| agctagttac tttcttcctg gtgctccaag cactgtattt gtatctgtat tcaagccctt | 2220 |
| tgcaatattg tactggatca ttatttcacc tctaggatgg cttccccagg caacttgtgt | 2280 |
| tcacccagag actacatttt gtatcttgtt gacctttgaa cttccaccag tgtctaaaaa | 2340 |
| taatatgtat gcaaaattac ttgctatgag aatgtataat taaacaatat aaaaaggaga | 2400 |
| agcaaggaga gaaacacagg tgtgtatttg tgtttgtgtg cttaaaaggc agtgtggaaa | 2460 |
| aggaagaaat gccatttata gtgaggagac aaagttatat tacctcttat ctggcttta | 2520 |
| aggagatttt gctgagctaa aaatcctata ttcatgaaaa agccttacct gagttgccaa | 2580 |
| tacctcaatt ctaaaataca gcatagcaaa actttaacct ccaaatcaag cctctacttg | 2640 |
| aatccttttc tgagggatga ataaggcata ggcatcaggg gctgttgcca atgtgcatta | 2700 |
| gctgtttgca gcctcacctt ctttcatgga gtttaagata tagtgtattt tcccaaggtt | 2760 |

```
tgaactagct cttcatttct ttatgtttta aatgcactga cctcccacat tccctttta    2820
gtaaaatatt cagaaataat ttaaatacat cattgcaatg aaaataaatg ttttttatta    2880
ggcagaatcc agatgctcaa ggcccttcat aatatccccc agtttagtag ttggacttag    2940
ggaacaaagg aacctttaat agaaattgga cagcaagaaa gctctagctt tagaagaact    3000
catcaagaag tctgtagaag gcaattctct gggagtcagg ggctgcaatg ccatagagca    3060
ctaggaacct gtctgcccac tctccccta gctcttctgc tatgtccctg gttgctaggg    3120
caatgtcctg gtacctgtca gccactccca gcctgccaca gtctatgaag ccagagaacc    3180
ttccattttc aaccatgatg ttgggaaggc aggcatcccc atgagtcacc actaggtcct    3240
caccatctgg catggatgcc ttgagcctgg caaatagttc agcaggggcc aggccctggt    3300
gttcttcatc caagtcatct tggtccacca ggccagcctc catcctggtt ctggccctct    3360
ctatcctgtg cttggcctgg tggtcaaagg ggcaggtggc tgggtcaagg gtgtggagtc    3420
ttctcatggc atcagccatg attgacactt tctcagctgg agctaggtga gaggaaagga    3480
ggtcctgccc aggcacctca cctagtagga gccagtccct tccagcttct gtgaccacat    3540
caaggacagc tgcacagggg accccagttg ttgccaacca ggagagtctg gcagcctcat    3600
cctggagctc attgagagcc ccactgaggt ctgtctttac aaaaggact ggcctgcctt    3660
gggctgaaag tctgaaaact gctgcatcag agcaaccaat ggtctgctgt gcccagtcat    3720
agccaaacag tctctcaacc caggcagctg agaacctgc atgtaggcca tcttgttcaa    3780
tcatgatggc tcctcctgtc aggagaggaa agagaagaag gttagtacaa ttgctatagt    3840
gagttgtatt atactatgct tatgattaat tgtcaaacta gggctgcagg gttcatagtg    3900
ccacttttcc tgcactgccc catctcctgc ccacccttc ccaggcatag acagtcagtg    3960
acttaccaaa ctcacaggag ggagaaggca gaagcttttt gcaaaagcct aggcctccaa    4020
aaaagcctcc tcactacttc tggaatagct cagaggccca gggggcctgg gcctctgcat    4080
aaataaaaaa aattagtcag cctggggctg gggtggggc aggggtgggg ggccaactgg    4140
gcagggtgg ggggccacta gtgggactat ggttgctgac taattgagat gcatgctttg    4200
catacttctg cctgctgggg agcctgggga ctttccacac ctggttgctg actaattgag    4260
atgcatgctt tgcatacttc tgcctgctgg ggagcctggg gactttccac accctaactg    4320
acacacattc cacagctggt tctttcagcc tcagaaggta cctaaccaag ttcctctttc    4380
agaggttatt tcaggccctg caggaattca gtcaatatgt tcaccccaaa aaagctgttt    4440
gttaacttgt caacctcatt ctaaaatgta tatagaagcc caaagacaa taacaaaaat    4500
attcttgtag aacaaaatgg gaaagaatgt tccactaaat atcaagattt agagcaaagc    4560
atgagatgtg tggggataga cagtgaggct gataaaatag agtagagctc agaaacagac    4620
ccattgatat atgtaagtga cctatgaaaa aaatatggca ttttacaatg ggaaaatgat    4680
ggtcttttc tttttagaa aaacaggaa atatatttat atgtaaaaaa taaagggaa    4740
cccatatgtc ataccataca cacaaaaaaa ttccagtgaa ttataagtct aaatggagaa    4800
ggcaaaactt taaatctttt agaaaataat atagaagcat gccatcaaga cttcagtgta    4860
gagaaaaatt tcttatgact caaagtccta accacaaaga aaagattgtt aattagattg    4920
catgaatatt aagacttatt tttaaaatta aaaaccatt aagaaaagtc aggccataga    4980
atgacagaaa atatttgcaa caccccagta aagagaattg taatatgcag attataaaaa    5040
gaagtcttac aaatcagtaa aaaataaaac tagcaaaaa tttgaacaga tgaaagaaa    5100
actctaaata atcattacac atgagaaact caatctcaga aatcagagaa ctatcattgc    5160
```

| | | | |
|---|---|---|---|
| atatacacta | aattagagaa | atattaaaag gctaagtaac | atctgtggct taattaagtt | 5220 |
| atcctaggaa | accttaaaac | ctttaaaagc cttatatatt | ctttttttc ttataaaact | 5280 |
| taaaacctta | gaggctattt | aagttgctga tttatattaa | ttttattgtt caaacatgag | 5340 |
| agcttagtac | atgaaacatg | agagcttagt acattagcca | tgagagctta gtacattagc | 5400 |
| catgagggtt | tagttcatta | aacatgagag cttagtacat | taaacatgag agcttagtac | 5460 |
| atactatcaa | caggttgaac | tgctgatt | | 5488 |

<210> SEQ ID NO 5
<211> LENGTH: 6620
<212> TYPE: DNA
<213> ORGANISM: Artificial sequence
<220> FEATURE:
<223> OTHER INFORMATION: Synthetic

<400> SEQUENCE: 5

| | | | |
|---|---|---|---|
| ttaattaaaa | ttatctctaa | ggcatgtgaa ctggctgtct | tggttttcat ctgtacttca | 60 |
| tctgctacct | ctgtgacctg | aaacatattt ataattccat | taagctgtgc atatgataga | 120 |
| tttatcatat | gtattttcct | taaggatttt tgtaagaac | taattgaatt gatacctgta | 180 |
| aagtctttat | cacactaccc | aataaataat aaatctcttt | gttcagctct ctgtttctat | 240 |
| aaatatgtac | cagttttatt | gtttttagtg gtagtgattt | tattctcttt ctatatatat | 300 |
| acacacacat | gtgtgcattc | ataaatatat acaattttta | tgaataaaaa attattagca | 360 |
| atcaatattg | aaaaccactg | attttgtttt atgtgagcaa | acagcagatt aaaaggaatt | 420 |
| tcaattgcct | gcaggagtca | atgggaaaaa cccattggag | ccaagtacac tgactcaata | 480 |
| gggactttcc | attgggtttt | gcccagtaca taaggtcaat | aggggtgag tcaacaggaa | 540 |
| agtcccattg | gagccaagta | cattgagtca atagggactt | tccaatgggt tttgcccagt | 600 |
| acataaggtc | aatgggaggt | aagccaatgg gttttttccca | ttactgacat gtatactgag | 660 |
| tcattaggga | ctttccaatg | gttttgccc agtacataag | gtcaataggg gtgaatcaac | 720 |
| aggaaagtcc | cattggagcc | aagtacactg agtcaatagg | gactttccat tgggttttgc | 780 |
| ccagtacaaa | aggtcaatag | ggggtgagtc aatgggtttt | tcccattatt ggcacataca | 840 |
| taaggtcaat | aggggtgact | agtggagaag agcatgcttg | agggctgagt gcccctcagt | 900 |
| gggcagagag | cacatggccc | acagtccctg agaagttggg | gggagggtg ggcaattgaa | 960 |
| ctggtgccta | gagaaggtgg | ggcttgggta aactgggaaa | gtgatgtggt gtactggctc | 1020 |
| cacctttttc | cccagggtgg | gggagaacca tatataagtg | cagtagtctc tgtgaacatt | 1080 |
| caagcttctg | ccttctccct | cctgtgagtt tggtaagtca | ctgactgtct atgcctggga | 1140 |
| aagggtgggc | aggagatggg | gcagtgcagg aaaagtggca | ctatgaaccc tgcagcccta | 1200 |
| gacaattgta | ctaaccttct | tctctttcct ctcctgacag | gttggtgtac agtagcttcc | 1260 |
| aagtactaag | atctagtgca | cagcttagac cagtactatg | gcttcctacc ctggccatca | 1320 |
| gcatgcctct | gcctttgacc | aggctgccag atctagaggc | catagcaaca gaagaactgc | 1380 |
| cttgagacct | agaagacagc | aagaagccac tgaagtcaga | cctgagcaga aaatgcccac | 1440 |
| cctactgagg | gtttatatag | atggtcccca tgggatgggg | aaaaccacca ccacccaact | 1500 |
| gctggtggcc | ctgggtagca | gagatgatat tgtctatgta | cctgagccca tgacttactg | 1560 |
| gagggtgctg | ggggcttctg | agacaattgc caacatctac | accacacaac acagactgga | 1620 |
| ccagggtgag | atatctgctg | gggatgctgc tgtggtaatg | acatctgccc agataacaat | 1680 |

```
gggcatgcct tatgctgtga cagatgctgt tctggctcct catattgggg gggaggctgg    1740
gagctcacat gcccctcccc ctgccctcac cattttcctg gacagacatc ccattgcctt    1800
catgctgtgc taccctgctg ccagatacct tatgggcagc atgacccccc aggctgtgct    1860
ggcctttgtg gccctcatcc ccctacctt gcctggcaca acattgtgt tgggggccct      1920 tcctgaggac agacacattg acagactggc aaaagacag agacctggag agagacttga    1980
cctggctatg ctggctgcca ttagaagggt ttatgggctg cttgccaata ctgtgagata    2040
tctgcaggga ggagggtcct ggagagagga ttggggacag cttctggga ctgctgtgcc     2100 tccccagggt gctgagcccc agagcaatgc tggcccaaga ccccatattg ggacacctt     2160 atttaccctg tttagagccc ctgagttgct ggccccaat ggagacctgt acaatgtgtt     2220
tgcctgggcc ttggatgtct tggccaaaag actcagaccc atgcatgtct ttatcctgga    2280
ttatgaccaa tccctgctg gctgcagaga tgccctgctg caacttacct ctgggatggt    2340
ccagacccat gtcaccaccc ctggctccat acccaccatc tgtgacctgg ccagaaacctt  2400 tgccagagag atgggggagg ctaactgagc tagctggcca gacatgataa gatacattga    2460
tgagtttgga caaccacaa ctagaatgca gtgaaaaaaa tgctttattt gtgaaatttg     2520
tgatgctatt gctttatttg taaccattat aagctgcaat aaacaagtta acaacaacaa    2580
ttgcattcat tttatgtttc aggttcaggg ggaggtgtgg gaggtttttt aaagcaagta    2640
aaacctctac aaatgtggta tggaattgga gcccccactgt gttcatctta cagatggaaa   2700
tactgacatt cagaggagtt agttaacttg cctaggtgat tcagctaata agtgcaagaa    2760
agatttcaat ccaaggtgat ttgattctga agcctgtgct aatcacatta caccaagcta    2820
caacttcatt tataaataat aagtcagctt tcaagggcct ttcaggtgtc ctgcacttct    2880
acaagctgtg ccatttagtg aacacaaaat gagccttctg atgaagtagt cttttcatta    2940
tttcagatat tagaacacta aaattcttag ctgccagctg attgaaggct gggacaaaat    3000
tcaaacatgc atctacaaca atatatatct caatgttagt ctccaaattc tattgacttc    3060
aactcaagag aatataaaga gctagtcttt atacactctt taaggtatga tatcatctgg    3120
aaagtaacaa aattgatgca aatttgaatg aactttatca tggtgtattt acacaatgtg    3180
tttcttctcc ctgcaatgta tttctttctc taattccttc catttgatct ttcatacaca    3240
atctggttct gatgtatgtt ttttggatgc acttttcaac tccaaaagac agagctagtt    3300
actttcttcc tggtgctcca agcactgtat ttgtatctgt attcaagccc tttgcaatat    3360
tgtactggat cattatttca cctctaggat ggcttcccca ggcaacttgt gttcacccag    3420
agactacatt ttgtatcttg ttgaccttg aacttccacc agtgtctaaa aataatatgt      3480
atgcaaaatt acttgctatg agaatgtata attaaacaat ataaaagga gaagcaagga    3540 gagaaacaca ggtgtgtatt tgtgtttgtg tgcttaaaag gcagtgtgga aaaggaagaa    3600
atgccattta tagtgaggag acaaagttat attacctctt atctggcttt taaggagatt    3660
ttgctgagct aaaaatccta tattcataga aaagccttac ctgagttgcc aatacctcaa    3720
ttctaaaata cagcatagca aaactttaac ctccaaatca agcctctact tgaatccttt    3780
tctgagggat gaataaggca taggcatcag gggctgttgc caatgtgcat tagctgtttg    3840
cagcctcacc ttctttcatg gagtttaaga tatagtgtat tttcccaagg tttgaactag    3900
ctcttcattt cttatgtttt taaatgcact gacctcccac attccctttt tagtaaaata    3960
ttcagaaata atttaaatac atcattgcaa tgaaaataaa tgttttttat taggcagaat    4020
ccagatgctc aaggcccttc ataatatccc ccagtttagt agttggactt agggaacaaa    4080
```

```
ggaacccttta ataganaattg dacagcaaga aagctctagc tttagaagaa ctcatcaaga   4140
agtctgtaga aggcaattct ctgggagtca ggggctgcaa tgccatagag cactaggaac   4200
ctgtctgccc actctccccc tagctcttct gctatgtccc tggttgctag ggcaatgtcc   4260
tggtacctgt cagccactcc cagcctgcca cagtctatga agccagagaa ccttccattt   4320
tcaaccatga tgttgggaag gcaggcatcc ccatgagtca ccactaggtc ctcaccatct   4380
ggcatggatg ccttgagcct ggcaaatagt tcagcagggg ccaggccctg tgttcttca   4440
tccaagtcat cttggtccac caggccagcc tccatcctgg ttctggccct ctctatcctg   4500
tgcttggcct ggtggtcaaa ggggcaggtg gctgggtcaa gggtgtggag tcttctcatg   4560
gcatcagcca tgattgacac tttctcagct ggagctaggt gagaggaaag gaggtcctgc   4620
ccaggcacct cacctagtag gagccagtcc cttccagctt ctgtgaccac atcaaggaca   4680
gctgcacagg gaccccagt tgttgccaac caggagagtc tggcagcctc atcctggagc   4740
tcattgagag ccccactgag gtctgtcttt acaaaaagga ctggcctgcc ttgggctgaa   4800
agtctgaaaa ctgctgcatc agagcaacca atggtctgct gtgcccagtc atagccaaac   4860
agtctctcaa cccaggcagc tggagaacct gcatgtaggc catcttgttc aatcatgatg   4920
gctcctcctg tcaggagagg aaagagaaga aggttagtac aattgctata gtgagttgta   4980
ttatactatg cttatgatta attgtcaaac tagggctgca gggttcatag tgccactttt   5040
cctgcactgc cccatctcct gcccacccet tcccaggcat agacagtcag tgacttacca   5100
aactcacagg agggagaagg cagaagcttt ttgcaaaagc ctaggcctcc aaaaaagcct   5160
cctcactact tctggaatag ctcagaggcc caggggcct gggcctctgc ataaataaaa   5220
aaaattagtc agcctgggc tggggtgggg gcagggtgg ggggccaact gggcaggggt   5280
gggggccac tagtgggact atggttgctg actaattgag atgcatgctt tgcatacttc   5340
tgcctgctgg ggagcctggg gactttccac acctggttgc tgactaattg agatgcatgc   5400
tttgcatact tctgcctgct ggggagcctg gggactttcc acaccctaac tgacacacat   5460
tccacagctg gttctttcag cctcagaagg tacctaacca agttcctctt tcagaggtta   5520
tttcaggccc tgcaggaatt cagtcaatat gttcacccca aaaaagctgt ttgttaactt   5580
gtcaacctca ttctaaaatg tatatagaag cccaaaagac aataacaaaa atattcttgt   5640
agaacaaaat gggaaagaat gttccactaa atatcaagat ttagagcaaa gcatgagatg   5700
tgtggggata dacagtgagg ctgataaaat agagtagagc tcagaaacag acccattgat   5760
atatgtaagt gacctatgaa aaaatatgg cattttacaa tgggaaaatg atggtctttt   5820
tcttttttag aaaacaggg aaatatattt atatgtaaaa aataaaaggg aacccatatg   5880
tcataccata cacacaaaaa aattccagtg aattataagt ctaaatggag aaggcaaaac   5940
tttaaatctt ttagaaaata atatagaagc atgccatcaa gacttcagtg tagagaaaaa   6000
tttcttatga ctcaaagtcc taaccacaaa gaaaagattg ttaattagat tgcatgaata   6060
ttaagactta ttttttaaaat taaaaaacca ttaagaaaag tcaggccata gaatgacaga   6120
aaatatttgc aacacccccag taaagagaat tgtaatatgc agattataaa aagaagtctt   6180
acaaatcagt aaaaaataaa actagacaaa atttgaaca gatgaaagag aaactctaaa   6240
taatcattac acatgagaaa ctcaatctca gaaatcagag aactatcatt gcatatacac   6300
taaattagag aaatattaaa aggctaagta acatctgtgg cttaattaag ttatcctagg   6360
aaaccttaaa acctttaaaa gccttatata ttcttttttt tcttataaaa cttaaaacct   6420
```

-continued

```
tagaggctat ttaagttgct gatttatatt aattttattg ttcaaacatg agagcttagt    6480
acatgaaaca tgagagctta gtacattagc catgagagct tagtacatta gccatgaggg    6540
tttagttcat taaacatgag agcttagtac attaaacatg agagcttagt acatactatc    6600
aacaggttga actgctgatt                                                6620

<210> SEQ ID NO 6
<211> LENGTH: 7922
<212> TYPE: DNA
<213> ORGANISM: Artificial sequence
<220> FEATURE:
<223> OTHER INFORMATION: Synthetic

<400> SEQUENCE: 6
aattcagtca atatgttcac cccaaaaaag ctgtttgtta acttgtcaac ctcattctaa      60
aatgtatata gaagcccaaa agacaataac aaaaatattc ttgtagaaca aaatgggaaa     120
gaatgttcca ctaaatatca agatttagag caaagcatga gatgtgtggg gatagacagt     180
gaggctgata aaatagagta gagctcagaa acagacccat tgatatatgt aagtgaccta     240
tgaaaaaaat atggcatttt acaatgggaa aatgatggtc ttttctttt ttagaaaaac      300 agggaaatat atttatatgt aaaaaataaa agggaaccca tatgtcatac catacacaca     360
aaaaaattcc agtgaattat aagtctaaat ggagaaggca aaactttaaa tcttttagaa     420
aataatatag aagcatgcca tcaagacttc agtgtagaga aaaatttctt atgactcaaa     480
gtcctaacca caaagaaaag attgttaatt agattgcatg aatattaaga cttatttta      540 aaattaaaaa accattaaga aaagtcaggc catagaatga cagaaaatat ttgcaacacc     600
ccagtaaaga gaattgtaat atgcagatta taaaagaag tcttacaaat cagtaaaaaa      660
taaaactaga caaaaatttg aacagatgaa agagaaactc taaataatca ttacacatga     720
gaaactcaat ctcagaaatc agagaactat cattgcatat acactaaatt agagaaatat     780
taaaaggcta agtaacatct gtggcttaat taagttatcc taggaaaacct taaaaccttt     840 aaaagcctta tatattcttt tttttcttat aaaacttaaa accttagagg ctatttaagt     900
tgctgattta tattaatttt attgttcaaa catgagagct tagtacatga aacatgagag     960
cttagtacat tagccatgag agcttagtac attagccatg agggtttagt tcattaaaca    1020
tgagagctta gtacattaaa catgagagct tagtacatac tatcaacagg ttgaactgct    1080
gattttaatt aaaattatct ctaaggcatg tgaactggct gtcttggttt tcatctgtac    1140
ttcatctgct acctctgtga cctgaaacat atttataatt ccattaagct gtgcatatga    1200
tagatttatc atatgtattt tccttaaagg attttttgtaa gaactaattg aattgatacc    1260
tgtaaagtct ttatcacact acccaataaa taataaatct ctttgttcag ctctctgttt    1320
ctataaatat gtaccagttt tattgttttt agtggtagtg attttattct ctttctatat    1380
atatacacac acatgtgtgc attcataaat atatacaatt tttatgaata aaaaattatt    1440
agcaatcaat attgaaaacc actgattttt gtttatgtga gcaaacagca gattaaaagg    1500
aatttcaatt gcctgcaggc ttagaaatat gggggtaggg gtggtggtgg taattctgtt    1560
ttctccccat aggtgagata agcattgggt taaatgtgct ttctctctct ccctctcctt    1620
tcttaagaat taagggacag actatgggct ggaggacttt gaggatgtct gtctcataac    1680
acttgggttg tatctgttct atggggcttg ttttaagctt ggcaacttgc aacagggttc    1740
actgactttc tccccaggcc caaggtactg tcctcttttc atatctgttt tggggcctct    1800
ggggcttgaa tatctgagaa aatataaaca tttcaataat gttctgtggt gagatgagta    1860
```

```
tgagagatgt gtcattcatt tgtatcaatg aatgaatgag gacaattagt gtataaatcc    1920
ttagtacaac aatctgaggg tagggtggt actattcaat ttctatttat aaagatactt    1980
atttctattt atttatgctt gtgacaaatg ttttgtttgg gaccacagga atcacaaaga    2040
tgagtctttg aatttaagaa gttaatggtc caggaataat tacatagctt acaaatgact    2100
atgatatacc atcaaacaag aggttccatg agaaaataat ctgaaaggtt taataagttg    2160
tcaaaggtga gagggctctt ctctagctag agactaatca gaaatacatt cagggataat    2220
tatttgaata gaccttaagg gttgggtaca ttttgttcaa gcattgatgg agaaggagag    2280
tgaatatttg aaaacatttt caactaacca accacccaat ccaacaaaca aaaatgaaa    2340 agaatctcag aaacagtgag ataagagaag gaattttctc acaacccaca tgtatagctc    2400
aactgctctg aagaagtata tatctaatat ttaacactaa catcatgcta ataatgataa    2460
taattactgt cattttttaa tgtctataag taccaggcat ttagaagata ttattccatt    2520
tatatatcaa aataaacttg aggggataga tcattttcat gatatatgag aaaaattaaa    2580
aatcagattg aattatttgc ctgtcataca gctaataatt gaccataaga caattagatt    2640
taaattagtt ttgaatcttt ctaataccaa agttcagttt actgttccat gttgcttctg    2700
agtggcttca cagacttatg aaaaagtaaa tggaatcaga attacatcaa tgcaaaagca    2760
ttgctgtgaa ctctgtactt aggactaaac tttgagcaat aacacatata gattgaggat    2820
tgtttgctgt tagtatacaa actctggttc aaagctcctc tttattgctt gtcttggaaa    2880
atttgctgtt cttcatggtt tctcttttca ctgctatcta tttttctcaa ccactcacat    2940
ggctacaata actgtctgca agcttatgat tcccaaatgt ctatctctag cctcaatctt    3000
gttccagaag ataaaaagta gtattcaaat gcacatcaac atctccactt ggagggctta    3060
aagatgtttc aacatacaaa ctggggagtt ttgcctggaa tgtttcctaa aatgtgtcct    3120
gtagcacata gggtcctctt gttccttaaa atctaattac ttttagccca gtgctcatcc    3180
cacctatggg gagatgagag tgaaaaggga gcctgattaa taattacact aagtcaatag    3240
gcatagagcc aggactgttt gggtaaactg gtcactttat cttaaactaa atatatccaa    3300
aactgaacat gtacttagtt actaagtctt tgactttatc tcattcatac cactcagctt    3360
tatccaggcc actagagttt gaggagaata tttgttatat ttgcaaaata aaataagttt    3420
gcaagttttt tttttctgcc ccaaagagct ctgtgtcctt gaacataaaa tacaaataac    3480
tgctatgctg ttaattattg acaaatgtcc cattttcaac ctaaggaaat accataaagt    3540
aacagatata ccaacaaaag gttactagtt aacaggcatt gcctgaaaag agtataaaag    3600
aatttcagca tgattttcca tattgtgctt ccaccactgc caataacaaa ataactagca    3660
acatggcttc ctaccctggc catcagcatg cctctgcctt tgaccaggct gccagatcta    3720
gaggccatag caacagaaga actgccttga gacctagaag acagcaagaa gccactgaag    3780
tcagacctga gcagaaaatg cccaccctac tgagggttta tatagatggt ccccatggga    3840
tggggaaaac caccaccacc caactgctgg tggccctggg tagcagagat gatattgtct    3900
atgtacctga gccatgact tactggaggg tgctgggggc ttctgagaca attgccaaca    3960
tctacaccac acaacacaga ctggaccagg gtgagatatc tgctgggat gctgctgtgg    4020 taatgacatc tgcccagata acaatgggca tgccttatgc tgtgacagat gctgttctgg    4080
ctcctcatat tggggggag gctgggagct cacatgcccc tccccctgcc ctcaccattt    4140
tcctggacag acatcccatt gccttcatgc tgtgctaccc tgctgccaga taccttatgg    4200
```

```
gcagcatgac cccccaggct gtgctggcct ttgtggccct catccccct accttgcctg    4260 gcacaaacat tgtgttgggg gcccttcctg aggacagaca cattgacaga ctggccaaaa    4320
gacagagacc tggagagaga cttgacctgg ctatgctggc tgccattaga agggtttatg    4380
ggctgcttgc caatactgtg agatatctgc agggaggagg gtcctggaga gaggattggg    4440
gacagctttc tgggactgct gtgcctcccc agggtgctga gccccagagc aatgctggcc    4500 caagaccccca tattgggac accttattta ccctgtttag agccctgag ttgctggccc    4560 ccaatggaga cctgtacaat gtgtttgcct gggccttgga tgtcttggcc aaaagactca    4620
gacccatgca tgtctttatc ctggattatg accaatcccc tgctggctgc agagatgccc    4680
tgctgcaact tacctctggg atggtccaga cccatgtcac caccctggc tccatacca    4740 ccatctgtga cctggccaga acctttgcca gagagatggg ggaggctaac tgagtgcaca    4800
gggcccacca tggagctagc tggccagaca tgataagata cattgatgag tttggacaaa    4860
ccacaactag aatgcagtga aaaaaatgct ttatttgtga aatttgtgat gctattgctt    4920
tatttgtaac cattataagc tgcaataaac aagttaacaa caacaattgc attcatttta    4980
tgtttcaggt tcagggggag gtgtgggagg ttttttaaag caagtaaaac ctctacaaat    5040
gtggtatgga attggagccc cactgtgttc atcttacaga tggaaatact gacattcaga    5100
ggagttagtt aacttgccta ggtgattcag ctaataagtg caagaaagat ttcaatccaa    5160
ggtgatttga ttctgaagcc tgtgctaatc acattcacc aagctacaac ttcattttata    5220 aataataagt cagcttttcaa gggcctttca ggtgtcctgc acttctacaa gctgtgccat    5280
ttagtgaaca caaaatgagc cttctgatga agtagtcttt tcattattttc agatattaga    5340 acactaaaat tcttagctgc cagctgattg aaggctggga caaaattcaa acatgcatct    5400
acaacaatat atatctcaat gttagtctcc aaattctatt gacttcaact caagagaata    5460
taaagagcta gtctttatac actctttaag gtatgatatc atctggaaag taacaaaatt    5520
gatgcaaatt tgaatgaact ttatcatggt gtatttacac aatgtgtttc ttctccctgc    5580
aatgtatttc tttctctaat tccttccatt tgatctttca tacacaatct ggttctgatg    5640 tatgttttt ggatgcactt ttcaactcca aaagacagag ctagttactt tcttcctggt    5700
gctccaagca ctgtatttgt atctgtattc aagccctttg caatattgta ctggatcatt    5760
atttcacctc taggatggct tccccaggca acttgtgttc acccagagac tacattttgt    5820
atcttgttga ccttttgaact tccaccagtg tctaaaaata atatgtatgc aaaattactt    5880
gctatgagaa tgtataatta aacaatataa aaaggagaag caaggagaga aacacaggtg    5940
tgtatttgtg tttgtgtgct taaaaggcag tgtggaaaag gaagaaatgc catttatagt    6000
gaggagacaa agttatatta cctcttatct ggcttttaag gagatttttgc tgagctaaaa    6060 atcctatatt catagaaaag ccttacctga gttgccaata cctcaattct aaaatacagc    6120
atagcaaaac tttaacctcc aaatcaagcc tctacttgaa tccttttctg agggatgaat    6180
aaggcatagg catcaggggc tgttgccaat gtgcattagc tgtttgcagc ctcaccttct    6240
ttcatggagt ttaagatata gtgtatttc ccaaggtttg aactagctct tcatttcttt    6300
atgttttaaa tgcactgacc tcccacattc cctttttagt aaaatattca gaaataattt    6360
aaatacatca ttgcaatgaa aataaatgtt tttattagg cagaatccag atgctcaagg    6420
cccttcataa tatcccccag tttagtagtt ggacttaggg aacaaggaa cctttaatag    6480 aaattggaca gcaagaaagc tctagcttta gaagaactca tcaagaagtc tgtagaaggc    6540
aattctctgg gagtcagggg ctgcaatgcc atagagcact aggaacctgt ctgcccactc    6600
```

```
tcccccctagc tcttctgcta tgtccctggt tgctagggca atgtcctggt acctgtcagc    6660
cactcccagc ctgccacagt ctatgaagcc agagaaccct tccattttcaa ccatgatgtt    6720 gggaaggcag gcatccccat gagtcaccac taggtcctca ccatctggca tggatgcctt    6780
gagcctggca aatagttcag caggggccag gccctggtgt tcttcatcca agtcatcttg    6840
gtccaccagg ccagcctcca tcctggttct ggccctctct atcctgtgct tggcctggtg    6900
gtcaaagggg caggtggctg ggtcaagggt gtggagtctt tcatggcat cagccatgat     6960 tgacactttc tcagctggag ctaggtgaga ggaaaggagg tcctgcccag gcacctcacc    7020
tagtaggagc cagtcccttc cagcttctgt gaccacatca aggacagctg cacaggggac    7080
cccagttgtt gccaaccagg agagtctggc agcctcatcc tggagctcat tgagagcccc    7140
actgaggtct gtctttacaa aaaggactgg cctgccttgg gctgaaagtc tgaaaactgc    7200
tgcatcagag caaccaatgg tctgctgtgc ccagtcatag ccaaacagtc tctcaaccca    7260
ggcagctgga gaacctgcat gtaggccatc ttgttcaatc atgatggctc ctcctgtcag    7320
gagaggaaag agaagaaggt tagtacaatt gctatagtga gttgtattat actatgctta    7380
tgattaattg tcaaactagg gctgcagggt tcatagtgcc acttttcctg cactgcccca    7440
tctcctgccc acccttcccc aggcatagac agtcagtgac ttaccaaact cacaggaggg    7500
agaaggcaga agcttttgc aaaagcctag gcctccaaaa aagcctcctc actacttctg     7560
gaatagctca gaggcccagg gggcctgggc ctctgcataa ataaaaaaaa ttagtcagcc    7620
tggggctggg gtggggcag gggtgggggg ccaactgggc aggggtgggg ggccactagt     7680
gggactatgg ttgctgacta attgagatgc atgctttgca tacttctgcc tgctggggag    7740
cctggggact ttccacacct ggttgctgac taattgagat gcatgctttg catacttctg    7800
cctgctgggg agcctgggga cttttccacac cctaactgac acacattcca cagctggttc    7860
tttcagcctc agaaggtacc taaccaagtt cctctttcag aggttatttc aggccctgca    7920
gg                                                                   7922

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
acggcgacct gtacaacgtg                                                20

<210> SEQ ID NO 8
<211> LENGTH: 18
<212> TYPE: DNA
<213> ORGANISM: Artificial sequence
<220> FEATURE:
<223> OTHER INFORMATION: Synthetic

<400> SEQUENCE: 8
aaacgcctcc gtcccatg                                                  18

<210> SEQ ID NO 9
<211> LENGTH: 21
<212> TYPE: DNA
<213> ORGANISM: Artificial sequence
<220> FEATURE:
<223> OTHER INFORMATION: Synthetic
```

```
<400> SEQUENCE: 9
gcccttcctg aggacagaca c                                        21

<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10
gggtttatgg gctgcttgcc                                          20
```